United States Patent
Dimech et al.

(10) Patent No.: US 9,109,031 B2
(45) Date of Patent: Aug. 18, 2015

(54) LIGANDS THAT BIND TGF-β RECEPTOR RII

(75) Inventors: Caroline J Dimech, Stevenage (GB); Adriaan Allart Stoop, Cambridge (GB); Rudolf Maria De Wildt, Stevenage (GB); Steve Holmes, Cambridge (GB)

(73) Assignee: Glaxo Group Limited (GB)

( * ) Notice: Subject to any disclaimer, the term of this patent is extended or adjusted under 35 U.S.C. 154(b) by 282 days.

(21) Appl. No.: 13/387,376

(22) PCT Filed: Jul. 27, 2010

(86) PCT No.: PCT/EP2010/060867
§ 371 (c)(1),
(2), (4) Date: Jan. 27, 2012

(87) PCT Pub. No.: WO2011/012609
PCT Pub. Date: Feb. 3, 2011

(65) Prior Publication Data
US 2012/0129778 A1     May 24, 2012

Related U.S. Application Data

(60) Provisional application No. 61/229,334, filed on Jul. 29, 2009.

(51) Int. Cl.
*C07K 16/28* (2006.01)
*A61K 39/395* (2006.01)
*C12N 15/13* (2006.01)
*C12N 15/63* (2006.01)
*C07K 16/40* (2006.01)

(52) U.S. Cl.
CPC ............ *C07K 16/2863* (2013.01); *C07K 16/40* (2013.01); *C07K 2317/21* (2013.01); *C07K 2317/56* (2013.01); *C07K 2317/565* (2013.01); *C07K 2317/567* (2013.01); *C07K 2317/569* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

EP      1 245 676 A1      10/2002
WO    WO 03/011908 A2    2/2003

OTHER PUBLICATIONS

U.S. Appl. No. 13/978,228, filed Jul. 3, 2013.*
Bowie et al. Deciphering the message in protein sequences: tolerance to amino acid substitutions. Science, (Mar. 16, 1990) 247 (4948) 1306-10.*
Ngo et al., in The Protein Folding Problem and Tertiary Structure Prediction, Merz and Le Grand (Eds), Aug. 1994, Springer Verlag, pp. 433 and 492-495.*
Brown, C. B., et al., Antibodies directed against the chicken type II TGFbeta receptor identity endothelial cells in the developing chicken and quail. Developmental Dynamics, vol. 215, No. 1, May 1999, pp. 79-85.
Chen, Weizao, et al., Construction of a large phage-displayed human antibody domain library with a scaffold based on a newly identified highly soluble, stable heavy chain variable domain. Journal of Molecular Biology, vol. 382, No. 3, Oct. 10, 2008, pp. 779-789.
De Crescenzo, Gregory, et al., Three key residues underlie the differential affinity of the TGFbeta isoforms for the TGFbeta type II receptor. Journal of Molecular Biology, vol. 355, No. 1, Jan. 6, 2006, pp. 47-62.
De Crescenzo, Gregory, et al., transforming growth factor-bata (TGF-beta) binding to the extracellular domain of the typr II receptor capture on a biosensor surface using a new coiled-coli capture system demonstrates that avidity contributes significantly to high affinity binding. Journal of Molecular Biology, vol. 328, No. 5, May 16, 2003, pp. 1173-1183.
Deep, Shashank, et al., Solution structure and backbone dynamics of the TGFbeta type II receptor extracellular domain. Biochemistry, vol. 42, No. 34, Sep. 2, 2003, pp. 10126-10139.
Demarest, Stephen, J., et al., Antibody therapeutics, antibody engineering, and the merits of protein stability. Current Opinion in Drug Discovery and Development, vol. 11, No. 5, Sep. 1, 2008, pp. 675-687.
Derynck, R., et al., TGF-beta signaling in tumor suppression and cancer progression, Nature Genetics, vol. 29, No. 2, Oct. 2001, pp. 117-129.
Marlow, Michael, S. et al., Solution structure of the chick TGFbeta type II receptor ligand-binding domain. Journal of Molecular Biology, vol. 326, No. 4, Feb. 28, 2003, pp. 989-997.
Hall, F. L., et al. Transforming growth factor-beta type II receptor signaling: intrinsic/associated casein kinase activity, receptor interactions and functional effects of blocking antibodies. The Biochemical Journal, vol. 316 (pt. 1), May 15, 1996, pp. 303-310.
Kasuga, H., et al., Effects of anti-TGF-beta type II receptor antibody on experimental glomerulonephritis. Kidney International, vol. 60, No. 5, Nov. 2001, pp. 1745-1755.
Rudikoff, S., et al., Single amino acid substitution altering antigen-binding specificity. PNAS, vol. 79, Mar. 1, 1982, pp. 1979-1983.
Saerens, Dirk, et al., Single-domain antibodies as building blocks for novel therapeutics. Current Opinion in Pharmacology, vol. 8, No. 5, Oct. 2008, pp. 600-608.

(Continued)

*Primary Examiner* — David Romeo
(74) *Attorney, Agent, or Firm* — William T. Han; Jason C. Fedon

(57) ABSTRACT

The disclosure provides an anti-TGFbetaRII immunoglobulin single variable domain. The disclosure also provides a polypeptide, ligand or pharmaceutical composition for treating a disease associated with TGFbeta signaling and a disease selected from the group of: tissue fibrosis, such as pulmonary fibrosis, including idiopathic pulmonary fibrosis, liver fibrosis, including cirrhosis and chronic hepatitis, rheumatoid arthritis, ocular disorders, or fibrosis of the skin, including keloid of skin, and kidney such as nephritis, kidney fibrosis and nephrosclerosis, and a vascular condition, such as restenosis.

16 Claims, 29 Drawing Sheets

(56) References Cited

OTHER PUBLICATIONS

Weers, Jeffry G., et al., Design of fine particles for pulmonary drug delivery. Expert Opinion on Drug Delivery, vol. 4, No. 3, May 2007, pp. 297-313.

Wesolowski, Janusz, et al., Single Domain antibodies: promising experimental and therapeutic tools in infection and immunity. Medical Microbiology and Immunology, vol. 198, No. 3, Jun. 16, 2009, pp. 157-174.

* cited by examiner

FIGURE 1

>DOM23h-33 (SEQ ID NO: 1)

EVQLLESGGGLVQPGGSLRLSCAASGFTFSQYRMWWVRQAPGKGLEWVSA
IAPSGDNTYYADSVKGRFTISRDNSKNTLYLQMNSLRAEDTAVYYCAKHRT
SFDYWGQGTLVTVSS

>DOM23h-251 (SEQ ID NO: 2)
EVQLLESGGGLVQPGGSLRLSCAASGFTFSDYDMWWVRQAPGKGLEWVSK
ITQKGDFTYYADSVKGRFTISRDNSKNTLYLQMNSLRAEDTAVYYCAKDAT
HFDYWGQGTLVTVSS

>DOM23h-262 (SEQ ID NO: 3)
EVQLLESGGGLVQPGGSLRLSCAASGFTFFNYEMAWARQAPGKGLEWVSLI
SAEGTRTYYADSVKGRFTISRDNSKNTLYLQMNSLRAEDTAVYYCAKRRD
ASMGHTTRRFDYWGQGTLVTVSS

>DOM23h-271 (SEQ ID NO: 4)
EVQLLESGGGLVQPGGSLRLSCAASGFTFTEYRMWWVRQAPGKGLEWVSS
IEPIGNRTYYADSVKGRFTISRDNSKNTLYLQMNSLRAEDTAVYYCAKQIPG
HKWTANSRFDYWGQGTLVTVSS

>DOM23h-348 (SEQ ID NO: 5)
EVQLLESGGGLVQPGGSLRLSCAASGFTFSDYDMAWARQAPGKGLEWVSR
ISHSGYSTYYADSVKGRFTISRDNSKNTLYLQMNSLRAEDTAVYYCAKRSW
DGVHAQFDYWGQGTLVTVSS

>DOM23h-435 (SEQ ID NO: 6)
EVQLLESGGGLVQPGGSLRLTCAASGFTFTDDRMWWVRQAPGKGLEWVS
AIDPQGQHTYYADSVKGRFTISRDNSKNTLYLQMNSLRAEDTAVYYCAKH
NSSFDYWGQGTLVTVSS

>DOM23h-436 (SEQ ID NO: 7)
EVQLLESGGGLVQPGGSLRLSCAASGFTFSDYKMGWVRQAPGKGLEWVSSI
WPNGGLTYYADSVKGRFTISRDNSKNTLYLQMNSLRAEDTAVYYCAKDH
MGFDYWGQGTLVTVSS

>DOM23h-437 (SEQ ID NO: 8)
EVQLLESGGGLVQPGGSLRLSCAASGFTFSDYRMWWVRQAPGKGLEWVSA
IDSQGHTTYYADSVKGRFTISRDNSKNTLYLQMNSLRAEDTAVYYCAKYGG
YFDYWGQGTLVTVSS

>DOM23h-438 (SEQ ID NO: 9)
EVQLLESGGGLVQPGGSLRLSCAASGFTFAQGDMWWVRQAPGKGLEWVS
RIGMDGDKTYYADSVKGRFTISRDNSKNTLYLQMNSLRAEDTAVYYCAKG
PSSTSPFDYWGQGTLVTVSS

FIGURE 1 (continued)

>DOM23h-439 (SEQ ID NO: 10)
EVQLLESGGGLVQPGGSLRLSCAASGFTFGTEQMWWVRQAPGKGLEWVSR
IDSPGGRTYYADSVKGRFTISRDNSKNTLYLQMNSLRAEDTAVYYCAKRHA
AGVSGTYFDYWGQGTLVTVSS

>DOM23h-440 (SEQ ID NO: 11)
EVQLLESGGGLVQPGGSLRLSCAASGFTFTDDRMWWVRQAPGKGLEWVSA
IDPQGQHTYYADSVKGRFTISRDNSKNTLYLQMNSLRAEDTAVYYCAKELL
SFDYWGQGTLVTVSS

>DOM23h-262-6 (SEQ ID NO: 12)
EVQLLESGGGLVQPGGSLRLSCAASGFTFFNYEMAWARQAPGKGLEWVSLI
SAEGTRTYYANSVKGRFTISRDNSKNTLYLQMNSLRAEDTAVYYCAKRRD
ASMGHTTRRFDHWGQGTLVTVSS

>DOM23h-262-10 (SEQ ID NO: 13)
EVQLLESGGGLVQPGGSLRLSCAASGFTFFNYEMAWARRAPGKGLEWVSLI
SADGTRTYYANSVRGRFTISRDNSKNTLYLQMNSLRAEDTAVYYCAKRRD
ASMGHTTRRFDYSGQGTLVTVSS

>DOM23h-271-3 (SEQ ID NO: 14)
EVQLLESGGGLVQPGGSLRLSCTASGFTFTEYRMWWVRQAPGKGLEWVSLI
EPIGNRTYYADSVKGRFTISRDNSKNTLYLQMNSLRAEDTAVYYCAKQIPG
HMWTANPRSDYWGQGTQVTVSS

>DOM23h-271-7 (SEQ ID NO: 15)
EVQLLESGGGLVQPGGSLRLSCAASGFTFTEYRMWWVRQAPGKGLEWVSA
IEPIGNRTYYADSVKGRFTISRDNSKNTLYLQMNSLRAEDTAVYYCAKQIPG
RKWTANSRFDYWGQGTLVTVSS

>DOM23h-271-12 (SEQ ID NO: 16)
EVQLLESGGGLVQPGGSLRLSCTASGFTFTEYRMWWVRQAPGKGLEWVSLI
EPIGNRTYYANSVRGRFTISRDNSKNTLYLQMNSLRAEDTAVYYCAKQIPG
HMWTANPRSDYWGQGTQVTVSS

>DOM23h-271-13 (SEQ ID NO: 17)
EVQLLESGGGLVQPGGSLRLSCAASGFTFTEYRMWWVRQAPGKGLEWVSA
IEPIGNRTYYANSVRGRFTISRDNSKNTLYLQMNSLRAEDTAVYYCAKQIPG
RKWTANSRFDYWGQGTLVTVSS

>DOM23h-437-4 (SEQ ID NO: 18)
EVQLLESGGGLVQPGGSLRLSCAASGFTISDYRMWWVRQAPGKGLEWVSA
IDSQGHTTYYADSVRGRFTISRDNSKNTLYLQMNSLRAEDTAVYYCAKYGG
YFDYWGQGTLVTVSS

FIGURE 1 (continued)

>DOM23h-437-6 (SEQ ID NO:19)
EVQLLESGGGLVQPGGSLRLSCATSGFTFSDYRMWWVRQAPGKGLEWVSA
IDSQGHTTYYADSVKGRFTISRDNSKNTLYLQMNSLRAEDTAVYYCAKYGG
YFDYWGQGTLVTVSS

>DOM23h-437-8 (SEQ ID NO: 20)
EVQLLESGGGLVQPGGSLRLSCAASGFTISDYRMWWVRQAPGKGLEWVSA
IDSQGHTTYYANSVRGRFTISRDNSKNTLYLQMNSLRAEDTAVYYCAKYGG
YFDYWGQGTLVTVSS

>DOM23h-437-9 (SEQ ID NO: 21)
EVQLLESGGGLVQPGGSLRLSCATSGFTFSDYRMWWVRQAPGKGLEWVSA
IDSQGHTTYYANSVRGRFTISRDNSKNTLYLQMNSLRAEDTAVYYCAKYGG
YFDYWGQGTLVTVSS

>DOM23h-439-6 (SEQ ID NO: 22)
EVQLLESGGGLVRPGGSLRLSCAASGFTFGTEQMWWVRQAPGKGLEWVSR
IDSPGGRTYYADSVRGRFTISRDNSKNTLYLQMNSLRAEDTAVYYCAKRHA
AGVSGTYFDYWGQGTLVTVSS

>DOM23h-439-8 (SEQ ID NO: 23)
EVQLLESGGGLVRPGGSLRLSCAASGFTFGTEQMWWVRQAPGKGLEWVSR
IDSPGGRTYYANSVRGRFTISRDNSKNTLYLQMNSLRAEDTAVYYCAKRHA
AGVSGTYFDYWGQGTLVTVSS

>DOM23h-33 (SEQ ID NO:24)
GAGGTGCAGCTGTTGGAGTCTGGGGGAGGCTTGGTACAGCCTGGGGGGT
CCCTGCGTCTCTCCTGTGCAGCCTCCGGATTCACCTTTTCGCAGTATCGG
ATGTGGTGGGTCCGCCAGGCTCCAGGGAAGGGTCTAGAGTGGGTCTCAG
CGATTGCGCCTTCTGGTGATAATACATACTACGCAGACTCCGTGAAGGG
CCGGTTCACCATCTCCCGCGACAATTCCAAGAACACGCTGTATCTGCAAA
TGAACAGCCTGCGTGCCGAGGACACCGCGGTATATTACTGTGCGAAACA
TCGGACTTCGTTTGACTACTGGGGTCAGGGAACCCTGGTCACCGTCTCGA
GC

>DOM23h-251 (SEQ ID NO: 25)
GAGGTGCAGCTGTTGGAGTCTGGGGGAGGCTTGGTACAGCCTGGGGGGT
CCCTGCGTCTCTCCTGTGCAGCCTCCGGATTCACCTTTTCGGATTATGATA
TGTGGTGGGTCCGCCAGGCTCCAGGGAAGGGTCTGGAGTGGGTCTCAAA
GATTACGCAGAAGGGTGATTTTACATACTACGCAGACTCCGTGAAGGGC
CGGTTCACCATCTCCCGCGACAATTCCAAGAACACGCTGTATCTGCAAAT
GAACAGCCTGCGTGCCGAGGACACCGCGGTATATTACTGTGCGAAAGAT
GCTACTCATTTTGACTACTGGGGTCAGGGAACCCTGGTCACCGTCTCGAG
C

FIGURE 1 (continued)

>DOM23h-262 (SEQ ID NO: 26)
GAGGTGCAGCTGTTGGAGTCTGGGGGAGGCTTGGTACAGCCTGGGGGGT
CCCTGCGTCTCTCCTGTGCAGCCTCCGGATTCACCTTTTTTAATTATGAGA
TGGCGTGGGCCCGCCAGGCTCCAGGGAAGGGTCTAGAGTGGGTCTCATT
GATTAGTGCTGAGGGTACGAGGACATACTACGCAGACTCCGTGAAGGGC
CGGTTCACCATCTCCCGCGACAATTCCAAGAACACGCTGTATCTGCAAAT
GAACAGCCTGCGTGCCGAGGACACCGCGGTATATTACTGTGCAAAACGG
CGGGATGCTAGTATGGGTCATACTACTCGGCGGTTTGACTACTGGGGTCA
GGGAACCCTGGTCACCGTCTCGAGC

>DOM23h-271 (SEQ ID NO: 27)
GAGGTGCAGCTGTTGGAGTCTGGGGGAGGCTTGGTACAGCCTGGGGGGT
CCCTGCGTCTCTCCTGTGCAGCCTCCGGATTCACCTTTACGGAGTATAGG
ATGTGGTGGGTCCGCCAGGCTCCAGGGAAGGGTCTAGAGTGGGTCTCAT
CGATTGAGCCGATTGGTAATCGTACATACTACGCAGACTCCGTGAAGGG
CCGGTTCACCATCTCCCGCGACAATTCCAAGAACACGCTGTATCTGCAAA
TGAACAGCCTGCGTGCCGAGGATACCGCGGTATATTACTGTGCGAAACA
GATTCCGGGGCATAAGTGGACTGCTAATTCGCGGTTTGACTACTGGGGTC
AGGGAACCCTGGTCACCGTCTCGAGCG

>DOM23h-348 (SEQ ID NO: 28)
GAGGTGCAGCTGTTGGAGTCTGGGGGGGGCTTGGTACAGCCTGGGGGGT
CCCTGCGTCTCTCCTGTGCAGCCTCCGGATTCACCTTTAGTGATTATGAT
ATGGCGTGGGCCCGCCAGGCTCCAGGGAAGGGTCTAGAGTGGGTCTCAC
GTATTTCTCATAGTGGTTATTCTACATACTACGCAGACTCCGTGAAGGGC
CGGTTCACCATCTCCCGCGACAATTCCAAGAACACGCTGTATCTGCAAAT
GAACAGCCTGCGTGCCGAGGACACCGCGGTATATTACTGTGCGAAACGT
TCGTGGGATGGGGTTCATGCGCAGTTTGACTACTGGGGTCAGGGAACCC
TGGTCACCGTCTCGAGC

>DOM23h-435 (SEQ ID NO: 29)
GAGGTGCAGCTGTTGGAGTCTGGGGGAGGCTTGGTACAGCCTGGGGGGT
CCCTGCGTCTCACCTGTGCAGCCTCCGGATTCACCTTTACGGATGATAGG
ATGTGGTGGGTCCGCCAGGCTCCAGGGAAGGGTCTAGAGTGGGTCTCAG
CTATTGATCCTCAGGGTCAGCATACATACTACGCAGACTCCGTGAAGGG
CCGGTTCACCATCTCCCGCGACAATTCCAAGAACACGCTGTATCTGCAAA
TGAACAGCCTGCGTGCCGAGGATACCGCGGTATATTACTGTGCGAAACA
TAATTCGAGTTTTGACTACTGGGGTCAGGGAACCCTGGTCACCGTCTCGA
GCG

FIGURE 1 (continued)

>DOM23h-436 (SEQ ID NO: 30)
GAGGTGCAGCTGTTGGAGTCTGGGGGAGGCTTGGTACAGCCTGGGGGGT
CCCTGCGTCTCTCCTGTGCAGCCTCCGGATTCACCTTTAGTGATTATAAG
ATGGGTTGGGTCCGCCAGGCTCCAGGGAAGGGTCTAGAGTGGGTCTCAA
GTATTTGGCCTAATGGTGGTTTGACATACTACGCAGACTCCGTGAAGGGC
CGGTTCACCATCTCCCGCGACAATTCCAAGAACACGCTGTATCTGCAAAT
GAACAGCCTGCGTGCCGAGGATACCGCGGTATATTACTGTGCAAAGAT
CATATGGGTTTTGACTACTGGGGTCAGGGAACCCTGGTCACCGTCTCGAG
CG

>DOM23h-437 (SEQ ID NO: 31)
GAGGTGCAGCTGTTGGAGTCTGGGGGAGGCTTGGTACAGCCTGGGGGGT
CCCTGCGTCTCTCCTGTGCAGCCTCCGGATTCACCTTTTCTGATTATCGTA
TGTGGTGGGTCCGCCAGGCTCCAGGGAAGGGTCTAGAGTGGGTCTCAGC
GATTGATTCTCAGGGTCATACGACATACTACGCAGACTCCGTGAAGGGC
CGGTTCACCATCTCCCGCGACAATTCCAAGAACACGCTGTATCTGCAAAT
GAACAGCCTGCGTGCCGAGGATACCGCGGTATATTACTGTGCAAATAT
GGGGGTTATTTTGACTACTGGGGTCAGGGAACCCTGGTCACCGTCTCGA
GCG

>DOM23h-438 (SEQ ID NO: 32)
GAGGTGCAGCTGTTGGAGTCTGGGGGAGGCTTGGTACAGCCTGGGGGGT
CCCTGCGTCTCTCCTGTGCAGCCTCCGGATTCACCTTTGCGCAGGGGGAT
ATGTGGTGGGTCCGCCAGGCTCCAGGGAAGGGTCTGGAGTGGGTCTCAC
GTATTGGTATGGATGGTGATAAGACATACTACGCAGACTCCGTGAAGGG
CCGGTTCACCATCTCCCGCGACAATTCCAAGAACACGCTGTATCTGCAAA
TGAACAGCCTGCGTGCCGAGGACACCGCGGTATATTACTGTGCAAAGG
TCCTTCGAGTACTAGTCCGTTTGACTACTGGGGTCAGGGAACCCTGGTCA
CCGTCTCGAGCG

>DOM23h-439 (SEQ ID NO: 33)
GAGGTGCAGCTGTTGGAGTCTGGGGGAGGCTTGGTACAGCCTGGGGGGT
CCCTGCGTCTCTCCTGTGCAGCCTCCGGATTCACCTTTGGGACGGAGCAG
ATGTGGTGGGTCCGCCAGGCTCCAGGGAAGGGTCTAGAGTGGGTCTCAC
GTATTGATTCGCCTGGTGGGAGGACATACTACGCAGACTCCGTGAAGGG
CCGGTTCACCATCTCCCGCGACAATTCCAAGAACACGCTGTATCTGCAAA
TGAACAGCCTGCGTGCCGAGGACACCGCGGTATATTACTGTGCAAACG
GCATGCGGCTGGGGTTTCGGGTACTTATTTTGACTACTGGGGTCAGGGAA
CCCTGGTCACCGTCTCGAGCG

FIGURE 1 (continued)

>DOM23h-440 (SEQ ID NO: 34)
GAGGTGCAGCTGTTGGAGTCTGGGGGAGGCTTGGTACAGCCTGGGGGGT
CCCTGCGTCTCTCCTGTGCAGCCTCCGGATTCACCTTTACGGATGATAGG
ATGTGGTGGGTCCGCCAGGCTCCAGGGAAGGGTCTAGAGTGGGTCTCAG
CTATTGATCCTCAGGGTCAGCATACATACTACGCAGACTCCGTGAAGGG
CCGGTTCACCATCTCCCGCGACAATTCCAAGAACACGCTGTATCTGCAAA
TGAACAGCCTGCGTGCCGAGGACACCGCGGTATATTACTGTGCGAAAGA
GCTGCTTAGTTTTGACTACTGGGGTCAGGGAACCCTGGTCACCGTCTCGA
GCG

>DOM23h-262-6 (SEQ ID NO: 35)
GAGGTGCAGCTGTTGGAGTCTGGGGGAGGCTTGGTACAGCCTGGGGGGT
CCCTGCGTCTCTCCTGTGCAGCCTCCGGATTCACCTTTTTTAATTATGAGA
TGGCGTGGGCCCGCCAGGCTCCAGGGAAGGGCCTAGAGTGGGTCTCATT
GATTAGTGCTGAGGGTACGAGGACATACTACGCAAACTCCGTGAAGGGC
CGGTTCACCATCTCCCGCGACAATTCCAAGAACACGCTGTATCTGCAAAT
GAACAGCCTGCGTGCCGAGGACACCGCGGTATATTACTGTGCAAAACGG
CGGGATGCTAGTATGGGTCATACTACTCGGCGGTTTGACCACTGGGGTC
AGGGAACCCTGGTCACCGTCTCGAGC

>DOM23h-262-10 (SEQ ID NO: 36)
GAGGTGCAGCTGTTGGAGTCTGGGGGAGGCTTAGTACAGCCCGGGGGGT
CCCTGCGTCTCTCCTGTGCAGCCTCCGGATTCACCTTTTTTAATTATGAGA
TGGCGTGGGCCCGCCGGGCTCCAGGGAAGGGTCTAGAGTGGGTCTCATT
GATTAGTGCTGATGGTACGAGGACATACTACGCAAACTCCGTGAGGGGC
CGGTTCACCATCTCCCGCGACAATTCCAAGAACCGCTGTATCTGCAAATG
AACAGCCTGCGTGCCGAGGACACCGCGGTATATTACTGTGCAAAACGGC
GGGATGCTAGTATGGGTCATACTACTCGGCGGTTTGACTACTCGGGTCAG
GGAACCCTGGTCACCGTCTCGAGC

>DOM23h-271-3 (SEQ ID NO: 37)
GAGGTGCAGCTGTTGGAGTCTGGGGGAGGCTTGGTACAGCCTGGGGGGT
CCCTGCGTCTCTCCTGCACAGCCTCCGGATTCACCTTTACGGAGTATAGG
ATGTGGTGGGTCCGCCAGGCTCCAGGGAAGGGTCTAGAGTGGGTCTCAT
TGATTGAGCCGATTGGTAATCGTACATACTACGCAGACTCCGTGAAGGG
CCGGTTCACCATCTCCCGCGACAATTCCAAGAACACGCTGTATCTGCAAA
TGAACAGCCTGCGTGCTGAGGATACCGCGGTATATTACTGTGCGAAACA
GATTCCGGGGCATATGTGGACTGCTAATCCGCGGTCTGACTACTGGGGTC
AGGGAACCCAGGTCACCGTCTCGAGC

FIGURE 1 (continued)

>DOM23h-271-7 (SEQ ID NO: 38)
GAGGTGCAGCTGTTGGAGTCTGGGGGAGGCTTGGTACAGCCTGGGGGGT
CCCTGCGTCTCTCCTGTGCAGCCTCCGGATTCACCTTTACGGAGTATAGG
ATGTGGTGGGTCCGCCAGGCTCCGGGGAAGGGTCTCGAGTGGGTCTCAG
CGATTGAGCCGATTGGTAATCGTACATACTACGCAGACTCCGTGAAGGG
CCGGTTCACCATCTCCCGCGACAATTCCAAGAACACGCTGTATCTGCAAA
TGAACAGCCTGCGTGCCGAGGATACCGCGGTATATTACTGTGCGAAACA
GATTCCGGGGCGTAAGTGGACTGCTAATTCGCGGTTTGACTACTGGGGTC
AGGGAACCCTGGTCACCGTCTCGAGC

>DOM23h-271-12 (SEQ ID NO: 39)
GAGGTGCAGCTGTTGGAGTCTGGGGGAGGCTTGGTACAGCCTGGGGGGT
CCCTGCGTCTCTCCTGCACAGCCTCCGGATTCACCTTTACGGAGTATAGG
ATGTGGTGGGTCCGCCAGGCTCCAGGGAAGGGTCTAGAGTGGGTCTCAT
TGATTGAGCCGATTGGTAATCGTACATACTACGCAAACTCCGTGAGGGG
CCGGTTCACCATCTCCCGCGACAATTCCAAGAACACGCTGTATCTGCAAA
TGAACAGCCTGCGTGCTGAGGATACCGCGGTATATTACTGTGCGAAACA
GATTCCGGGGCATATGTGGACTGCTAATCCGCGGTCTGACTACTGGGGTC
AGGGAACCCAGGTCACCGTCTCGAGC

>DOM23h-271-13 (SEQ ID NO: 40)
GAGGTGCAGCTGTTGGAGTCTGGGGGAGGCTTGGTACAGCCTGGGGGGT
CCCTGCGTCTCTCCTGTGCAGCCTCCGGATTCACCTTTACGGAGTATAGG
ATGTGGTGGGTCCGCCAGGCTCCGGGGAAGGGTCTCGAGTGGGTCTCAG
CGATTGAGCCGATTGGTAATCGTACATACTACGCAAACTCCGTGAGGGG
CCGGTTCACCATCTCCCGCGACAATTCCAAGAACACGCTGTATCTGCAAA
TGAACAGCCTGCGTGCCGAGGATACCGCGGTATATTACTGTGCGAAACA
GATTCCGGGGCGTAAGTGGACTGCTAATTCGCGGTTTGACTACTGGGGTC
AGGGAACCCTGGTCACCGTCTCGAGC

>DOM23h-437-4 (SEQ ID NO: 41)
GAGGTGCAGCTGTTGGAGTCTGGGGGAGGCTTGGTACAGCCTGGGGGGT
CCCTGCGTCTCTCCTGTGCAGCCTCCGGATTCACCATTTCTGATTATCGTA
TGTGGTGGGTCCGCCAGGCTCCAGGGAAGGGTCTAGAGTGGGTCTCAGC
GATTGATTCTCAGGGTCATACGACATACTACGCAGACTCCGTGAGGGGC
CGGTTCACCATCTCCCGCGACAATTCCAAGAACACGCTGTATCTGCAAAT
GAACAGCCTGCGTGCCGAGGATACCGCGGTATATTACTGTGCGAAATAT
GGGGGTTATTTTGACTACTGGGGTCAGGGAACCCTGGTCACCGTCTCGA
GC

FIGURE 1 (continued)

>DOM23h-437-6 (SEQ ID NO:42)
GAGGTGCAGCTGTTGGAGTCTGGGGGAGGCTTGGTACAGCCTGGGGGGT
CCCTGCGTCTCTCCTGTGCAACCTCCGGATTCACCTTTTCTGATTATCGTA
TGTGGTGGGTCCGCCAGGCTCCAGGGAAGGGTCTAGAGTGGGTCTCAGC
GATTGATTCTCAGGGTCATACGACATACTACGCAGACTCCGTGAAGGGC
CGGTTCACCATCTCCCGCGACAATTCCAAGAACACGCTGTATCTGCAAAT
GAACAGCCTGCGCGCCGAGGATACCGCGGTATATTACTGTGCGAAATAT
GGGGGTTATTTTGACTACTGGGGTCAGGGAACCCTGGTCACCGTCTCGA
GC

>DOM23h-437-8 (SEQ ID NO: 43)
GAGGTGCAGCTGTTGGAGTCTGGGGGAGGCTTGGTACAGCCTGGGGGGT
CCCTGCGTCTCTCCTGTGCAGCCTCCGGATTCACCATTTCTGATTATCGTA
TGTGGTGGGTCCGCCAGGCTCCAGGGAAGGGTCTAGAGTGGGTCTCAGC
GATTGATTCTCAGGGTCATACGACATACTACGCAAACTCCGTGAGGGGC
CGGTTCACCATCTCCCGCGACAATTCCAAGAACACGCTGTATCTGCAAAT
GAACAGCCTGCGTGCCGAGGATACCGCGGTATATTACTGTGCGAAATAT
GGGGGTTATTTTGACTACTGGGGTCAGGGAACCCTGGTCACCGTCTCGA
GC

>DOM23h-437-9 (SEQ ID NO: 44)
GAGGTGCAGCTGTTGGAGTCTGGGGGAGGCTTGGTACAGCCTGGGGGGT
CCCTGCGTCTCTCCTGTGCAACCTCCGGATTCACCTTTTCTGATTATCGTA
TGTGGTGGGTCCGCCAGGCTCCAGGGAAGGGTCTAGAGTGGGTCTCAGC
GATTGATTCTCAGGGTCATACGACATACTACGCAAACTCCGTGAGGGGC
CGGTTCACCATCTCCCGCGACAATTCCAAGAACACGCTGTATCTGCAAAT
GAACAGCCTGCGCGCCGAGGATACCGCGGTATATTACTGTGCGAAATAT
GGGGGTTATTTTGACTACTGGGGTCAGGGAACCCTGGTCACCGTCTCGA
GC

>DOM23h-439-6 (SEQ ID NO: 45)
GAGGTGCAGCTGTTGGAGTCTGGGGGAGGCTTGGTACGGCCTGGGGGGT
CCCTGCGTCTCTCCTGTGCAGCCTCCGGATTCACCTTTGGGACGGAGCAG
ATGTGGTGGGTCCGCCAGGCTCCAGGGAAGGGTCTAGAGTGGGTCTCAC
GAATTGATTCACCTGGTGGGAGGACATACTACGCAGACTCCGTGAGGGG
CCGGTTCACCATCTCCCGCGACAATTCCAAGAACACGCTGTATCTGCAAA
TGAACAGCCTGCGTGCCGAGGACACCGCGGTATATTACTGTGCGAAACG
GCATGCGGCTGGGGTTTCGGGTACTTATTTTGACTACTGGGGTCAGGGAA
CCCTGGTCACCGTCTCGAGC

FIGURE 1 (continued)

\>DOM23h-439-8 (SEQ ID NO: 46)
GAGGTGCAGCTGTTGGAGTCTGGGGGAGGCTTGGTACGGCCTGGGGGGT
CCCTGCGTCTCTCCTGTGCAGCCTCCGGATTCACCTTTGGGACGGAGCAG
ATGTGGTGGGTCCGCCAGGCTCCAGGGAAGGGTCTAGAGTGGGTCTCAC
GAATTGATTCACCTGGTGGGAGGACATACTACGCAAACTCCGTGAGGGG
CCGGTTCACCATCTCCCGCGACAATTCCAAGAACACGCTGTATCTGCAAA
TGAACAGCCTGCGTGCCGAGGACACCGCGGTATATTACTGTGCGAAACG
GCATGCGGCTGGGGTTTCGGGTACTTATTTTGACTACTGGGGTCAGGGAA
CCCTGGTCACCGTCTCGAGC

FIGURE 2

Positions 1–20:

| Kabat Residue | E | V | Q | L | L | E | S | G | G | G | L | V | Q | P | G | G | S | L | R | L |
|---|---|---|---|---|---|---|---|---|---|---|---|---|---|---|---|---|---|---|---|---|
| | | | | | 5 | | | | | 10 | | | | | 15 | | | | | 20 |
| DOM23h-251 | . | . | . | . | . | . | . | . | . | . | . | . | . | . | . | . | . | . | . | . |
| DOM23h-262 | . | . | . | . | . | . | . | . | . | . | . | . | . | . | . | . | . | . | . | . |
| DOM23h-271 | . | . | . | . | . | . | . | . | . | . | . | . | . | . | . | . | . | . | . | . |
| DOM23h-33  | . | . | . | . | . | . | . | . | . | . | . | . | . | . | . | . | . | . | . | . |
| DOM23h-348 | . | . | . | . | . | . | . | . | . | . | . | . | . | . | . | . | . | . | . | . |
| DOM23h-435 | . | . | . | . | . | . | . | . | . | . | . | . | . | . | . | . | . | . | . | . |
| DOM23h-436 | . | . | . | . | . | . | . | . | . | . | . | . | . | . | . | . | . | . | . | . |
| DOM23h-437 | . | . | . | . | . | . | . | . | . | . | . | . | . | . | . | . | . | . | . | . |
| DOM23h-438 | . | . | . | . | . | . | . | . | . | . | . | . | . | . | . | . | . | . | . | . |
| DOM23h-439 | . | . | . | . | . | . | . | . | . | . | . | . | . | . | . | . | . | . | . | . |
| DOM23h-440 | . | . | . | . | . | . | . | . | . | . | . | . | . | . | . | . | . | . | . | . |

Positions 21–40:

| Kabat Residue | S | C | A | A | S | G | F | T | F | S | D | Y | D | M | W | W | V | R | Q | A |
|---|---|---|---|---|---|---|---|---|---|---|---|---|---|---|---|---|---|---|---|---|
| | | | | | 25 | | | | | 30 | | | | | 35 | | | | | 40 |
| DOM23h-251 | . | . | . | . | . | . | . | . | . | F | N | . | E | . | A | . | . | . | . | . |
| DOM23h-262 | . | . | . | . | . | . | . | . | . | T | E | . | R | . | . | . | . | . | . | . |
| DOM23h-271 | . | . | . | . | . | . | . | . | . | . | Q | . | R | . | A | . | A | . | . | . |
| DOM23h-33  | . | . | . | . | . | . | . | . | . | . | . | . | . | . | . | . | . | . | . | . |
| DOM23h-348 | . | . | . | . | . | . | . | . | . | T | . | D | R | . | A | . | A | . | . | . |
| DOM23h-435 | T | . | . | . | . | . | . | . | . | . | . | . | K | . | . | . | . | . | . | . |
| DOM23h-436 | . | . | . | . | . | . | . | . | . | . | . | . | R | . | . | . | . | . | . | . |
| DOM23h-437 | . | . | . | . | . | . | . | . | . | . | Q | G | . | . | G | . | . | . | . | . |
| DOM23h-438 | . | . | . | . | . | . | . | . | . | A | H | E | Q | . | . | . | . | . | . | . |
| DOM23h-439 | . | . | . | . | . | . | . | . | . | G | . | D | R | . | . | . | . | . | . | . |
| DOM23h-440 | . | . | . | . | . | . | . | . | . | T | . | . | . | . | . | . | . | . | . | . |

FIGURE 2 (continued)

Kabat positions ~42–59:

| Kabat Residue | P | G | K | G | L(45) | E | W | V | S | K(50) | H | T | S | A | G(54) | D | T | N | F | R | H | Y | Y(59) |
|---|---|---|---|---|---|---|---|---|---|---|---|---|---|---|---|---|---|---|---|---|---|---|---|
| DOM23h-251 | . | . | . | . | . | . | . | . | . | L | . | S | A | P | . | T | . | . | R | . | . | . | . |
| DOM23h-262 | . | . | . | . | . | . | . | . | . | S | . | E | P | P | . | N | Y | . | R | . | . | . | . |
| DOM23h-271 | . | . | . | . | . | . | . | . | . | A | . | A | P | H | . | . | Q | . | N | . | . | . | . |
| DOM23h-33  | . | . | . | . | . | . | . | . | . | R | . | S | H | P | . | Y | G | . | S | . | . | . | . |
| DOM23h-348 | . | . | . | . | . | . | . | . | . | A | . | D | P | P | . | Q | H | . | H | . | . | . | . |
| DOM23h-435 | . | . | . | . | . | . | . | . | . | S | . | W | P | P | . | G | . | . | L | . | . | . | . |
| DOM23h-436 | . | . | . | . | . | . | . | . | . | A | . | D | S | S | . | H | . | . | T | . | . | . | . |
| DOM23h-437 | . | . | . | . | . | . | . | . | . | R | . | G | M | M | . | . | G | . | K | . | . | . | . |
| DOM23h-438 | . | . | . | . | . | . | . | . | . | R | . | D | S | S | . | G | . | . | R | . | . | . | . |
| DOM23h-439 | . | . | . | . | . | . | . | . | . | A | . | D | P | P | . | Q | Q | . | H | . | . | . | . |

Kabat positions ~62–79 (all DOM23h variants identical to reference, shown as "."):

| Kabat Residue | A | D | S | V | K(64) | G | R | F | T | I(69) | S | R | D | N | S(74) | N | K | T | L | Y(79) |
|---|---|---|---|---|---|---|---|---|---|---|---|---|---|---|---|---|---|---|---|---|
| DOM23h-251 | . | . | . | . | . | . | . | . | . | . | . | . | . | . | . | . | . | . | . | . |
| DOM23h-262 | . | . | . | . | . | . | . | . | . | . | . | . | . | . | . | . | . | . | . | . |
| DOM23h-271 | . | . | . | . | . | . | . | . | . | . | . | . | . | . | . | . | . | . | . | . |
| DOM23h-33  | . | . | . | . | . | . | . | . | . | . | . | . | . | . | . | . | . | . | . | . |
| DOM23h-348 | . | . | . | . | . | . | . | . | . | . | . | . | . | . | . | . | . | . | . | . |
| DOM23h-435 | . | . | . | . | . | . | . | . | . | . | . | . | . | . | . | . | . | . | . | . |
| DOM23h-436 | . | . | . | . | . | . | . | . | . | . | . | . | . | . | . | . | . | . | . | . |
| DOM23h-437 | . | . | . | . | . | . | . | . | . | . | . | . | . | . | . | . | . | . | . | . |
| DOM23h-438 | . | . | . | . | . | . | . | . | . | . | . | . | . | . | . | . | . | . | . | . |
| DOM23h-439 | . | . | . | . | . | . | . | . | . | . | . | . | . | . | . | . | . | . | . | . |
| DOM23h-440 | . | . | . | . | . | . | . | . | . | . | . | . | . | . | . | . | . | . | . | . |

FIGURE 2 (continued)

| Kabat Residue | L | Q | M | N | S | L | R | A | E | D | T | A | V | Y | Y | C | A | K | - | A | R | H | R | S | N | H | G | P | H | L |
|---|---|---|---|---|---|---|---|---|---|---|---|---|---|---|---|---|---|---|---|---|---|---|---|---|---|---|---|---|---|---|
| | | | | | 82b | | | | | 86 | | | | 91 | | | | | | 96 | | | | | | | | | | |
| DOM23h-251 | . | . | . | . | S | . | . | . | . | D | . | . | . | . | . | . | . | . | - | D | R | Q | H | R | H | · | Y | G | R | E |
| DOM23h-262 | . | . | . | . | . | . | . | . | . | . | . | . | . | . | . | . | . | . | - | K | . | . | . | . | . | . | . | . | . | . |
| DOM23h-271 | . | . | . | . | . | . | . | . | . | . | . | . | . | . | . | . | . | . | - | A | . | . | . | . | . | . | . | . | . | . |
| DOM23h-33 | . | . | . | . | . | . | . | . | . | . | . | . | . | . | . | . | . | . | - | C | . | . | . | . | . | . | . | . | . | . |
| DOM23h-348 | . | . | . | . | . | . | . | . | . | . | . | . | . | . | . | . | . | . | - | Y | . | . | . | . | . | . | . | . | . | . |
| DOM23h-435 | . | . | . | . | . | . | . | . | . | . | . | . | . | . | . | . | . | . | - | Y | . | . | . | . | . | . | . | . | . | . |
| DOM23h-436 | . | . | . | . | . | . | . | . | . | . | . | . | . | . | . | . | . | . | - | V | . | . | . | . | . | . | . | . | . | . |
| DOM23h-437 | . | . | . | . | . | . | . | . | . | . | . | . | . | . | . | . | . | . | - | A | . | . | . | . | . | . | . | . | . | . |
| DOM23h-438 | . | . | . | . | . | . | . | . | . | . | . | . | . | . | . | . | . | . | - | T | . | . | . | . | . | . | . | . | . | . |
| DOM23h-439 | . | . | . | . | . | . | . | . | . | . | . | . | . | . | . | . | . | . | - | R | . | . | . | . | . | . | . | . | . | . |
| DOM23h-440 | . | . | . | . | . | . | . | . | . | . | . | . | . | . | . | . | . | . | - | L | . | . | . | . | . | . | . | . | . | . |

| Kabat Residue | T | H | S | M | K | G | H | T | A | N | R | S | R | T | F | W | E | Y | Y | G | Q | G | T | L | V |
|---|---|---|---|---|---|---|---|---|---|---|---|---|---|---|---|---|---|---|---|---|---|---|---|---|---|
| | | | | | | 100a | | | | | 100f | | | | | 103 | | | | | | | | 108 | |
| DOM23h-251 | D | A | G | S | M | G | H | H | G | T | R | S | R | - | - | G | - | - | - | . | . | . | . | . | . |
| DOM23h-262 | P | G | F | H | V | W | T | A | N | A | R | - | - | F | R | . | D | Y | W | . | Q | G | T | L | V |
| DOM23h-271 | . | S | G | · | · | · | · | · | · | · | · | · | · | · | · | · | · | · | · | · | · | · | · | · | · |
| DOM23h-33 | W | D | M | G | S | H | A | · | Q | · | · | · | · | · | · | G | · | Y | W | G | Q | G | T | L | V |
| DOM23h-348 | S | G | F | F | S | A | · | · | · | · | · | · | · | · | · | G | · | Y | W | G | Q | G | T | L | V |
| DOM23h-435 | M | Y | F | T | Q | F | · | · | · | · | · | · | · | · | · | G | · | Y | W | G | Q | G | T | L | V |
| DOM23h-436 | G | S | F | G | P | G | E | · | Y | · | · | · | · | · | · | G | · | Y | W | G | Q | G | T | L | V |
| DOM23h-437 | A | A | L | · | S | · | · | · | · | · | · | · | · | · | · | G | · | Y | W | G | Q | G | T | L | V |
| DOM23h-438 | L | S | G | T | F | · | · | · | · | · | · | · | · | · | · | G | · | Y | W | G | Q | G | T | L | V |
| DOM23h-439 | · | · | · | · | · | · | · | · | · | · | · | · | · | · | · | · | · | · | · | · | · | · | · | · | · |
| DOM23h-440 | · | · | · | · | · | · | · | · | · | · | · | · | · | · | · | · | · | · | · | · | · | · | · | · | · |

FIGURE 2 (continued)

| Kabat Residue |   |   |   |   | 113 |
|---|---|---|---|---|---|
| DOM23h-251 | V | . | T | . | S |
| DOM23h-262 | . | T | . | V | S |
| DOM23h-271 | T | . | V | . | . |
| DOM23h-33  | . | . | . | . | . |
| DOM23h-348 | T | . | V | S | . |
| DOM23h-435 | T | T | V | S | . |
| DOM23h-436 | T | T | V | S | . |
| DOM23h-437 | T | T | V | S | . |
| DOM23h-438 | T | T | V | S | . |
| DOM23h-439 | T | T | V | S | . |
| DOM23h-440 | T | T | V | S | . |

FIGURE 3

| Position | Kabat Residue | DOM23h-262 | DOM23h-262-10 | DOM23h-262-6 |
|---|---|---|---|---|
| 1 | E | . | . | . |
| 2 | V | . | . | . |
| 3 | Q | . | . | . |
| 4 | L | . | . | . |
| 5 | L | . | . | . |
| 6 | E | . | . | . |
| 7 | S | . | . | . |
| 8 | G | . | . | . |
| 9 | G | . | . | . |
| 10 | G | . | . | . |
| 11 | L | . | . | . |
| 12 | V | . | . | . |
| 13 | Q | . | . | . |
| 14 | P | . | . | . |
| 15 | G | . | . | . |
| 16 | G | . | . | . |
| 17 | S | . | . | . |
| 18 | L | . | . | . |
| 19 | R | . | . | . |
| 20 | L | . | . | . |
| 21 | S | . | . | . |
| 22 | C | . | . | . |
| 23 | A | . | . | . |
| 24 | A | . | . | . |
| 25 | S | . | . | . |
| 26 | G | . | . | . |
| 27 | F | . | . | . |
| 28 | T | . | . | . |
| 29 | F | . | . | . |
| 30 | F | . | . | . |
| 31 | N | . | . | . |
| 32 | Y | . | . | . |
| 33 | E | . | . | . |
| 34 | M | . | . | . |
| 35 | A | . | . | . |
| 36 | W | . | . | . |
| 37 | A | . | . | . |
| 38 | R | . | . | . |
| 39 | Q | R | . | . |
| 40 | A | . | . | . |
| 41 | P | . | . | . |
| 42 | G | . | . | . |
| 43 | K | . | . | . |
| 44 | G | . | . | . |
| 45 | L | . | . | . |
| 46 | E | . | . | . |
| 47 | W | . | . | . |
| 48 | V | . | . | . |
| 49 | S | . | . | . |
| 50 | L | . | . | . |
| 51 | I | . | . | . |
| 52 | S | . | . | . |
| 53 | A | . | . | . |
| 54 | E | D | . | . |
| 55 | G | . | . | . |
| 56 | H | . | . | . |
| 57 | R | . | . | . |
| 58 | T | . | . | . |
| 59 | Y | . | . | . |
| 60 | Y | . | . | . |
| 61 | A | . | . | . |
| 62 | D | N | N | . |
| 63 | S | . | . | . |
| 64 | V | . | . | . |
| 65 | K | R | . | . |
| 66 | G | . | . | . |
| 67 | R | . | . | . |
| 68 | F | . | . | . |
| 69 | T | . | . | . |
| 70 | I | . | . | . |
| 71 | S | . | . | . |
| 72 | R | . | . | . |
| 73 | D | . | . | . |
| 74 | N | . | . | . |
| 75 | S | . | . | . |
| 76 | K | . | . | . |
| 77 | N | . | . | . |
| 78 | T | . | . | . |
| 79 | L | . | . | . |
| 80 | Y | . | . | . |

FIGURE 3 (continued)

| Kabat Residue | L | Q | M | N | 82b S | L | R | A | E | 86 D | T | A | V | Y | 91 Y | C | A | K | R | 96 R | | |
|---|---|---|---|---|---|---|---|---|---|---|---|---|---|---|---|---|---|---|---|---|---|---|
| DOM23h-262 | | | | | | | | | | | | | | | | | | | | | | |
| DOM23h-262-10 | | | | | | | | | | | | | | | | | | | | · | · | |
| DOM23h-262-6 | | | | | | | | | | | | | | | | | | | | · | · | |

| Kabat Residue | D | A | S | M | 100a G | H | H | H | R | 100f F | F | D | Y | W | 104 G | Q | G | T | L | 109 V | | |
|---|---|---|---|---|---|---|---|---|---|---|---|---|---|---|---|---|---|---|---|---|---|---|
| DOM23h-262 | | | | | | | | | | | | | | | | | | | | | | |
| DOM23h-262-10 | · | · | · | · | · | · | · | · | · | · | · | · | · | · | | | | | | · | · | |
| DOM23h-262-6 | · | · | · | · | · | · | · | · | · | · | · | · | · | · | | | | | | · | · | |

| Kabat Residue | T | V | S | S |
|---|---|---|---|---|
| DOM23h-262 | | | | |
| DOM23h-262-10 | | | | |
| DOM23h-262-6 | | | | |

FIGURE 4

| Kabat Residue | 5 | | | | | 10 | | | | | 15 | | | | | 20 |
|---|---|---|---|---|---|---|---|---|---|---|---|---|---|---|---|---|
| DOM23h-271 | E | V | Q | L | E | G | G | G | S | L | G | P | Q | V | L | L |
| DOM23h-271-12 | . | . | . | . | . | . | . | . | . | . | . | . | . | . | . | . |
| DOM23h-271-13 | . | . | . | . | . | . | . | . | . | . | . | . | . | . | . | . |
| DOM23h-271-3 | . | . | . | . | . | . | . | . | . | . | . | . | . | . | . | . |
| DOM23h-271-7 | . | . | . | . | . | . | . | . | . | . | . | . | . | . | . | . |

| Kabat Residue | | | | | 25 | | | | | 30 | | | | | 35 | | | | | 40 |
|---|---|---|---|---|---|---|---|---|---|---|---|---|---|---|---|---|---|---|---|---|
| DOM23h-271 | S | C | A | A | S | G | F | T | F | T | E | L | Y | R | M | W | V | R | Q | A |
| DOM23h-271-12 | . | . | T | . | . | . | . | . | . | . | . | . | . | . | . | . | . | . | . | . |
| DOM23h-271-13 | . | . | . | T | . | . | . | . | . | . | . | . | . | . | . | . | . | . | . | . |
| DOM23h-271-3 | . | . | . | . | . | . | . | . | . | . | . | . | . | . | . | . | . | . | . | . |
| DOM23h-271-7 | . | . | . | . | . | . | . | . | . | . | . | . | . | . | . | . | . | . | . | . |

| Kabat Residue | | | 45 | | | | | 50 | | | | | | | | | | 54 | | | 59 |
|---|---|---|---|---|---|---|---|---|---|---|---|---|---|---|---|---|---|---|---|---|---|
| DOM23h-271 | P | G | K | G | L | E | W | V | S | A | L | A | L | A | S | H | E | P | H | I | N | G | R | N | T | H | Y | Y |
| DOM23h-271-12 | . | . | . | . | . | . | . | . | L | . | L | . | L | . | . | . | . | . | . | . | . | . | . | . | . | . | . | . |
| DOM23h-271-13 | . | . | . | . | . | . | . | . | A | . | A | . | A | . | . | . | . | . | . | . | . | . | . | . | . | . | . | . |
| DOM23h-271-3 | . | . | . | . | . | . | . | . | . | . | . | . | . | . | . | . | . | . | . | . | . | . | . | . | . | . | . | . |
| DOM23h-271-7 | . | . | . | . | . | . | . | . | . | . | . | . | . | . | . | . | . | . | . | . | . | . | . | . | . | . | . | . |

| Kabat Residue | | | | 64 | | | | | 69 | | | | | | | | | 74 | | | 79 |
|---|---|---|---|---|---|---|---|---|---|---|---|---|---|---|---|---|---|---|---|---|---|
| DOM23h-271 | A | D | N | K | V | S | G | R | I | T | S | R | D | N | S | K | N | T | L | Y |
| DOM23h-271-12 | . | . | . | R | . | . | . | . | . | . | . | . | . | . | . | . | . | . | . | . |
| DOM23h-271-13 | . | . | . | R | . | . | . | . | . | . | . | . | . | . | . | . | . | . | . | . |
| DOM23h-271-3 | . | . | . | . | . | . | . | . | . | . | . | . | . | . | . | . | . | . | . | . |
| DOM23h-271-7 | . | . | . | . | . | . | . | . | . | . | . | . | . | . | . | . | . | . | . | . |

| Kabat Residue | 82b | | | | | 86 | | | | | 91 | | | | | 96 |
|---|---|---|---|---|---|---|---|---|---|---|---|---|---|---|---|---|
| DOM23h-271 | S | L | R | A | E | D | T | A | V | Y | Y | C | A | K | Q | H |
| DOM23h-271-12 | . | . | . | . | . | . | . | . | . | . | . | . | . | . | . | . |
| DOM23h-271-13 | . | . | . | . | . | . | . | . | . | . | . | . | . | . | . | . |
| DOM23h-271-3 | . | . | . | . | . | . | . | . | . | . | . | . | . | . | . | . |
| DOM23h-271-7 | . | . | . | . | . | . | . | . | . | . | . | . | . | . | . | . |

FIGURE 4 (continued)

| Kabat Residue | - | - | - | - | 100a' | - | - | - | - | - | 100f' | - | - | - | 103 | - | - | - | - | 108 |
|---|---|---|---|---|---|---|---|---|---|---|---|---|---|---|---|---|---|---|---|---|
| DOM23h-271 | P | G | H | K | W | T | A | N | S | R | F | D | Y | W | G | Q | G | T | L | V |
| DOM23h-271-12 | . | . | R | M | . | . | . | . | P | . | S | . | . | . | . | . | . | . | . | . |
| DOM23h-271-13 | . | . | . | . | . | . | . | . | . | . | . | . | . | . | . | . | . | . | . | . |
| DOM23h-271-3 | . | . | R | M | . | . | . | . | P | . | S | . | . | . | . | . | . | . | . | . |
| DOM23h-271-7 | . | . | . | . | . | . | . | . | . | . | . | . | . | . | . | . | . | . | . | . |

| Kabat Residue | - | - | - | - |
|---|---|---|---|---|
| DOM23h-271 | T | V | . | . |
| DOM23h-271-12 | S | S | . | . |
| DOM23h-271-13 | S | S | . | . |
| DOM23h-271-3 | . | . | . | . |
| DOM23h-271-7 | . | . | . | . |

FIGURE 5

| Kabat Residue | | | | | 5 | | | | | 10 | | | | | 15 | | | | | 20 |
|---|---|---|---|---|---|---|---|---|---|---|---|---|---|---|---|---|---|---|---|---|
| DOM23h-437 | E | V | Q | L | L | E | S | G | G | G | L | V | Q | P | G | G | S | L | R | L |
| DOM23h-437-4 | . | . | . | . | . | . | . | . | . | . | . | . | . | . | . | . | . | . | . | . |
| DOM23h-437-6 | . | . | . | . | . | . | . | . | . | . | . | . | . | . | . | . | . | . | . | . |
| DOM23h-437-8 | . | . | . | . | . | . | . | . | . | . | . | . | . | . | . | . | . | . | . | . |
| DOM23h-437-9 | . | . | . | . | . | . | . | . | . | . | . | . | . | . | . | . | . | . | . | . |

| Kabat Residue | | | | | 25 | | | | | 30 | | | | | 35 | | | | | 40 |
|---|---|---|---|---|---|---|---|---|---|---|---|---|---|---|---|---|---|---|---|---|
| DOM23h-437 | S | C | A | A | S | G | F | T | F | S | D | Y | R | M | W | H | V | R | Q | A |
| DOM23h-437-4 | . | . | . | T | . | . | . | . | I | . | . | . | . | . | . | . | . | . | . | . |
| DOM23h-437-6 | . | . | . | . | . | . | . | . | . | . | . | . | . | . | . | . | . | . | . | . |
| DOM23h-437-8 | . | . | . | T | . | . | . | . | I | . | . | . | . | . | . | . | . | . | . | . |
| DOM23h-437-9 | . | . | . | . | . | . | . | . | . | . | . | . | . | . | . | . | . | . | . | . |

| Kabat Residue | | | | | 45 | | | | | 50 | | | | | 54 | | | | | 59 |
|---|---|---|---|---|---|---|---|---|---|---|---|---|---|---|---|---|---|---|---|---|
| DOM23h-437 | P | G | K | G | L | E | W | V | S | A | H | D | S | Q | G | H | I | I | Y | Y |
| DOM23h-437-4 | . | . | . | . | . | . | . | . | . | . | . | . | . | . | . | . | . | . | . | . |
| DOM23h-437-6 | . | . | . | . | . | . | . | . | . | . | . | . | . | . | . | . | . | . | . | . |
| DOM23h-437-8 | . | . | . | . | . | . | . | . | . | . | . | . | . | . | . | . | . | . | . | . |
| DOM23h-437-9 | . | . | . | . | . | . | . | . | . | . | . | . | . | . | . | . | . | . | . | . |

| Kabat Residue | | | | | 64 | | | | | 69 | | | | | 74 | | | | | 79 |
|---|---|---|---|---|---|---|---|---|---|---|---|---|---|---|---|---|---|---|---|---|
| DOM23h-437 | A | D | S | V | K | G | R | F | T | I | S | R | D | N | S | K | N | T | L | Y |
| DOM23h-437-4 | . | N | . | . | R | . | . | . | . | . | . | . | . | . | . | . | . | . | . | . |
| DOM23h-437-6 | . | N | . | . | R | . | . | . | . | . | . | . | . | . | . | . | . | . | . | . |
| DOM23h-437-8 | . | . | . | . | R | . | . | . | . | . | . | . | . | . | . | . | . | . | . | . |
| DOM23h-437-9 | . | . | . | . | R | . | . | . | . | . | . | . | . | . | . | . | . | . | . | . |

| Kabat Residue | | | | | 82b | | | | | 86 | | | | | 91 | | | | | 96 |
|---|---|---|---|---|---|---|---|---|---|---|---|---|---|---|---|---|---|---|---|---|
| DOM23h-437 | L | Q | M | N | S | L | R | A | E | D | T | A | V | Y | Y | C | A | K | Y | G |
| DOM23h-437-4 | . | . | . | . | . | . | . | . | . | . | . | . | . | . | . | . | . | . | . | . |
| DOM23h-437-6 | . | . | . | . | . | . | . | . | . | . | . | . | . | . | . | . | . | . | . | . |
| DOM23h-437-8 | . | . | . | . | . | . | . | . | . | . | . | . | . | . | . | . | . | . | . | . |
| DOM23h-437-9 | . | . | . | . | . | . | . | . | . | . | . | . | . | . | . | . | . | . | . | . |

FIGURE 5 (continued)

| Kabat Residue | G | Y | F | D | Y | W | G | Q | G | T | L | V | T | V | S | S |
|---|---|---|---|---|---|---|---|---|---|---|---|---|---|---|---|---|
| | | | | | | 101 | | | | 106 | | | | | | 111 |
| DOM23h-437 | G | Y | F | D | Y | W | G | Q | G | T | L | V | T | V | S | S |
| DOM23h-437-4 | . | . | . | . | . | . | . | . | . | . | . | . | . | . | . | . |
| DOM23h-437-6 | . | . | . | . | . | . | . | . | . | . | . | . | . | . | . | . |
| DOM23h-437-8 | . | . | . | . | . | . | . | . | . | . | . | . | . | . | . | . |
| DOM23h-437-9 | . | . | . | . | . | . | . | . | . | . | . | . | . | . | . | . |

FIGURE 6

Block 1 (residues 1–20):

| Kabat Residue | | | | | 5 | | | | | 10 | | | | | 15 | | | | | 20 |
|---|---|---|---|---|---|---|---|---|---|---|---|---|---|---|---|---|---|---|---|---|
| DOM23h-439   | E | V | Q | L | L | E | S | G | G | G | L | V | Q | R | P | G | S | L | R | L |
| DOM23h-439-6 | · | · | · | · | · | · | · | · | · | · | · | · | R | · | · | · | · | · | · | · |
| DOM23h-439-8 | · | · | · | · | · | · | · | · | · | · | · | · | R | · | · | · | · | · | · | · |

Block 2 (residues 21–40):

| Kabat Residue | | | | | 25 | | | | | 30 | | | | | 35 | | | | | 40 |
|---|---|---|---|---|---|---|---|---|---|---|---|---|---|---|---|---|---|---|---|---|
| DOM23h-439   | S | C | A | A | S | G | F | T | F | G | T | E | Q | M | W | W | V | R | Q | A |
| DOM23h-439-6 | · | · | · | · | · | · | · | · | · | · | · | · | · | · | · | · | · | · | · | · |
| DOM23h-439-8 | · | · | · | · | · | · | · | · | · | · | · | · | · | · | · | · | · | · | · | · |

Block 3 (residues 41–59):

| Kabat Residue | | | | | 45 | | | | | 50 | | | | | 54 | | | | 59 |
|---|---|---|---|---|---|---|---|---|---|---|---|---|---|---|---|---|---|---|---|
| DOM23h-439   | P | G | K | G | L | E | W | V | S | R | H | D | I | S | G | P | R | T | Y |
| DOM23h-439-6 | · | · | · | · | · | · | · | · | · | · | · | · | · | · | · | · | · | · | · |
| DOM23h-439-8 | · | · | · | · | · | · | · | · | · | · | · | · | · | · | · | · | · | · | · |

(Position 59: Y)

Block 4 (residues 60–79):

| Kabat Residue | | | | | 64 | | | | | 69 | | | | | 74 | | | | | 79 |
|---|---|---|---|---|---|---|---|---|---|---|---|---|---|---|---|---|---|---|---|---|
| DOM23h-439   | A | D | S | V | K | G | R | F | T | I | S | R | D | N | K | N | A | T | L | Y |
| DOM23h-439-6 | · | · | · | · | R | · | · | · | · | · | · | · | · | · | · | · | · | · | · | · |
| DOM23h-439-8 | · | · | · | · | R | · | · | · | · | · | · | · | · | · | · | · | · | · | · | · |

Block 5 (residues 80–96):

| Kabat Residue | | 82b | | | | 86 | | | | | 91 | | | | | 96 |
|---|---|---|---|---|---|---|---|---|---|---|---|---|---|---|---|---|
| DOM23h-439   | L | S | N | M | Q | L | R | A | E | D | T | A | V | Y | Y | C | A | K | R | H |
| DOM23h-439-6 | · | · | · | · | · | · | · | · | · | · | · | · | · | · | · | · | · | · | · | R |
| DOM23h-439-8 | · | · | · | · | · | · | · | · | · | · | · | · | · | · | · | · | · | · | · | R |

FIGURE 6 (continued)

```
                                     100a'          1000'              105           110
Kabat Residue    A  A  G  V  S  G  T  Y  F  D  Y  W  G  Q  G  T  L  V  T  V
DOM23h-439       -  -  -  -  -  -  -  -  -  -  -  -  -  -  -  -  -  -  -  -
DOM23h-439-6     .  .  .  .  .  .  .  .  .  .  .  .  .  .  .  .  .  .  .  .
DOM23h-439-8     .  .  .  .  .  .  .  .  .  .  .  .  .  .  .  .  .  .  .  .

Kabat Residue    
DOM23h-439       S  S  .  .
DOM23h-439-6        S  .  .
DOM23h-439-8
```

FIGURE 7

| dAb | CDR1 | CDR2 | CDR3 |
|---|---|---|---|
| DOM23h-33 | QYRMW (SEQ ID NO: 55) | AIAPSGDNTYYADSVKG (SEQ ID NO: 56) | HRTSFDY (SEQ ID NO: 57) |
| DOM23h-251 | DYDMW (SEQ ID NO: 58) | KITQKGDFTYYADSVKG (SEQ ID NO: 59) | DATHFDY (SEQ ID NO: 60) |
| DOM23h-262 | NYEMA (SEQ ID NO: 61) | LISAEGTRTYYADSVKG (SEQ ID NO: 62) | RRDASMGHTTRRFDY (SEQ ID NO: 63) |
| DOM23h-271 | EYRMW (SEQ ID NO: 64) | SIEPIGNRTYYADSVKG (SEQ ID NO: 65) | QIPGHKWTANSRFDY (SEQ ID NO: 66) |
| DOM23h-348 | DYDMA (SEQ ID NO: 67) | RISHSGYSTYYADSVKG (SEQ ID NO: 68) | RSWDGVHAQFDYW (SEQ ID NO: 69) |
| DOM23h-435 | DDRMW (SEQ ID NO: 70) | AIDPQGQHTYYADSVKG (SEQ ID NO: 71) | HNSSFDYW (SEQ ID NO: 72) |
| DOM23h-436 | DYKMG (SEQ ID NO: 73) | SIWPNGGLTYYADSVKG (SEQ ID NO: 74) | DHMGFDYW (SEQ ID NO: 75) |
| DOM23h-437 | DYRMW (SEQ ID NO: 76) | AIDSQGHTTYYADSVKG (SEQ ID NO: 77) | YGGYFDYW (SEQ ID NO: 78) |
| DOM23h-438 | QGDMW (SEQ ID NO: 79) | RIGMDGDKTYYADSVKG (SEQ ID NO: 80) | GPSSTSPFDY (SEQ ID NO: 81) |
| DOM23h-439 | TEQMW (SEQ ID NO: 82) | RIDSPGGRTYYADSVKG (SEQ ID NO: 83) | RHAAGVSGTYFDY (SEQ ID NO: 84) |
| DOM23h-440 | DDRMW (SEQ ID NO: 85) | AIDPQGQHTYYADSVKG (SEQ ID NO: 86) | ELLSFDYW (SEQ ID NO: 87) |
| DOM23h-262-6 | NYEMAW (SEQ ID NO: 88) | LISAEGTRTYYANSVKG (SEQ ID NO: 89) | RRDASMGHTTRRFDH (SEQ ID NO: 90) |
| DOM23h-262-10 | FNYEMA (SEQ ID NO: 91) | LISADGTRTYYANSVRG (SEQ ID NO: 92) | RRDASMGHTTRRFDY (SEQ ID NO: 93) |
| DOM23h-271-3 | EYRMW (SEQ ID NO: 94) | LIEPIGNRTYYADSVKG (SEQ ID NO: 95) | QIPGHMWTANPRSDY (SEQ ID NO: 96) |
| DOM23h-271-7 | EYRMW (SEQ ID NO: 97) | AIEPIGNRTYYADSVKG (SEQ ID NO: 98) | QIPGRKWTANSRFDY (SEQ ID NO: 99) |
| DOM23h-271-12 | EYRMW (SEQ ID NO: 100) | LIEPIGNRTYYANSVRG (SEQ ID NO: 101) | QIPGHMWTANPRSDY (SEQ ID NO: 102) |
| DOM23h-271-13 | EYRMW (SEQ ID NO: 103) | AIEPIGNRTYYANSVRG (SEQ ID NO: 104) | QIPGRKWTANSRFDY (SEQ ID NO: 105) |

FIGURE 7 Continued

| DOM23h-437-4 | DYRMW (SEQ ID NO: 106) | AIDSQGHTTYYADSVRG (SEQ ID NO: 107) | YGGYFDY (SEQ ID NO: 108) |
|---|---|---|---|
| DOM23h-437-6 | DYRMW (SEQ ID NO: 109) | AIDSQGHTTYYADSVKG (SEQ ID NO: 110) | YGGYFDY (SEQ ID NO: 111) |
| DOM23h-437-8 | DYRMW (SEQ ID NO: 112) | AIDSQGHTTYYANSVRG (SEQ ID NO: 113) | YGGYFDY (SEQ ID NO: 114) |
| DOM23h-437-9 | SDYRM (SEQ ID NO: 115) | AIDSQGHTTYYANSVRG (SEQ ID NO: 116) | YGGYFDY (SEQ ID NO: 117) |
| DOM23h-439-6 | TEQMW (SEQ ID NO: 118) | RIDSPGGRTYYADSVRG (SEQ ID NO: 119) | RHAAGVSGTYFDY (SEQ ID NO: 120) |
| DOM23h-439-8 | TEQMW (SEQ ID NO: 121) | RIDSPGGRTYYANSVRG (SEQ ID NO: 122) | RHAAGVSGTYFDY (SEQ ID NO: 123) |

FIGURE 8
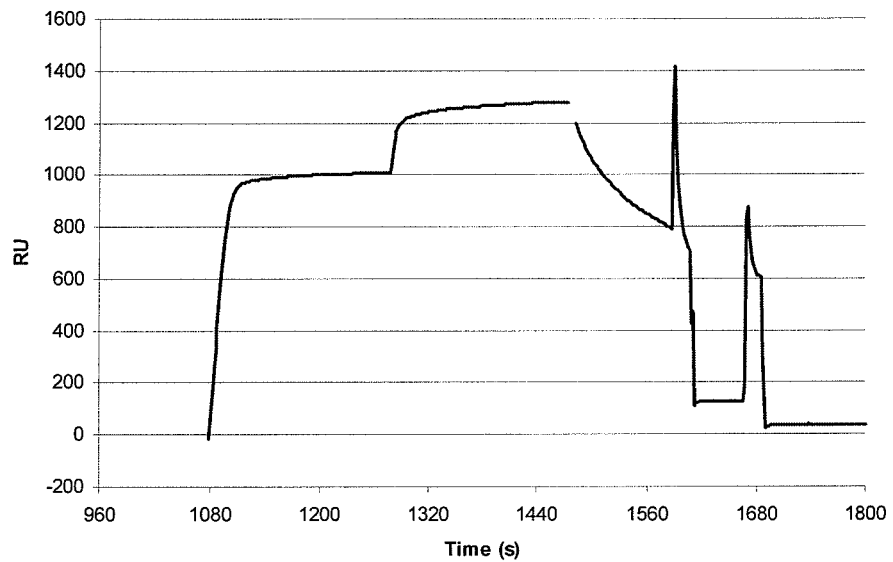
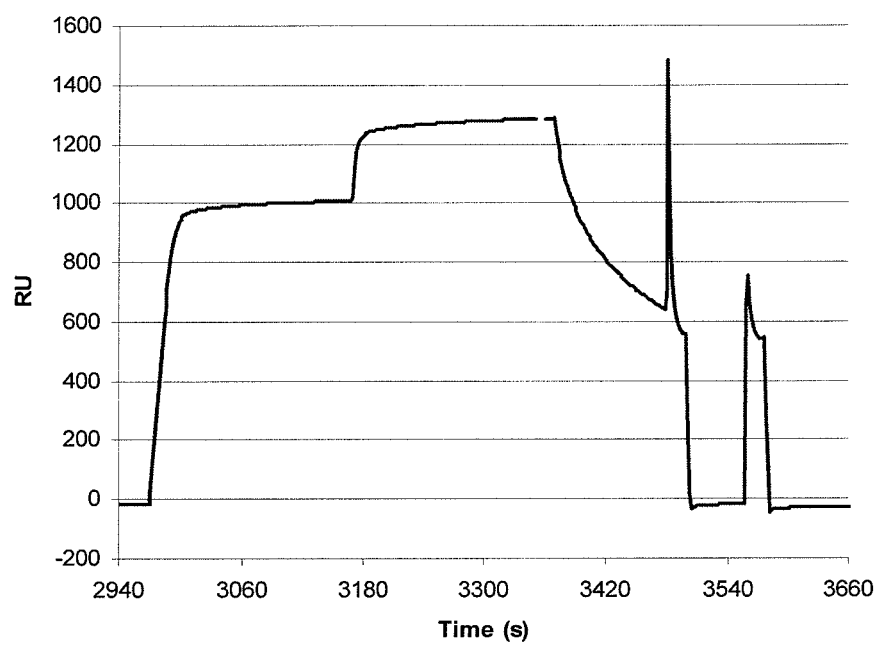

FIGURE 9
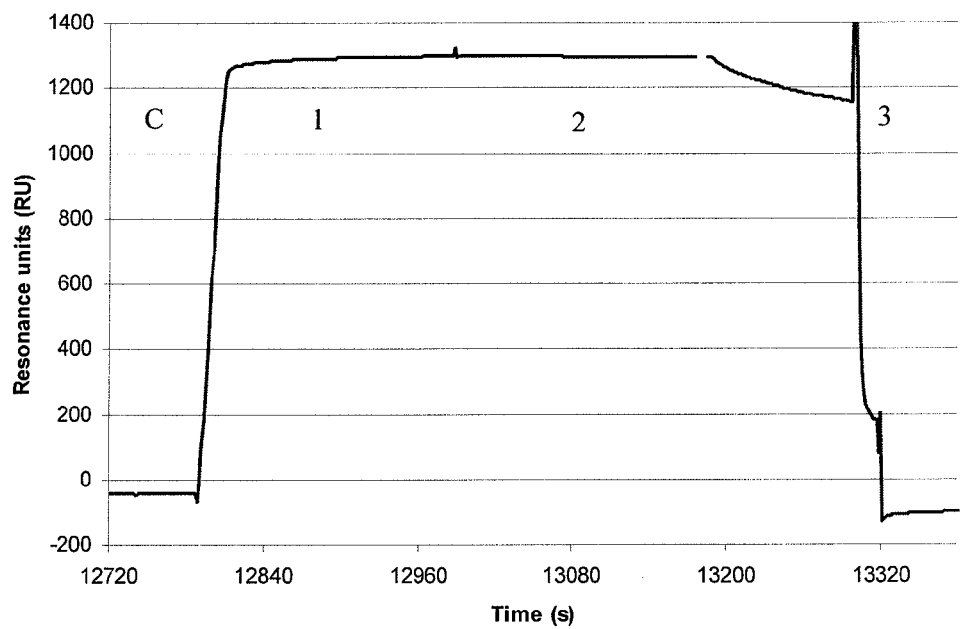
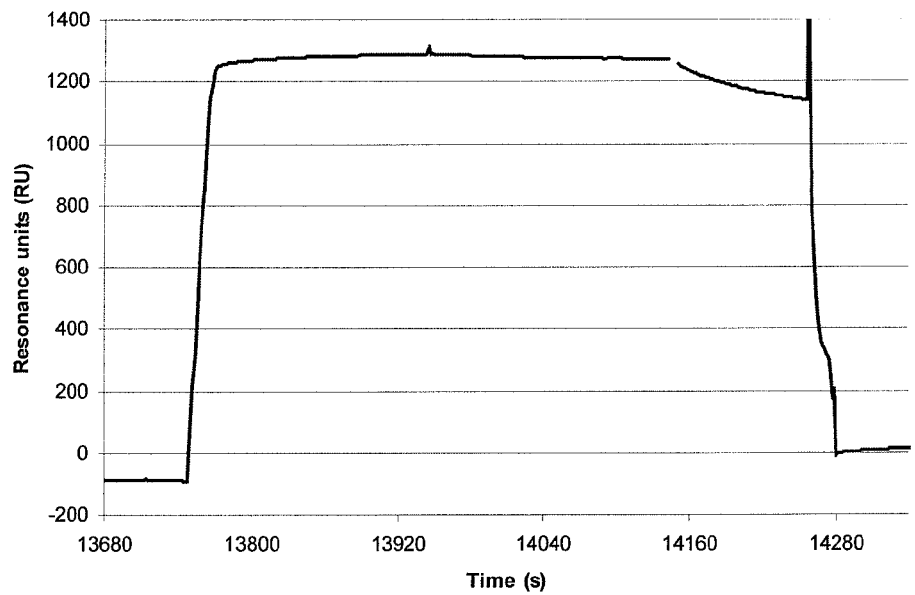

FIGURE 11

| SEQ ID NO: | Identification |
|---|---|
| 1 | DOM23h-33 (amino acid) |
| 2 | DOM23h-251 (amino acid) |
| 3 | DOM23h-262 (amino acid) |
| 4 | DOM23h-271 (amino acid) |
| 5 | DOM23h-348 (amino acid) |
| 6 | DOM23h-435 (amino acid) |
| 7 | DOM23h-436 (amino acid) |
| 8 | DOM23h-437 (amino acid) |
| 9 | DOM23h-438 (amino acid) |
| 10 | DOM23h-439 (amino acid) |
| 11 | DOM23h-440 (amino acid) |
| 12 | DOM23h-262-6 (amino acid) |
| 13 | DOM23h-262-10 (amino acid) |
| 14 | DOM23h-271-3 (amino acid) |
| 15 | DOM23h-271-7 (amino acid) |
| 16 | DOM23h-271-12 (amino acid) |
| 17 | DOM23h-271-13 (amino acid) |
| 18 | DOM23h-437-4 (amino acid) |
| 19 | DOM23h-437-6 (amino acid) |
| 20 | DOM23h-437-8 (amino acid) |
| 21 | DOM23h-437-9 (amino acid) |
| 22 | DOM23h-439-6 (amino acid) |
| 23 | DOM23h-439-8 (amino acid) |
| 24 | DOM23h-33 (nucleic acid) |
| 25 | DOM23h-251 (nucleic acid) |
| 26 | DOM23h-262 (nucleic acid) |
| 27 | DOM23h-271 (nucleic acid) |
| 28 | DOM23h-348 (nucleic acid) |
| 29 | DOM23h-435 (nucleic acid) |
| 30 | DOM23h-436 (nucleic acid) |
| 31 | DOM23h-437 (nucleic acid) |
| 32 | DOM23h-438 (nucleic acid) |
| 33 | DOM23h-439 (nucleic acid) |
| 34 | DOM23h-440 (nucleic acid) |
| 35 | DOM23h-262-6 (nucleic acid) |
| 36 | DOM23h-262-10 (nucleic acid) |
| 37 | DOM23h-271-3 (nucleic acid) |
| 38 | DOM23h-271-7 (nucleic acid) |
| 39 | DOM23h-271-12 (nucleic acid) |
| 40 | DOM23h-271-13 (nucleic acid) |
| 41 | DOM23h-437-4 (nucleic acid) |

FIGURE 11 (continued)

| SEQ ID NO: | Identification |
|---|---|
| 42 | DOM23h-437-6 (nucleic acid) |
| 43 | DOM23h-437-8 (nucleic acid) |
| 44 | DOM23h-437-9 (nucleic acid) |
| 45 | DOM23h-439-6 (nucleic acid) |
| 46 | DOM23h-439-8 (nucleic acid) |
| 47 | DOM57 |
| 48 | DOM6 |
| 49 | DOM0008 |
| 50 | DOM0009 |
| 51 | DOM172 |
| 52 | DOM173 |
| 53 | CD131 |
| 54 | CD130 |
| 55 | DOM23h-33 CDR1 |
| 56 | DOM23h-33 CDR2 |
| 57 | DOM23h-33 CDR3 |
| 58 | DOM23h-251 CDR1 |
| 59 | DOM23h-251 CDR2 |
| 60 | DOM23h-251 CDR3 |
| 61 | DOM23h-262 CDR1 |
| 62 | DOM23h-262 CDR2 |
| 63 | DOM23h-262 CDR3 |
| 64 | DOM23h-271 CDR1 |
| 65 | DOM23h-271 CDR2 |
| 66 | DOM23h-271 CDR3 |
| 67 | DOM23h-348 CDR1 |
| 68 | DOM23h-348 CDR2 |
| 69 | DOM23h-348 CDR3 |
| 70 | DOM23h-435 CDR1 |
| 71 | DOM23h-435 CDR2 |
| 72 | DOM23h-435 CDR3 |
| 73 | DOM23h-436 CDR1 |
| 74 | DOM23h-436 CDR2 |
| 75 | DOM23h-436 CDR3 |
| 76 | DOM23h-437 CDR1 |
| 77 | DOM23h-437 CDR2 |
| 78 | DOM23h-437 CDR3 |
| 79 | DOM23h-438 CDR1 |
| 80 | DOM23h-438 CDR2 |
| 81 | DOM23h-438 CDR3 |
| 82 | DOM23h-439 CDR1 |
| 83 | DOM23h-439 CDR2 |

FIGURE 11 (continued)

| 84 | DOM23h-439 CDR3 |
|---|---|
| 85 | DOM23h-440 CDR1 |
| 86 | DOM23h-440 CDR2 |
| 87 | DOM23h-440 CDR3 |
| 88 | DOM23h-262-6 CDR1 |
| 89 | DOM23h-262-6 CDR2 |
| 90 | DOM23h-262-6 CDR3 |
| 91 | DOM23h-262-10 CDR1 |
| 92 | DOM23h-262-10 CDR2 |
| 93 | DOM23h-262-10 CDR3 |
| 94 | DOM23h-271-3 CDR1 |
| 95 | DOM23h-271-3 CDR2 |
| 96 | DOM23h-271-3 CDR3 |
| 97 | DOM23h-271-7 CDR1 |
| 98 | DOM23h-271-7 CDR2 |
| 99 | DOM23h-271-7 CDR3 |
| 100 | DOM23h-271-12 CDR1 |
| 101 | DOM23h-271-12 CDR2 |
| 102 | DOM23h-271-12 CDR3 |
| 103 | DOM23h-271-13 CDR1 |
| 104 | DOM23h-271-13 CDR2 |
| 105 | DOM23h-271-13 CDR3 |
| 106 | DOM23h-437-4 CDR1 |
| 107 | DOM23h-437-4 CDR2 |
| 108 | DOM23h-437-4 CDR3 |
| 109 | DOM23h-437-6 CDR1 |
| 110 | DOM23h-437-6 CDR2 |
| 111 | DOM23h-437-6 CDR3 |
| 112 | DOM23h-437-8 CDR1 |
| 113 | DOM23h-437-8 CDR2 |
| 114 | DOM23h-437-8 CDR3 |
| 115 | DOM23h-437-9 CDR1 |
| 116 | DOM23h-437-9 CDR2 |
| 117 | DOM23h-437-9 CDR3 |
| 118 | DOM23h-439-6 CDR1 |
| 119 | DOM23h-439-6 CDR2 |
| 120 | DOM23h-439-6 CDR3 |
| 121 | DOM23h-439-8 CDR1 |
| 122 | DOM23h-439-8 CDR2 |
| 123 | DOM23h-439-8 CDR3 |

LIGANDS THAT BIND TGF-β RECEPTOR RII

This application is the non-provisional US National Stage application of International Application No. PCT/EP2010/060867, filed Jul. 27, 2010 and published in English which claims priority under 35 USC §119 or 35 USC §365 to US Provisional Patent Application Ser. No. 61/229,334 filed Jul. 29, 2009. The entire teachings of the above applications are incorporated herein by reference.

BACKGROUND OF THE DISCLOSURE

Transforming Growth Factor-β (TFGbeta; TGFβ (TGF-β)) is a signaling molecule that mediates signal transduction into cells through binding to a TGFbeta receptor (TGFbetaR; TGFβR (TGF-βR)). TGFbeta signaling activity regulates cell differentiation and growth, the nature of its effect, i.e. as cell growth-promoter, growth-suppressor or inducer of other cell functions, being dependent on cell type (see Roberts, et al., The transforming growth factor-betas, Peptide Growth Factors and Their Receptors, Part I, ed. by Sporn, M. B. & Roberts, A. B., Springer-Verlag, Berlin, 1990, p. 419-472).

TGFbeta is produced by a wide variety of cell types, and its cognate receptors are expressed in a wide variety of organs and cells (see Shi and Massague, Cell, Volume 113, Issue 6, 13 Jun. 2003, Pages 685-700; Biol. Signals., Vol. 5, p. 232, 1996 and Pulmonary Fibrosis, Vol. 80 of Lung Biology in Health and Disease Series, ed. by Phan, et al., p. 627, Dekker, New York, 1995). TGFbeta receptors have been identified to fall into three types: TGFbetaRI (TGFβRI) (TGFbeta type I receptor (Franzen et al., Cell, Vol. 75, No. 4, p. 681, 1993; GenBank Accession No: L11695)); TGFbetaRII (TGFβRII) (TGFbeta type II receptor (Herbert et al., Cell, Vol. 68, No. 4, p. 775, 1992; GenBank Accession No: M85079)) and TGFbetaRIII (TGFbeta type III receptor (Lopez-Casillas, Cell, Vol. 67, No. 4, p. 785, 1991; GenBank Accession No: L07594)). TGFbetaRI and TGFbetaRII have been shown to be essential for the signal transduction of TGF-beta (Laiho et al., J. Biol. Chem., Vol. 265, p. 18518, 1990 and Laiho et al., J. Biol. Chem., Vol. 266, p. 9108, 1991), while TGFbetaRIII is not thought to be essential.

TGFbeta signaling is mediated through its binding to both TGFbetaRI and RII. When the ligand binds to the extracellular ligand binding domain, the two receptors are brought together, allowing RII to phosphorylate RI and begin the signaling cascade through the phosphorylation of Smad proteins (see Shi and Massague as referred to above).

Three isoforms of TGFbeta have been identified in mammals: TGFbeta1, TGFbeta2, and TGFbeta3. Each isoform is multifunctional and acts in self-regulatory feedback mechanisms to control bioavailability for developmental processes and to maintain tissue homeostasis (as reviewed in ten Dijke and Arthur, Nature Reviews, Molecular Cell Biology, Vol. 8, November 2007, p. 857-869). Levels of TFGbeta are controlled by regulation through TGFbeta expression as well as through binding to proteoglycan, i.e., the extracellular matrix (ECM).

Dysregulated TGFbeta signaling, such as excess TGFbeta signaling and high levels of bioavailable TGFbeta, is implicated in a number of pathologies, including fibroses of various tissues, such as pulmonary fibrosis and cirrhosis, chronic hepatitis, rheumatoid arthritis, ocular disorders, vascular restenosis, keloid of skin, and the onset of nephrosclerosis.

Accordingly, there is a need to provide compounds that block or disrupt TGFbeta signaling in a specific manner, such as through binding to the TGFbeta receptor II. Such compounds can be used in therapeutics.

SUMMARY OF THE DISCLOSURE

In a first aspect, the disclosure provides an anti-TGFbetaRII immunoglobulin single variable domain. Suitably, an anti-TGFbetaRII immunoglobulin single variable domain in accordance with the first aspect is one which binds to TGFbetaRII with a dissociation constant (Kd) in the range of 10 pM to 50 nM, preferably 10 pM to 10 nM, preferably 250 pM to 10 nM. In one embodiment, the anti-TGFbetaRII immunoglobulin single variable domain is one which binds TGFbetaRII with high affinity (high potency) and has a dissociation constant of 10 pM to 500 pM. In another embodiment, the anti-TGFbetaRII immunoglobulin single variable domain is one which binds TGFbetaRII with moderate affinity (low potency) and has a dissociation constant of 500 pM to 50 nM, preferably 500 pM to 10 nM. In another aspect, the disclosure provides an isolated polypeptide comprising an anti-TGFbetaRII immunoglobulin single variable domain. Suitably, the isolated polypeptide comprises an amino acid sequence that is at least 70% identical to at least one amino acid sequence selected from the group of any of the amino acid sequences set out in SEQ ID NOs: 1 to 23 and which binds to TGFbetaRII. Suitably, the isolated polypeptide binds to human TGFbetaRII. In another embodiment, the isolated polypeptide also binds to TGFbetaRII derived from a different species such as mouse, dog or monkeys, such as cynomolgus monkeys (cyno). Suitably, the isolated polypeptide binds to both mouse and human TGFbetaRII. Such cross reactivity between TGFbetaRII from humans and other species allows the same antibody construct to be used in an animal disease model, as well as in humans.

In one aspect, the disclosure provides an isolated polypeptide comprising an amino acid sequence selected from the group of the amino acid sequences set out in SEQ ID NOs: 1 to 23. In one embodiment, the disclosure provides an isolated polypeptide comprising an amino acid sequence as set out in any of SEQ ID NOs: 4 (DOM23h-271), 8 (DOM23h-437) or 10 (DOM23h-439).

In another aspect, the disclosure provides an isolated polypeptide encoded by a nucleotide sequence that is at least 60% identical to the nucleotide sequence selected from the group of any of the nucleic acid sequences set out in SEQ ID NOS: 24 to 46 and which binds to TGFbetaRII. Suitably, the isolated polypeptide binds to human TGFbetaRII In another aspect, there is provided an anti-TGFbetaRII immunoglobulin single variable domain comprising an amino acid sequence that is at least 90% identical to the amino acid sequence of any one amino acid sequence selected from the group of any of the amino acid sequences set out in SEQ ID NOs: 1 to 23. In one embodiment, the anti-TGFbetaRII immunoglobulin single variable domain comprises an amino acid sequence that is identical to the amino acid sequence of any of the amino acid sequences set out in SEQ ID NOs: 1 to 23. Suitably, the anti-TGFbetaRII immunoglobulin single variable domain comprises an amino acid sequence as set out in any of SEQ ID NOs: 4 (DOM23h-271), 8 (DOM23h-437) or 10 (DOM23h-439). In another embodiment, the anti-TGFbetaRII immunoglobulin single variable domain comprises an amino acid sequence selected from the group of any of the amino acid sequences set out in SEQ ID NOs: 1 to 23. Suitably, the anti-TGFbetaRII immunoglobulin single variable domain binds TGFbetaRII, preferably human TGFbetaRII.

In another aspect, there is provided an anti-TGFbetaRII immunoglobulin single variable domain comprising an amino acid sequence of any one of the amino acid sequences set out in SEQ ID NOs: 1 to 23 that is modified at no more than 25 amino acid positions and comprises a CDR1 sequence that is at least 50% identical to the CDR1 sequence in any one of SEQ ID NOs: 1 to 23.

In a further aspect, there is provided an anti-TGFbetaRII immunoglobulin single variable domain comprising an amino acid sequence of any one of the amino acid sequences set out in SEQ ID NOs: 1 to 23 that is modified at no more than 25 amino acid positions and comprises a CDR2 sequence that is at least 50% identical to the CDR2 sequence in any one of SEQ ID NOs: 1 to 23.

In another aspect, there is provided an anti-TGFbetaRII immunoglobulin single variable domain comprising an amino acid sequence of any one of the amino acid sequences set out in SEQ ID NOs: 1 to 23 that is modified at no more than 25 amino acid positions and comprises a CDR3 sequence that is at least 50% identical to the CDR3 sequence in any one of SEQ ID NOs: 1 to 23.

In a further aspect, there is provided an anti-TGFbetaRII immunoglobulin single variable domain comprising an amino acid sequence of any one of the amino acid sequences set out in SEQ ID NOs: 1 to 23 that is modified at no more than 25 amino acid positions and comprises a CDR1 sequence that is at least 50% identical to a CDR1 sequence in any one of SEQ ID NOs: 1 to 23 and comprises a CDR2 sequence that is at least 50% identical to a CDR2 sequence in any one of SEQ ID NOs: 1 to 23.

In another aspect, there is provided an anti-TGFbetaRII immunoglobulin single variable domain comprising an amino acid sequence of any one of the amino acid sequences set out in SEQ ID NOs: 1 to 23 that is modified at no more than 25 amino acid positions and comprises a CDR1 sequence that is at least 50% identical to the CDR1 sequence in any one of SEQ ID NOs: 1 to 23 and comprises a CDR3 sequence that is at least 50% identical to the CDR3 sequence in any one of SEQ ID NOs: 1 to 23.

In yet another aspect, there is provided an anti-TGFbetaRII immunoglobulin single variable domain comprising an amino acid sequence of any one of the amino acid sequences set out in SEQ ID NOs: 1 to 23 that is modified at no more than 25 amino acid positions and comprises a CDR2 sequence that is at least 50% identical to the CDR2 sequence in any one of SEQ ID NOs: 1 to 23 and comprises a CDR3 sequence that is at least 50% identical to the CDR3 sequence in any one of SEQ ID NOs: 1 to 23.

In another aspect, there is provided an anti-TGFbetaRII immunoglobulin single variable domain comprising an amino acid sequence of any one of the amino acid sequences set out in SEQ ID NOs: 1 to 23 that is modified at no more than 25 amino acid positions and comprises a CDR1 sequence that is at least 50% identical to the CDR1 sequence in any one of SEQ ID NOs: 1 to 23 and comprises a CDR2 sequence that is at least 50% identical to the CDR2 sequence in any one of SEQ ID NOs: 1 to 23 and comprises a CDR3 sequence that is at least 50% identical to the CDR3 sequence in any one of SEQ ID NOs: 1 to 23.

In a further aspect, there is provided an anti-TGFbetaRII immunoglobulin single variable domain comprising a CDR3 sequence that is at least 50% identical to a CDR3 sequence selected from the group consisting of: the CDR3 sequence in any one of SEQ ID NOs: 1 to 23.

In another aspect, there is provided an anti-TGFbetaRII immunoglobulin single variable domain comprising a CDR3 sequence selected from the group consisting of: the CDR3 sequence in any one of SEQ ID NOs: 1 to 23.

In yet another aspect, there is provided an anti-TGFbetaRII immunoglobulin single variable domain comprising at least one CDR selected from the group consisting of: CDR1, CDR2, and CDR3, wherein the CDR1, CDR2, or CDR3 is identical to a CDR1, CDR2, or CDR3 sequence in any one of SEQ ID NOs: 1 to 23.

Suitably, CDR sequences are determined using the method of Kabat described herein. In one embodiment, the CDR sequences of each sequence are those set out in FIG. 7.

In one embodiment, there is provided an anti-TGFbetaRII immunoglobulin single variable domain or a polypeptide in accordance with any aspect of the disclosure which comprises comprising any of the following amino acids: N at position 61, R at position 64, H at position 102, R at position 39, D at position 53 or S at position 103 of the immunoglobulin single variable domain. In one embodiment, the immunoglobulin single variable domain or polypeptide comprises a combination of these amino acids. In another embodiment, the immunoglobulin single variable domain or polypeptide comprises amino acid N at 61 and R at 64. In these embodiments, the amino acid numbering is that of the immunoglobulin single variable domain, as exemplified, for example, by those sequences given in SEQ ID NOs: 1 to 23.

In another aspect, there is provided a ligand or binding moiety that has binding specificity for TGFbetaRII and inhibits the binding of an anti-TGFbetaRII immunoglobulin single variable domain comprising an amino acid sequence selected from the group of SEQ ID NOs: 1 to 23.

In a further aspect of the disclosure, there is provided a fusion protein comprising an immunoglobulin single variable domain, polypeptide or ligand in accordance with any aspect of the disclosure.

In one embodiment, the immunoglobulin single variable domain, polypeptide, ligand or fusion protein in accordance with the disclosure is one which neutralises TGFbeta activity. Suitably, the immunoglobulin single variable domain or polypeptide in accordance with the disclosure inhibits binding of TGFbeta to TGFbetaRII. In another embodiment, the immunoglobulin single variable domain or polypeptide in accordance with the disclosure inhibits TGFbeta signalling activity through TGFbetaRII. In another embodiment, the immunoglobulin single variable domain or polypeptide in accordance with the disclosure suppresses TGFbeta activity, in particular, TGFbeta cell growth activity. Suitably, TGFbetaRII is human TGFbetaRII.

In one embodiment, the immunoglobulin single variable domain, polypeptide, ligand or fusion protein in accordance with the disclosure is devoid of TGFbetaRII agonist activity at 10 micromolar (µM).

In another aspect, there is provided an immunoglobulin single variable domain, polypeptide, ligand or fusion protein in accordance with any aspect of the disclosure further comprising a half-life extending moiety. Suitably, the half-life extending moiety is a polyethylene glycol moiety, serum albumin or a fragment thereof, transferrin receptor or a transferrin-binding portion thereof, or an antibody or antibody fragment comprising a binding site for a polypeptide that enhances half-life in vivo. In one embodiment, the half-life extending moiety is an antibody or antibody fragment comprising a binding site for serum albumin or neonatal Fc receptor. In another embodiment, the half-life extending moiety is a dAb, antibody or antibody fragment.

In another aspect, the disclosure provides an isolated or recombinant nucleic acid encoding a polypeptide comprising an anti-TGFbetaRII immunoglobulin single variable domain, polypeptide, ligand or fusion protein in accordance with any aspect of the disclosure.

In one embodiment, the isolated or recombinant nucleic acid molecule comprises a nucleic acid molecule selected from the group of any of the nucleic acid molecules having the sequences set out in SEQ ID NOS: 24 to 46.

In one aspect, the disclosure provides an isolated or recombinant nucleic acid, wherein the nucleic acid comprises a nucleotide sequence that is at least 70% identical to the nucleotide sequence of any of the nucleic acid molecules having the sequences set out in SEQ ID NOS: 24 to 46, and wherein the nucleic acid encodes a polypeptide comprising an immunoglobulin single variable domain that specifically binds to TGFbetaRII.

In another aspect, there is provided a vector comprising a nucleic acid in accordance with the disclosure.

In a further aspect, there is provided a host cell comprising a nucleic acid or a vector in accordance with the disclosure. In yet another aspect of the disclosure there is provided a method of producing a polypeptide comprising an anti-TGFbetaRII immunoglobulin single variable domain or a polypeptide or ligand in accordance with the disclosure, the method comprising maintaining a host cell in accordance with the disclosure under conditions suitable for expression of said nucleic acid or vector, whereby a polypeptide comprising an immunoglobulin single variable domain, polypeptide or ligand is produced. Optionally, the method further comprises the step of isolating the polypeptide and optionally producing a variant, e.g., a mutated variant, having an improved affinity (Kd); or $EC_{50}$ for TGFbeta neutralization in a standard assay than the isolated polypeptide. Suitable assays for TGFbeta activity, such as a cell sensor assay, are described herein, for example, in the Examples section.

In one aspect of the disclosure, the anti-TGFbetaRII immunoglobulin single variable domain, polypeptide or ligand in accordance with the disclosure is for use as a medicament. Accordingly, there is provided a composition comprising anti-TGFbetaRII immunoglobulin single variable domain, polypeptide or ligand in accordance with the disclosure for use as a medicament.

Suitably, the anti-TGFbetaRII immunoglobulin single variable domain, polypeptide or ligand or composition in accordance with the disclosure is for treatment of a disease associated with TGFbeta signaling. Suitably, the disease is a tissue fibrosis, such as pulmonary fibrosis including idiopathic pulmonary fibrosis, liver fibrosis, including cirrhosis and chronic hepatitis, rheumatoid arthritis, ocular disorders, or fibrosis of the skin including keloid of skin, and kidney such as nephritis, kidney fibrosis and nephrosclerosis, or a vascular condition such as restenosis. Other diseases associated with TGFbeta signaling include vascular diseases such as hypertension, pre-eclampsia, hereditary haemorrhagic telangtiectasia type I (HHT1), HHT2, pulmonary arterial hypertension, aortic aneurysms, Marfan syndrome, familial aneurysm disorder, Loeys-Dietz syndrome, arterial tortuosity syndrome (ATS). Other diseases associated with TGFbeta signaling include diseases of the musculoskeletal system, such as Duchenne's muscular dystrophy and muscle fibrosis. Further diseases associated with TGFbeta signaling include cancer, such as colon, gastric, and pancreatic cancer, as well as glioma and NSCLC. In addition, the disclosure provides methods for targeting cancer by modulating TGFbeta signaling in tumour angiogenesis. Other diseases or conditions include those related to tissue scarring. Other diseases include pulmonary diseases such as COPD (Chronic obstructive pulmonary disease). In one aspect, the disclosure provides the anti-TGFbetaRII single variable domain or antagonist, composition or fusion protein for pulmonary delivery. In one aspect, the disclosure provides the anti-TGFbetaRII single variable domain or antagonist or fusion protein for delivery to the lung of a patient. In one aspect, the disclosure provides the use of the anti-TGFbetaRII single variable domain or antagonist or fusion protein in the manufacture of a medicament for pulmonary delivery. In one aspect, the disclosure provides the use of the anti-TGFbetaRII single variable domain or antagonist or fusion protein in accordance with the disclosure in the manufacture of a medicament for delivery to the lung of a patient.

In one embodiment, the variable domain per se, or when part of the antagonist or fusion protein, is resistant to proteases such as leucozyme and/or trypsin.

In one embodiment, the composition is for pulmonary delivery. Suitably, the composition comprises a monomeric dAb for pulmonary delivery. In another embodiment, the composition consists of a monomeric dAb for pulmonary delivery.

Suitably, the composition is for therapy or prophylaxis of a TGFbeta-mediated condition in a human.

Accordingly, in one embodiment, there is provided an anti-TGFbetaRII dAb for treating idiopathic pulmonary fibrosis. Suitably, the anti-TGFbetaRII dAb is provided as a monomeric dAb for pulmonary delivery, preferably lacking any tag (i.e., untagged) such as a myc or another purification tag.

In one aspect, the composition is a pharmaceutical composition and further comprises a pharmaceutically acceptable carrier, excipient or diluent.

In another aspect, there is provided a method of treating and/or preventing an TGFbeta-mediated condition in a human patient, the method comprising administering a composition comprising an anti-TGFbetaRII immunoglobulin single variable domain, polypeptide or ligand in accordance with the disclosure the to the patient.

In a further aspect, the disclosure provides a pulmonary delivery device containing a composition in accordance with the disclosure. Suitably, such a device is an inhaler or an intranasal administration device.

BRIEF DESCRIPTION OF THE FIGURES

FIG. 1 shows amino acid (SEQ ID NOs: 1-23) and nucleic acid (SEQ ID NOs: 24-46) sequences of dAbs in accordance with the disclosure.

FIG. 2 shows an alignment of DOM23h naive dAb amino acid sequences. Amino acids are numbered according to Kabat. CDR sequences are indicated in bold and underlined. Dots indicate sequence identity to DOM 23h-251 (SEQ ID NO: 2). Other sequences included in the sequence listing are SEQ ID NO:124 (GTEQ), SEQ ID NO: 125 (DASMGHTTRR), SEQ ID NO: 126 (PGHKWTANSRFDYWGQGTLV), SEQ ID NO: 127 (WDGVHAQ), SEQ ID NO: 128 (DYWGQGTLV), SEQ ID NO: 129 (SSTSPF) and SEQ ID NO: 130 (AAGVSGTYF).

FIG. 3 shows an alignment of DOM23h-262 (SEQ ID NO: 3) lineage amino acid sequences. Amino acids are numbered according to Kabat. CDR sequences are indicated in bold and underlined. Dots indicate sequence identity to DOM 23h-262 (SEQ ID NO: 3).

FIG. 4 shows an alignment of DOM23h-271 lineage amino acid sequences (SEQ ID NO: 4). Amino acids are numbered according to Kabat. CDR sequences are indicated in bold and underlined. Dots indicate sequence identity to DOM23h-271 (SEQ ID NO: 4).

FIG. 5 shows an alignment of DOM23h-437 lineage amino acid sequences (SEQ ID NO: 4). Amino acids are numbered according to Kabat. CDR sequences are indicated in bold and underlined. Dots indicate sequence identity to DOM23h-437 (SEQ ID NO: 8).

FIG. 6 shows an alignment of DOM23h-439 lineage amino acid sequences (SEQ ID NO: 10). Amino acids are numbered according to Kabat. CDR sequences are indicated in bold and underlined. Dots indicate sequence identity to DOM23h-439 (SEQ ID NO: 10).

FIG. 7 shows a table detailing CDR sequences.

FIG. 8 shows competition BIACORE™. DOM23h-437-6 (SEQ ID NO:19) was injected over a hTGFβ-RII-Fc coupled chip (injection 1), immediately followed by injection 2, consisting of either a mixture of DOM23h-437-6 (SEQ ID NO: 19) and DOM23h-271-3 (SEQ ID NO:) (A) or DOM23h-437-6 (SEQ ID NO: 19) and DOM23h-439-6 (B) (SEQ ID NO: 22). The chip was regenerated using two injections of 10 mM glycine pH 2.25 (injection 3).

FIG. 9 shows competition BIACORE™. DOM23h-437-9 (SEQ ID NO:21) was injected over a hTGFβ-RII-Fc coupled chip (injection 1), immediately followed by injection 2, consisting of a mixture of either DOM23h-437-9 (SEQ ID NO: 21) and DOM23h-262-10 (SEQ ID NO: 13) (C) or DOM23h-437-9 (SEQ ID NO:21) and DOM23h-271-12 (SEQ ID NO:16) (D). The chip was regenerated using two injections of 10 mM glycine pH 2.25 (injection 3).

FIG. 11 shows a Table listing sequence identifier numbers (SEQ ID NOs:) and their corresponding identifications.

DETAILED DESCRIPTION OF THE DISCLOSURE

Figure 10:
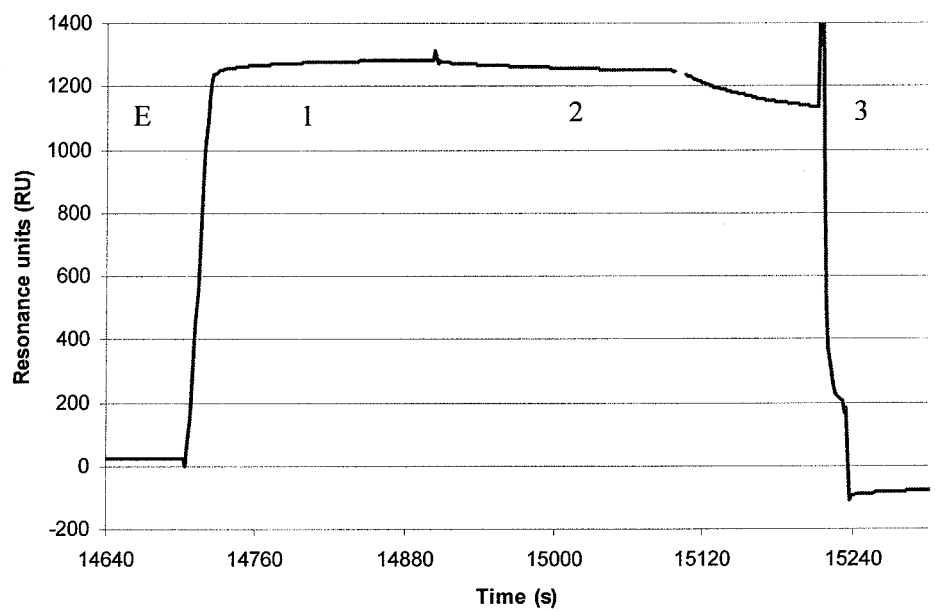
FIG. 10 shows competition BIACORE™. DOM23h-437-9 (SEQ ID NO: 21) was injected over a hTFGβ-RII-Fc coupled chip (injection 1), immediately followed by injection 2, consisting of a mixture of DOM23h-437-9 (SEQ ID NO: 21) and DOM23h-439-8 (SEQ ID NO: 23) (E). The chip was regenerated using two injections of 10 mM glycine pH 2.25 (injection 3).

Within this specification, the invention has been described, with reference to embodiments, in a way which enables a clear and concise specification to be written. It is intended and should be appreciated that embodiments may be variously combined or separated without parting from the disclosure.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook, et al., Molecular Cloning: A Laboratory Manual, 2d ed. (1989) Cold Spring Harbor Laboratory Press, Cold Spring Harbor, N.Y. and Ausubel, et al., Short Protocols in Molecular Biology (1999) 4$^{th}$ Ed, John Wiley & Sons, Inc., which are incorporated herein by reference) and chemical methods.

Immunoglobulin: As used herein, "immunoglobulin" refers to a family of polypeptides which retain the immunoglobulin fold characteristic of antibody molecules, which contain two β sheets and, usually, a conserved disulphide bond.

Domain: As used herein "domain" refers to a folded protein structure which retains its tertiary structure independently of the rest of the protein. Generally, domains are responsible for discrete functional properties of proteins and in many cases may be added, removed or transferred to other proteins without loss of function of the remainder of the protein and/or of the domain. By single antibody variable domain or immunoglobulin single variable domain is meant a folded polypeptide domain comprising sequences characteristic of antibody variable domains. It therefore includes complete antibody variable domains and modified variable domains, for example in which one or more loops have been replaced by sequences which are not characteristic of antibody variable domains, or antibody variable domains which have been truncated or comprise N- or C-terminal extensions, as well as folded fragments of variable domains which retain at least in part the binding activity and specificity of the full-length domain.

Immunoglobulin single variable domain: The phrase "immunoglobulin single variable domain" refers to an antibody variable domain ($V_H$, $V_{HH}$, $V_L$) or binding domain that specifically binds an antigen or epitope independently of different or other V regions or domains. An immunoglobulin single variable domain can be present in a format (e.g., homo- or hetero-multimer) with other variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is an "immunoglobulin single variable domain" as the term is used herein. A "single antibody variable domain" or an "antibody single variable domain" is the same as an "immunoglobulin single variable domain" as the term is used herein. An immunoglobulin single variable domain is in one embodiment a human antibody variable domain, but also includes single antibody variable domains from other species such as rodent (for example, as disclosed in WO 00/29004, the contents of which are incorporated herein by reference in their entirety), nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. The $V_{HH}$ may be humanized.

In all aspects of the disclosure, the immunoglobulin single variable domain is independently selected from antibody heavy chain and light chain single variable domains, e.g. $V_H$, $V_L$ and $V_{HH}$.

As used herein an "antibody" refers to IgG, IgM, IgA, IgD or IgE or a fragment (such as a Fab, F(ab')$_2$, Fv, disulphide linked Fv, scFv, closed conformation multispecific antibody, disulphide-linked scFv, diabody) whether derived from any species naturally producing an antibody, or created by recombinant DNA technology; whether isolated from, for example, serum, B-cells, hybridomas, transfectomas, yeast or bacteria.

Antibody format: In one embodiment, the immunoglobulin single variable domain, polypeptide or ligand in accordance with the disclosure can be provided in any antibody format. As used herein, "antibody format" refers to any suitable polypeptide structure in which one or more antibody variable domains can be incorporated so as to confer binding specificity for antigen on the structure. A variety of suitable antibody formats are known in the art, such as, chimeric antibodies, humanized antibodies, human antibodies, single chain antibodies, bispecific antibodies, antibody heavy chains, antibody light chains, homodimers and heterodimers of antibody heavy chains and/or light chains, antigen-binding fragments of any of the foregoing (e.g., a Fv fragment (e.g., single chain Fv (scFv), a disulfide bonded Fv), a Fab fragment, a Fab' fragment, a F(ab')$_2$ fragment), a single antibody variable domain (e.g., a dAb, $V_H$, $V_{HH}$, $V_L$), and modified versions of any of the foregoing (e.g., modified by the covalent attachment of polyethylene glycol or other suitable polymer or a humanized $V_{HH}$). In one embodiment, alternative antibody formats include alternative scaffolds in which the CDRs of any molecules in accordance with the disclosure can be grafted onto a suitable protein scaffold or skeleton, such as an affibody, a SpA scaffold, an LDL receptor class A domain, an avimer (see, e.g., U.S. Patent Application Publication Nos. 2005/0053973, 2005/0089932, 2005/0164301) or an EGF domain. Further, the ligand can be bivalent (heterobivalent) or multivalent (heteromultivalent) as described herein. In other embodiments, a "Universal framework" may be used wherein "Universal framework" refers to a single antibody framework sequence corresponding to the regions of an antibody conserved in sequence as defined by Kabat ("Sequences of Proteins of Immunological Interest", US Department of Health and Human Services) or corresponding to the human germline immunoglobulin repertoire or structure as defined by Chothia and Lesk, (1987) *J. Mol. Biol.* 196:910-917. The disclosure provides for the use of a single framework, or a set of such frameworks, which has been found to permit the derivation of virtually any binding specificity through variation in the hypervariable regions alone.

In embodiments of the disclosure described herein, instead of the use of an anti-TGFbetaRII "dAb" in a peptide or ligand of the disclosure, it is contemplated that the skilled addressee can use a polypeptide or domain that comprises one or more or all 3 of the CDRs of a dAb of the disclosure that binds TGFbetaRII (e.g., CDRs grafted onto a suitable protein scaffold or skeleton, e.g. an affibody, an SpA scaffold, an LDL receptor class A domain or an EGF domain). The disclosure as a whole is to be construed accordingly to provide disclosure of polypeptides using such domains in place of a dAb. In this respect, see WO2008096158, the disclosure of which is incorporated by reference.

In one embodiment, the anti-TGFbetaRII immunoglobulin single variable domain is any suitable immunoglobulin variable domain, and optionally is a human variable domain or a variable domain that comprises or are derived from human framework regions (e.g., DP47 or DPK9 framework regions).

Antigen: As described herein an "antigen" is a molecule that is bound by a binding domain according to the present disclosure. Typically, antigens are bound by antibody ligands and are capable of raising an antibody response in vivo. It may be, for example, a polypeptide, protein, nucleic acid or other molecule.

Epitope: An "epitope" is a unit of structure conventionally bound by an immunoglobulin $V_H/V_L$ pair. Epitopes define the minimum binding site for an antibody, and thus represent the target of specificity of an antibody. In the case of a single domain antibody, an epitope represents the unit of structure bound by a variable domain in isolation.

Binding: Typically, specific binding is indicated by a dissociation constant (Kd) of 50 nanomolar or less, optionally 250 picomolar or less. Specific binding of an antigen-binding protein to an antigen or epitope can be determined by a suitable assay, including, for example, Scatchard analysis and/or competitive binding assays, such as radioimmunoassays (RIA), enzyme immunoassays such as ELISA and sandwich competition assays, and the different variants thereof.

Binding affinity: Binding affinity is optionally determined using surface plasmon resonance (SPR) and BIACORE™ (Karlsson et al., 1991), using a BIACORE™ system (Uppsala, Sweden). The BIACORE™ system uses surface plasmon resonance (SPR, Welford K. 1991, Opt. Quant. Elect. 23:1; Morton and Myszka, 1998, Methods in Enzymology 295: 268) to monitor biomolecular interactions in real time, and uses surface plasmon resonance which can detect changes in the resonance angle of light at the surface of a thin gold film on a glass support as a result of changes in the refractive index of the surface up to 300 nm away. BIACORE™ analysis conveniently generates association rate constants, dissociation rate constants, equilibrium dissociation constants, and affinity constants. Binding affinity is obtained by assessing the association and dissociation rate constants using a BIACORE™ surface plasmon resonance system (BIACORE™, Inc.). A biosensor chip is activated for covalent coupling of the target according to the manufacturer's (BIACORE™) instructions. The target is then diluted and injected over the chip to obtain a signal in response units of immobilized material. Since the signal in resonance units (RU) is proportional to the mass of immobilized material, this represents a range of immobilized target densities on the matrix. Dissociation data are fit to a one-site model to obtain $k_{off}$+/−s.d. (standard deviation of measurements). Pseudo-first order rate constant (Kd's) are calculated for each association curve, and plotted as a function of protein concentration to obtain $k_{on}$+/−s.e. (standard error of fit). Equilibrium dissociation constants for binding, Kd's, are calculated from SPR measurements as $k_{off}/k_{on}$.

Another aspect of the disclosure provides an anti-TGFbetaRII immunoglobulin single variable domain that specifically binds to human TGFbetaRII. In one embodiment, the variable domain binds human TGFbetaRII with a dissociation constant (Kd) of about 50 nM, 40 nM, 30 nM, 20 nM, 10 nM or less, optionally about 9, 8, 7, 6 or 5 nM or less, optionally about 4 nM or less, about 3 nM or less or about 2 nM or less or about 1 nM or less, optionally about 500 pM or less. Suitably, where the variable domain has a dissociation constant in the range of about 50 nM to 500 pM, it is particularly suitable for local administration to a tissue of interest such as the lung. In this embodiment, a high concentration of such a "moderate affinity" binder can be provided as an effective therapeutic. In another embodiment, the variable domain binds human TGFbetaRII with a dissociation constant (Kd) of about 500 pM or less, optionally about 450 pM, 400 pM, 350 pM, 300 pM, 250 pM, 200 pM, 150 pM, 100 pM, 50 pM or less, optionally about 40 pM, 30 pM, 20 pM, 10 pM or less. Suitably, where the variable domain has a dissociation constant in the range of about 500 pM to 10 pM, it is particularly suitable for systemic administration such that the amount in any one tissue of interest is sufficient to provide an effective therapy. In this embodiment, a low concentration of such a "high affinity" binder can be provided as an effective therapeutic.

In one embodiment, single variable domains of the present disclosure show cross-reactivity between human TGFbetaRII and TGFbetaRII from another species, such as mouse TGFbetaRII. In this embodiment, the variable domains specifically bind human and mouse TGFbetaRII. This is particularly useful, since drug development typically requires testing of lead drug candidates in mouse systems before the drug is tested in humans. The provision of a drug that can bind human and mouse species allows one to test results in these system and make side-by-side comparisons of data using the same drug. This avoids the complication of needing to find a drug that works against a mouse TGFbetaRII and a separate drug that works against human TGFbetaRII, and also avoids the need to compare results in humans and mice using non-identical drugs. Cross reactivity between other species used in disease models such as dog or monkey such as cynomolgus monkey is also envisaged.

Optionally, the binding affinity of the immunoglobulin single variable domain for at least mouse TGFbetaRII and the binding affinity for human TGFbetaRII differ by no more than a factor of 10, 50 or 100.

CDRs: The immunoglobulin single variable domains (dAbs) described herein contain complementarity determining regions (CDR1, CDR2 and CDR3). The locations of CDRs and frame work (FR) regions and a numbering system have been defined by Kabat et al. (Kabat, E. A. et al., *Sequences of Proteins of Immunological Interest*, Fifth Edition, U.S. Department of Health and Human Services, U.S. Government Printing Office (1991)). The amino acid sequences of the CDRs (CDR1, CDR2, CDR3) of the $V_H$ (CDRH1 etc.) and $V_L$ (CDRL1 etc.) ($V_\kappa$) dAbs disclosed herein will be readily apparent to the person of skill in the art based on the well known Kabat amino acid numbering system and definition of the CDRs. According to the Kabat numbering system, the most commonly used method based on sequence variability, heavy chain CDR-H3 have varying lengths, insertions are numbered between residue H100 and H101 with letters up to K (i.e. H100, H100A . . . H100K, H101). CDRs can alternatively be determined using the system of Chothia (based on location of the structural loop regions) (Chothia et al., (1989) Conformations of immunoglobulin hypervariable regions; Nature 342, p877-883), according to AbM (compromise between Kabat and Chothia) or according to the Contact method (based on crystal structures and prediction of contact residues with antigen) as follows.

Once each residue has been numbered, one can then apply the following CDR definitions:
Kabat:
CDR H1: 31-35/35A/35B
CDR H2: 50-65
CDR H3: 95-102
CDR L1: 24-34
CDR L2: 50-56
CDR L3: 89-97
Chothia:
CDR H1: 26-32
CDR H2: 52-56
CDR H3: 95-102
CDR L1: 24-34
CDR L2: 50-56
CDR L3: 89-97
AbM:
(using Kabat numbering): (using Chothia numbering):
CDR H1: 26-35/35A/35B 26-35
CDR H2: 50-58 -
CDR H3: 95-102 -
CDR L1: 24-34 -
CDR L2: 50-56 -
CDR L3: 89-97 -
Contact
(using Kabat numbering): (using Chothia numbering):
CDR H1: 30-35/35A/35B 30-35
CDR H2: 47-58 -
CDR H3: 93-101 -
CDR L1: 30-36 -
CDR L2: 46-55 -
CDR L3: 89-96 -
("-" means the same numbering as Kabat)

TGFbetaRII: As used herein "TGFbetaRII" (transforming growth factor beta type II receptor; TGFβRII) refers to naturally occurring or endogenous mammalian TGFbetaRII proteins and to proteins having an amino acid sequence which is the same as that of a naturally occurring or endogenous corresponding mammalian TGFbetaRII protein (e.g., recombinant proteins, synthetic proteins (i.e., produced using the methods of synthetic organic chemistry)). Accordingly, as defined herein, the term includes mature TGFbetaRII protein, polymorphic or allelic variants, and other isoforms of TGFbetaRII and modified or unmodified forms of the foregoing (e.g., lipidated, glycosylated). Naturally occurring or endogenous TGFbetaRII includes wild type proteins such as mature TGFbetaRII, polymorphic or allelic variants and other isoforms and mutant forms which occur naturally in mammals (e.g., humans, non-human primates). Such proteins can be recovered or isolated from a source which naturally expresses TGFbetaRII, for example. These proteins and proteins having the same amino acid sequence as a naturally occurring or endogenous corresponding TGFbetaRII, are referred to by the name of the corresponding mammal. For example, where the corresponding mammal is a human, the protein is designated as a human TGFbetaRII. Human TGFbetaRII is described, for example, by Lin, et al., *Cell* 1992, Vol. 68(4), p. 775-785 and GenBank Accession No. M85079.

Human TGFbetaRII is a transmembrane receptor consisting of 567 amino acids with an extracellular domain of approximately 159 amino acids, a transmembrane domain and a cytoplasmic domain which comprises a protein kinase domain for signal transduction.

As used herein "TGFbetaRII" also includes a portion or fragment of TGFbetaRII. In one embodiment, such a portion or fragment includes the extracellular domain of TGFbetaRII or a portion thereof.

By "anti-TGFbetaRII" with reference to an immunoglobulin single variable domain, polypeptide, ligand, fusion protein or so forth is meant a moiety which recognises and binds TGFbetaRII. In one embodiment an "anti-TGFbetaRII" specifically recognises and/or specifically binds to the protein TGFbetaRII, and, suitably, human TGFbetaRII. In another embodiment, the anti-TGFbetaRII immunoglobulin single variable domain in accordance with the disclosure also binds to mouse TGFbetaRII (GenBank accession number NM_029575; described, for example in Massague et al., Cell 69 (7), 1067-1070 (1992)).

"TGFbeta" includes isoforms such as TGFbeta1, TGFbeta2 and TGFbeta3.

TGFbeta binds TGFbetaRII and, in a complex with TGFbetaRI initiates a signaling pathway. Accordingly, TGFbeta activity and inhibition or neutralization of TGFbeta activity can be determined through any assay which measures an output of TGFbeta signaling. TGFbeta signaling is reviewed, for example in Itoh, et al., *Eur. J. Biochem* 2000, Vol. 267, p. 6954; Dennler, et al., *Journal of Leucocyte Biol.* 2002, 71(5), p. 731-40. Thus, TGFbeta activity can be tested in a number of different assays familiar to the person skilled in the art "Inhibition" or "Neutralization" means that a biological activity of TGFbeta is reduced either totally or partially in the presence of the immunoglobulin single variable domain of the present disclosure in comparison to the activity of TGFbeta in the absence of such immunoglobulin single variable domain.

In one embodiment, an inhibition or neutralisation of TGFbeta activity is tested in an IL-11 release assay. In this embodiment, the ability of the immunoglobulin single variable domain in accordance with the disclosure is tested for its ability to inhibit human TGFbeta1 (TGFbeta1; TGF-β1) stimulated IL-11 release from cells such as A549 cells. TGFbeta1 (TGF-β1) binds directly to TGFbetaRII (TGF-βRII) and induces the assembly of the TGFbetaRI/RII (TGF-βRI/II) complex. TGFbetaRI (TGF-βRI) is phosphorylated and is able to signal through several pathways including the Smad 4 pathway. Activation of the Smad 4 pathway results in the release of IL-11. The IL-11 is secreted into the cell supernatant and is then measured by colourmetric ELISA. Suitable IL-11 release assays are described herein, such as the Human IL-11 QUANTIKINE™ ELISA assay kit supplied by R & D systems (ref. D1100).

In another embodiment, TGFbeta activity is tested in an assay for the ability of the immunoglobulin single variable domain in accordance with the disclosure to inhibit TGFbeta-induced expression of CAGA-luciferase in MC3T3-E1 cells in a MC3T3-E1 luciferase assay. Three copies of a TGFbeta-responsive sequence motif, termed a CAGA box are present in the human PAI-1 promoter and specifically binds Smad3 and 4 proteins. Cloning multiple copies of the CAGA box into a luciferase reporter construct confers TGFbeta responsiveness to cells transfected with the reporter system. One suitable assay is described herein and uses MC3T3-E1 cells (mouse osteoblasts) stably transfected with a $[CAGA]_{12}$-luciferase reporter construct (Dennler, et al., (1998) *EMBO J.* 17, 3091-3100).

Other suitable assays include a human SBE beta-lactamase cell assay (INVITROGEN®, cell sensor assay). Examples of suitable assays are described herein.

Suitably, the immunoglobulin single variable domain, polypeptide, ligand or fusion protein in accordance with the disclosure does not, itself activate TGFbetaRII receptor signalling. Accordingly, in one embodiment, the immunoglobulin single variable domain, polypeptide, ligand or fusion protein in accordance with the disclosure is devoid of agonist activity at 10 µM. Agonist activity can be determined by testing a compound of interest in a TGFbetaRII assay as described herein in the absence of TGFbeta. Where TGFbeta is absent, agonist activity of a compound of interest would be detected by detecting TGFbetaRII signalling.

Homology: Sequences similar or homologous (e.g., at least about 70% sequence identity) to the sequences disclosed herein are also part of the disclosure. In some embodiments, the sequence identity at the amino acid level can be about 75%, 80%, 85%, 90%, 91%, 92%, 93%, 94%, 95%, 96%, 97%, 98%, 99% or higher. At the nucleic acid level, the sequence identity can be about 60%, 65%, 70%, 75%, 80%, 85%, 90%, 91%, 92%, 93%, 94%, 95%, 96%, 97%, 98%, 99% or higher. Alternatively, substantial identity exists when the nucleic acid segments will hybridize under selective hybridization conditions (e.g., very high stringency hybridization conditions), to the complement of the strand. The nucleic acids may be present in whole cells, in a cell lysate, or in a partially purified or substantially pure form.

As used herein, the terms "low stringency," "medium stringency," "high stringency," or "very high stringency" conditions describe conditions for nucleic acid hybridization and washing. Guidance for performing hybridization reactions can be found in Current Protocols in Molecular Biology, John Wiley & Sons, N.Y. (1989), 6.3.1-6.3.6, which is incorporated herein by reference in its entirety. Aqueous and non-aqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and optionally (4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Calculations of "homology" or "sequence identity" or "similarity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least about 30%, optionally at least about 40%, optionally at least about 50%, optionally at least about 60%, and optionally at least about 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "homology" is equivalent to amino acid or nucleic acid "identity"). The percent identity between the two sequences is a function of the number of identical positions shared by the sequences, taking into account the number of gaps, and the length of each gap, which need to be introduced for optimal alignment of the two sequences.

Amino acid and nucleotide sequence alignments and homology, similarity or identity, as defined herein are optionally prepared and determined using the algorithm BLAST 2 Sequences, using default parameters (Tatusova, T. A. et al., FEMS Microbiol Lett, 174:187-188 (1999)). Alternatively, the BLAST algorithm (version 2.0) is employed for sequence alignment, with parameters set to default values. BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul, 1990, Proc. Natl. Acad. Sci. USA 87(6):2264-8.

Ligand: As used herein, the term "ligand" refers to a compound that comprises at least one peptide, polypeptide or protein moiety that has a binding site with binding specificity for TGFbetaRII. A ligand can also be referred to as a "binding moiety".

The ligands or binding moieties according to the disclosure optionally comprise immunoglobulin variable domains which have different binding specificities, and do not contain variable domain pairs which together form a binding site for target compound (I.e., do not comprise an immunoglobulin heavy chain variable domain and an immunoglobulin light chain variable domain that together form a binding site for TGFbetaRII). Optionally, each domain which has a binding site that has binding specificity for a target is an immunoglobulin single variable domain (e.g., immunoglobulin single heavy chain variable domain (e.g., $V_H$, $V_{HH}$), immunoglobulin single light chain variable domain (e.g., $V_L$)) that has binding specificity for a desired target (e.g., TGFbetaRII).

Thus, "ligands" include polypeptides that comprise two or more immunoglobulin single variable domains wherein each immunoglobulin single variable domain binds to a different target. Ligands also include polypeptides that comprise at least two immunoglobulin single variable domains or the CDR sequences of the single variable domains that bind different targets in a suitable format, such as an antibody format (e.g., IgG-like format, scFv, Fab, Fab', $F(ab')_2$) or a suitable protein scaffold or skeleton, such as an affibody, a SpA scaffold, an LDL receptor class A domain, an EGF domain, avimer and dual- and multi-specific ligands as described herein.

The polypeptide domain which has a binding site that has binding specificity for a target (e.g., TGFbetaRII) can also be a protein domain comprising a binding site for a desired target, e.g., a protein domain is selected from an affibody, a SpA domain, an LDL receptor class A domain, an avimer (see, e.g., U.S. Patent Application Publication Nos. 2005/0053973, 2005/0089932, 2005/0164301). If desired, a "ligand" can further comprise one or more additional moieties that can each independently be a peptide, polypeptide or protein moiety or a non-peptidic moiety (e.g., a polyalkylene glycol, a lipid, a carbohydrate). For example, the ligand can further comprise a half-life extending moiety as described herein (e.g., a polyalkylene glycol moiety, a moiety comprising albumin, an albumin fragment or albumin variant, a moiety comprising transferrin, a transferrin fragment or transferrin variant, a moiety that binds albumin, a moiety that binds neonatal Fc receptor).

Competes: As referred to herein, the term "competes" means that the binding of a first target (e.g., TGFbetaRII) to its cognate target binding domain (e.g., immunoglobulin single variable domain) is inhibited in the presence of a second binding domain (e.g., immunoglobulin single variable domain) that is specific for said cognate target. For example, binding may be inhibited sterically, for example by physical blocking of a binding domain or by alteration of the structure or environment of a binding domain such that its affinity or avidity for a target is reduced. See WO2006038027 for details of how to perform competition ELISA and competition BIA-CORE™ experiments to determine competition between first and second binding domains, the details of which are incorporated herein by reference to provide explicit disclosure for use in the present disclosure.

TGFbeta signaling: Suitably, the single variable domain, polypeptide or ligand of the disclosure can neutralize TGFbeta signaling through TGFbetaRII. By "neutralizing", it is meant that the normal signaling effect of TGFbeta is blocked such that the presence of TGFbeta has a neutral effect on TGFbetaRII signaling. Suitable methods for measuring a neutralizing effect include assays for TGFbeta signaling as described herein. In one embodiment, neutralization is observed as a % inhibition of TFGbeta activity in a TGFbeta signaling assay. In one embodiment, the single variable domain or polypeptide binds to the extracellular domain of TGFbetaRII thereby inhibiting/blocking the binding of TGFbeta to the extracellular domain of TGFbetaRII. Suitably, the single variable domain or polypeptide is useful where there is an excess of bioavailable TGFbeta and the single variable domain or polypeptide serves to inhibit the signaling activity of the bioavailable TGFbeta through inhibiting binding or TGFbeta to its cognate receptor TGFbetaRII.

As used herein, the term "antagonist of TGFbetaRII" or "anti-TGFbetaRII antagonist" or the like refers to an agent (e.g., a molecule, a compound) which binds TGFbetaRII and can inhibit a (i.e., one or more) function of TGFbetaRII. For example, an antagonist of TGFbetaRII can inhibit the binding of TGFbeta to TGFbetaRII and/or inhibit signal transduction mediated through TGFbetaRII. Accordingly, TGFbeta-mediated processes and cellular responses can be inhibited with an antagonist of TGFbetaRII.

In one embodiment, the ligand (e.g., immunoglobulin single variable domain) that binds TGFbetaRII inhibits binding of TGFbeta to a TGFbetaRII receptor with an inhibitory concentration 50 (IC50) that is ≤about 10 µM, ≤about 1 µM, ≤about 100 nM, ≤about 50 nM, ≤about 10 nM, ≤about 5 nM, ≤about 1 nM, ≤about 500 pM, ≤about 300 pM, ≤about 100 pM, or ≤about 10 pM. The IC50 is optionally determined using an in vitro TGFbeta receptor binding assay, or cell assay, such as the assay described herein.

It is also contemplated that the ligand (e.g., immunoglobulin single variable domain) optionally inhibit TGFbetaRII induced functions in a suitable in vitro assay with a neutralizing dose 50 (ND50) that is ≤about 10 µM, ≤about 1 µM, ≤about 100 nM, ≤about 50 nM, ≤about 10 nM, ≤about 5 nM, ≤about 1 nM, ≤about 500 pM, ≤about 300 pM, ≤about 100 pM, ≤about 10 pM, ≤about 1 pM ≤about 500 fM, ≤about 300 fM, ≤about 100 fM, ≤about 10 fM.

"dual-specific ligand": In one embodiment, the immunoglobulin single variable domain, polypeptide or ligand in accordance with the disclosure can be part of a "dual-specific ligand" which refers to a ligand comprising a first antigen or epitope binding site (e.g., first immunoglobulin single variable domain) and a second antigen or epitope binding site (e.g., second immunoglobulin single variable domain), wherein the binding sites or variable domains are capable of binding to two antigens (e.g., different antigens or two copies of the same antigen) or two epitopes on the same antigen which are not normally bound by a monospecific immunoglobulin. For example, the two epitopes may be on the same antigen, but are not the same epitope or sufficiently adjacent to be bound by a monospecific ligand. In one embodiment, dual-specific ligands according to the disclosure are composed of binding sites or variable domains which have different specificities, and do not contain mutually complementary variable domain pairs (i.e. VH/VL pairs) which have the same specificity (i.e., do not form a unitary binding site).

In one embodiment, a "dual-specific ligand" may bind to TGFbetaRII and to another target molecule. For example, another target molecule may be a tissue-specific target molecule such that the dual-specific ligand of the disclosure enables an anti-TGFbetaRII polypeptide or immunoglobulin single variable domain in accordance with the disclosure to be targeted to a tissue of interest. Such tissues include lung, liver and so forth.

The ligands of the disclosure (e.g., polypeptides, dAbs and antagonists) can be formatted as a fusion protein that contains a first immunoglobulin single variable domain that is fused directly to a second immunoglobulin single variable domain. If desired such a format can further comprise a half-life extending moiety. For example, the ligand can comprise a first immunoglobulin single variable domain that is fused directly to a second immunoglobulin single variable domain that is fused directly to an immunoglobulin single variable domain that binds serum albumin.

Generally, the orientation of the polypeptide domains that have a binding site with binding specificity for a target, and whether the ligand comprises a linker, is a matter of design choice. However, some orientations, with or without linkers, may provide better binding characteristics than other orientations. All orientations (e.g., dAb1-linker-dAb2; dAb2-linker-dAb1) are encompassed by the disclosure are ligands that contain an orientation that provides desired binding characteristics can be easily identified by screening.

Polypeptides and dAbs according to the disclosure, including dAb monomers, dimers and trimers, can be linked to an antibody Fc region, comprising one or both of $C_H2$ and $C_H3$ domains, and optionally a hinge region. For example, vectors encoding ligands linked as a single nucleotide sequence to an Fc region may be used to prepare such polypeptides.

The disclosure moreover provides dimers, trimers and polymers of the aforementioned dAb monomers.

Target: As used herein, the phrase "target" refers to a biological molecule (e.g., peptide, polypeptide, protein, lipid, carbohydrate) to which a polypeptide domain which has a binding site can bind. The target can be, for example, an intracellular target (e.g., an intracellular protein target), a soluble target (e.g., a secreted), or a cell surface target (e.g., a membrane protein, a receptor protein). In one embodiment, the target is TGFbetaRII. In another embodiment, the target is TGFbetaRII extracellular domain.

Complementary: As used herein "complementary" refers to when two immunoglobulin domains belong to families of structures which form cognate pairs or groups or are derived from such families and retain this feature. For example, a $V_H$ domain and a $V_L$ domain of an antibody are complementary; two $V_H$ domains are not complementary, and two $V_L$ domains are not complementary. Complementary domains may be found in other members of the immunoglobulin superfamily, such as the $V_\alpha$ and $V_\beta$ (or $\gamma$ and $\delta$) domains of the T-cell receptor. Domains which are artificial, such as domains based on protein scaffolds which do not bind epitopes unless engineered to do so, are non-complementary. Likewise, two domains based on (for example) an immunoglobulin domain and a fibronectin domain are not complementary.

"Affinity" and "avidity" are terms of art that describe the strength of a binding interaction. With respect to the ligands of the disclosure, avidity refers to the overall strength of binding between the targets (e.g., first target and second target) on the cell and the ligand. Avidity is more than the sum of the individual affinities for the individual targets.

Nucleic acid molecules, vectors and host cells: The disclosure also provides isolated and/or recombinant nucleic acid molecules encoding ligands (single variable domains, fusion proteins, polypeptides, dual-specific ligands and multispecific ligands) as described herein.

Nucleic acids referred to herein as "isolated" are nucleic acids which have been separated away from the nucleic acids of the genomic DNA or cellular RNA of their source of origin (e.g., as it exists in cells or in a mixture of nucleic acids such as a library), and include nucleic acids obtained by methods described herein or other suitable methods, including essentially pure nucleic acids, nucleic acids produced by chemical synthesis, by combinations of biological and chemical methods, and recombinant nucleic acids which are isolated (see e.g., Daugherty, B. L. et al., *Nucleic Acids Res.*, 19(9): 2471-2476 (1991); Lewis, A. P. and J. S. Crowe, *Gene*, 101: 297-302 (1991)).

Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes.

In certain embodiments, the isolated and/or recombinant nucleic acid comprises a nucleotide sequence encoding an immunoglobulin single variable domain, polypeptide or ligand, as described herein, wherein said ligand comprises an amino acid sequence that has at least about 80%, at least about 85%, at least about 90%, at least about 91%, at least about 92%, at least about 93%, at least about 94%, at least about 95%, at least about 96%, at least about 97%, at least about 98%, or at least about 99% amino acid sequence identity with the amino acid sequence of a dAb that binds TGFbetaRII disclosed herein, e.g. amino acid sequences set out in any of SEQ ID NOS: 1 to 23. Nucleotide sequence identity can be determined over the whole length of the nucleotide sequence that encodes the selected anti-TGFbetaRII dAb.

The disclosure also provides a vector comprising a recombinant nucleic acid molecule of the disclosure. In certain embodiments, the vector is an expression vector comprising one or more expression control elements or sequences that are operably linked to the recombinant nucleic acid of the disclosure. The disclosure also provides a recombinant host cell comprising a recombinant nucleic acid molecule or vector of the disclosure. Suitable vectors (e.g., plasmids, phagemids), expression control elements, host cells and methods for producing recombinant host cells of the disclosure are well-known in the art, and examples are further described herein.

Suitable expression vectors can contain a number of components, for example, an origin of replication, a selectable marker gene, one or more expression control elements, such as a transcription control element (e.g., promoter, enhancer, terminator) and/or one or more translation signals, a signal sequence or leader sequence, and the like. Expression control elements and a signal sequence, if present, can be provided by the vector or other source. For example, the transcriptional and/or translational control sequences of a cloned nucleic acid encoding an antibody chain can be used to direct expression.

A promoter can be provided for expression in a desired host cell. Promoters can be constitutive or inducible. For example, a promoter can be operably linked to a nucleic acid encoding an antibody, antibody chain or portion thereof, such that it directs transcription of the nucleic acid. A variety of suitable promoters for prokaryotic (e.g., lac, tac, T3, T7 promoters for *E. coli*) and eukaryotic (e.g., Simian Virus 40 early or late promoter, Rous sarcoma virus long terminal repeat promoter, cytomegalovirus promoter, adenovirus late promoter) hosts are available.

In addition, expression vectors typically comprise a selectable marker for selection of host cells carrying the vector, and, in the case of a replicable expression vector, an origin of replication. Genes encoding products which confer antibiotic or drug resistance are common selectable markers and may be used in prokaryotic (e.g., lactamase gene (ampicillin resistance), Tet gene for tetracycline resistance) and eukaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated. Suitable expression vectors for expression in mammalian cells and prokaryotic cells (*E. coli*), insect cells (Drosophila Schnieder S2 cells, Sf9) and yeast (*P. methanolica, P. pastoris, S. cerevisiae*) are well-known in the art.

Suitable host cells can be prokaryotic, including bacterial cells such as *E. coli, B. subtilis* and/or other suitable bacteria; eukaryotic cells, such as fungal or yeast cells (e.g., *Pichia pastoris, Aspergillus* sp., *Saccharomyces cerevisiae, Schizosaccharomyces pombe, Neurospora crassa*), or other lower eukaryotic cells, and cells of higher eukaryotes such as those from insects (e.g., *Drosophila* Schnieder S2 cells, Sf9 insect cells (WO 94/26087 (O'Connor)), mammals (e.g., COS cells, such as COS-1 (ATCC Accession No. CRL-1650) and COS-7 (ATCC Accession No. CRL-1651), CHO (e.g., ATCC Accession No. CRL-9096, CHO DG44 (Urlaub, G. and Chasin, L A., *Proc. Natl. Acad. Sci. USA*, 77(7):4216-4220 (1980))), 293 (ATCC Accession No. CRL-1573), HeLa (ATCC Accession No. CCL-2), CV1 (ATCC Accession No. CCL-70), WOP (Dailey, L., et al., *J. Virol.*, 54:739-749 (1985), 3T3, 293T (Pear, W. S., et al., *Proc. Natl. Acad. Sci. U.S.A.*, 90:8392-8396 (1993)) NS0 cells, SP2/0, HuT 78 cells and the like, or plants (e.g., tobacco). (See, for example, Ausubel, F. M. et al., eds. *Current Protocols in Molecular*

*Biology*, Greene Publishing Associates and John Wiley & Sons Inc. (1993).) In some embodiments, the host cell is an isolated host cell and is not part of a multicellular organism (e.g., plant or animal). In certain embodiments, the host cell is a non-human host cell.

The disclosure also provides a method for producing a ligand (e.g., dual-specific ligand, multispecific ligand) of the disclosure, comprising maintaining a recombinant host cell comprising a recombinant nucleic acid of the disclosure under conditions suitable for expression of the recombinant nucleic acid, whereby the recombinant nucleic acid is expressed and a ligand is produced. In some embodiments, the method further comprises isolating the ligand.

Reference is made to WO200708515, page 161, line 24 to page 189, line 10 for details of disclosure that is applicable to embodiments of the present disclosure. This disclosure is hereby incorporated herein by reference as though it appears explicitly in the text of the present disclosure and relates to the embodiments of the present disclosure, and to provide explicit support for disclosure to incorporated into claims below. This includes disclosure presented in WO200708515, page 161, line 24 to page 189, line 10 providing details of the "Preparation of Immunoglobulin Based Ligands", "Library vector systems", "Library Construction", "Combining Single Variable Domains", "Characterisation of Ligands", "Structure of Ligands", "Skeletons", "Protein Scaffolds", "Scaffolds for Use in Constructing Ligands", "Diversification of the Canonical Sequence" and "Therapeutic and diagnostic compositions and uses", as well as definitions of "operably linked", "naive", "prevention", "suppression", "treatment", "allergic disease", "Th2-mediated disease", "therapeutically-effective dose" and "effective".

The phrase, "half-life" refers to the time taken for the serum concentration of the immunoglobulin single variable domain, polypeptide or ligand to reduce by 50%, in vivo, for example due to degradation of the ligand and/or clearance or sequestration of the ligand by natural mechanisms. The ligands of the disclosure can be stabilized in vivo and their half-life increased by binding to molecules which resist degradation and/or clearance or sequestration. Typically, such molecules are naturally occurring proteins which themselves have a long half-life in vivo. The half-life of a ligand is increased if its functional activity persists, in vivo, for a longer period than a similar ligand which is not specific for the half-life increasing molecule. Thus a ligand specific for HSA and a target molecules is compared with the same ligand wherein the specificity to HSA is not present, that is does not bind HSA but binds another molecule. Typically, the half-life is increased by 10%, 20%, 30%, 40%, 50% or more. Increases in the range of 2×, 3×, 4×, 5×, 10×, 20×, 30×, 40×, 50× or more of the half-life are possible. Alternatively, or in addition, increases in the range of up to 30×, 40×, 50×, 60×, 70×, 80×, 90×, 100×, 150× of the half life are possible.

Formats: Increased half-life can be useful in in vivo applications of immunoglobulins, especially antibodies and most especially antibody fragments of small size. Such fragments (Fvs, disulphide bonded Fvs, Fabs, scFvs, dAbs) are generally rapidly cleared from the body. dAbs, polypeptides or ligands in accordance with the disclosure can be adapted to provide increased half-life in vivo and consequently longer persistence times in the body of the functional activity of the ligand.

Methods for pharmacokinetic analysis and determination of ligand half-life will be familiar to those skilled in the art. Details may be found in Kenneth, A et al: Chemical Stability of Pharmaceuticals: A Handbook for Pharmacists and in Peters et al, Pharmacokinetic analysis: A Practical Approach (1996). Reference is also made to "Pharmacokinetics", M Gibaldi & D Perron, published by Marcel Dekker, $2^{nd}$ Rev. ex edition (1982), which describes pharmacokinetic parameters such as t alpha and t beta half lives and area under the curve (AUC).

Half lives (t½ alpha and t½ beta) and AUC can be determined from a curve of serum concentration of ligand against time. The WINNONLIN™ analysis package (available from Pharsight Corp., Mountain View, Calif. 94040, USA) can be used, for example, to model the curve. In a first phase (the alpha phase) the ligand is undergoing mainly distribution in the patient, with some elimination. A second phase (beta phase) is the terminal phase when the ligand has been distributed and the serum concentration is decreasing as the ligand is cleared from the patient. The t alpha half life is the half life of the first phase and the t beta half life is the half life of the second phase. Thus, in one embodiment, the present disclosure provides a ligand or a composition comprising a ligand according to the disclosure having a tα half-life in the range of 15 minutes or more. In one embodiment, the lower end of the range is 30 minutes, 45 minutes, 1 hour, 2 hours, 3 hours, 4 hours, 5 hours, 6 hours, 7 hours, 10 hours, 11 hours or 12 hours. In addition, or alternatively, a ligand or composition according to the disclosure will have a tα half life in the range of up to and including 12 hours. In one embodiment, the upper end of the range is 11, 10, 9, 8, 7, 6 or 5 hours. An example of a suitable range is 1 to 6 hours, 2 to 5 hours or 3 to 4 hours.

In one embodiment, the present disclosure provides a ligand (polypeptide, dAb or antagonist) or a composition comprising a ligand according to the disclosure having a tβ half-life in the range of about 2.5 hours or more. In one embodiment, the lower end of the range is about 3 hours, about 4 hours, about 5 hours, about 6 hours, about 7 hours, about 10 hours, about 11 hours, or about 12 hours. In addition, or alternatively, a ligand or composition according to the disclosure has a tβ half-life in the range of up to and including 21 days. In one embodiment, the upper end of the range is about 12 hours, about 24 hours, about 2 days, about 3 days, about 5 days, about 10 days, about 15 days or about 20 days. In one embodiment a ligand or composition according to the disclosure will have a tβ half life in the range about 12 to about 60 hours. In a further embodiment, it will be in the range about 12 to about 48 hours. In a further embodiment still, it will be in the range about 12 to about 26 hours.

In addition, or alternatively to the above criteria, the present disclosure provides a ligand or a composition comprising a ligand according to the disclosure having an AUC value (area under the curve) in the range of about 1 mg·min/ml or more. In one embodiment, the lower end of the range is about 5, about 10, about 15, about 20, about 30, about 100, about 200 or about 300 mg·min/ml. In addition, or alternatively, a ligand or composition according to the disclosure has an AUC in the range of up to about 600 mg·min/ml. In one embodiment, the upper end of the range is about 500, about 400, about 300, about 200, about 150, about 100, about 75 or about 50 mg·min/ml. In one embodiment a ligand according to the disclosure will have a AUC in the range selected from the group consisting of the following: about 15 to about 150 mg·min/ml, about 15 to about 100 mg·min/ml, about 15 to about 75 mg·min/ml, and about 15 to about 50 mg·min/ml.

Polypeptides and dAbs of the disclosure and antagonists comprising these can be formatted to have a larger hydrodynamic size, for example, by attachment of a PEG group, serum albumin, transferrin, transferrin receptor or at least the transferrin-binding portion thereof, an antibody Fc region, or by conjugation to an antibody domain. For example, polypeptides dAbs and antagonists formatted as a larger antigen-binding fragment of an antibody or as an antibody (e.g., formatted as a Fab, Fab', F(ab)$_2$, F(ab')$_2$, IgG, scFv).

As used herein, "hydrodynamic size" refers to the apparent size of a molecule (e.g., a protein molecule, ligand) based on the diffusion of the molecule through an aqueous solution. The diffusion or motion of a protein through solution can be processed to derive an apparent size of the protein, where the size is given by the "Stokes radius" or "hydrodynamic radius" of the protein particle. The "hydrodynamic size" of a protein depends on both mass and shape (conformation), such that two proteins having the same molecular mass may have differing hydrodynamic sizes based on the overall conformation of the protein.

Hydrodynamic size of the ligands (e.g., dAb monomers and multimers) of the disclosure may be determined using methods which are well known in the art. For example, gel filtration chromatography may be used to determine the hydrodynamic size of a ligand. Suitable gel filtration matrices for determining the hydrodynamic sizes of ligands, such as cross-linked agarose matrices, are well known and readily available.

The size of a ligand format (e.g., the size of a PEG moiety attached to a dAb monomer), can be varied depending on the desired application. For example, where ligand is intended to leave the circulation and enter into peripheral tissues, it is desirable to keep the hydrodynamic size of the ligand low to facilitate extravazation from the blood stream. Alternatively, where it is desired to have the ligand remain in the systemic circulation for a longer period of time the size of the ligand can be increased, for example by formatting as an Ig like protein.

Half-life extension by targeting an antigen or epitope that increases half-live in vivo: The hydrodynamic size of a ligand and its serum half-life can also be increased by conjugating or associating an TGFbetaRII binding polypeptide, dAb or ligand of the disclosure to a binding domain (e.g., antibody or antibody fragment) that binds an antigen or epitope that increases half-live in vivo, as described herein. For example, the TGFbetaRII binding agent (e.g., polypeptide) can be conjugated or linked to an anti-serum albumin or anti-neonatal Fc receptor antibody or antibody fragment, e.g. an anti-SA or anti-neonatal Fc receptor dAb, Fab, Fab' or scFv, or to an anti-SA affibody or anti-neonatal Fc receptor Affibody or an anti-SA avimer, or an anti-SA binding domain which comprises a scaffold selected from, but not limited to, the group consisting of CTLA-4, lipocallin, SpA, an affibody, an avimer, GroEl and fibronectin (see WO2008096158 for disclosure of these binding domains, which domains and their sequences are incorporated herein by reference and form part of the disclosure of the present text). Conjugating refers to a composition comprising polypeptide, dAb or antagonist of the disclosure that is bonded (covalently or noncovalently) to a binding domain such as a binding domain that binds serum albumin.

Typically, a polypeptide that enhances serum half-life in vivo is a polypeptide which occurs naturally in vivo and which resists degradation or removal by endogenous mechanisms which remove unwanted material from the organism (e.g., human). For example, a polypeptide that enhances serum half-life in vivo can be selected from proteins from the extracellular matrix, proteins found in blood, proteins found at the blood brain barrier or in neural tissue, proteins localized to the kidney, liver, lung, heart, skin or bone, stress proteins, disease-specific proteins, or proteins involved in Fc transport. Suitable polypeptides are described, for example, in WO2008/096158.

Such an approach can also be used for targeted delivery of a single variable domain, polypeptide or ligand in accordance with the disclosure to a tissue of interest. In one embodiment targeted delivery of a high affinity single variable domain in accordance with the disclosure is provided.

dAbs that Bind Serum Albumin: The disclosure in one embodiment provides a polypeptide or antagonist (e.g., dual specific ligand comprising an anti-TGFbetaRII dAb (a first dAb)) that binds to TGFbetaRII and a second dAb that binds serum albumin (SA), the second dAb binding SA. Details of dual specific ligands are found in WO03002609, WO04003019, WO2008096158 and WO04058821.

In particular embodiments of the ligands and antagonists, the dAb binds human serum albumin and competes for binding to albumin with a dAb selected from the group consisting of any of the dAb sequences disclosed in WO2004003019 (which sequences and their nucleic acid counterpart are incorporated herein by reference and form part of the disclosure of the present text), any of the dAb sequences disclosed in WO2007080392 (which sequences and their nucleic acid counterpart are incorporated herein by reference and form part of the disclosure of the present text), any of the dAb sequences disclosed in WO2008096158 (which sequences and their nucleic acid counterpart are incorporated herein by reference and form part of the disclosure of the present text).

In certain embodiments, the dAb binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with the amino acid sequence of a dAb described in any of WO2004003019, WO2007080392 or WO2008096158. For example, the dAb that binds human serum albumin can comprise an amino acid sequence that has at least about 90%, or at least about 95%, or at least about 96%, or at least about 97%, or at least about 98%, or at least about 99% amino acid sequence identity with the amino acid sequence of any of these dAbs. In certain embodiments, the dAb binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with the amino acid sequence of the amino acid sequence of any of these dAbs.

In more particular embodiments, the dAb is a $V_\kappa$ dAb that binds human serum albumin. In more particular embodiments, the dAb is a $V_H$ dAb that binds human serum albumin.

Suitable Camelid $V_{HH}$ that bind serum albumin include those disclosed in WO 2004041862 (Ablynx N.V.) and in WO2007080392 (which $V_{HH}$ sequences and their nucleic acid counterpart are incorporated herein by reference and form part of the disclosure of the present text). In certain embodiments, the Camelid $V_{HH}$ binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with those sequences disclosed in WO2007080392 or any one of SEQ ID NOS:518-534, these sequence numbers corresponding to those cited in WO2007080392 or WO 2004041862.

In an alternative embodiment, the antagonist or ligand comprises a binding moiety specific for TGFbetaRII (e.g., human TGFbetaRII), wherein the moiety comprises non-immunoglobulin sequences as described in WO2008096158, the disclosure of these binding moieties, their methods of production and selection (e.g., from diverse libraries) and their sequences are incorporated herein by reference as part of the disclosure of the present text).

Conjugation to a half-life extending moiety (e.g., albumin): In one embodiment, a (one or more) half-life extending moiety (e.g., albumin, transferrin and fragments and analogues thereof) is conjugated or associated with the TGFbetaRII-binding polypeptide, dAb or antagonist of the disclosure. Examples of suitable albumin, albumin fragments or albumin variants for use in a TGFbetaRII-binding format are described in WO2005077042, which disclosure is incorporated herein by reference and forms part of the disclosure of the present text.

Further examples of suitable albumin, fragments and analogs for use in a TGFbetaRII-binding format are described in WO 03076567, which disclosure is incorporated herein by reference and which forms part of the disclosure of the present text.

Where a (one or more) half-life extending moiety (e.g., albumin, transferrin and fragments and analogues thereof) is used to format the TGFbetaRII-binding polypeptides, dAbs and antagonists of the disclosure, it can be conjugated using any suitable method, such as, by direct fusion to the TGFbetaRII-binding moiety (e.g., anti-TGFbetaRII dAb), for example by using a single nucleotide construct that encodes a fusion protein, wherein the fusion protein is encoded as a single polypeptide chain with the half-life extending moiety located N- or C-terminally to the TGFbetaRII binding moiety. Alternatively, conjugation can be achieved by using a peptide linker between moieties, e.g., a peptide linker as described in WO 03076567 or WO 2004003019 (these linker disclosures being incorporated by reference in the present disclosure to provide examples for use in the present disclosure).

Conjugation to PEG: In other embodiments, the half-life extending moiety is a polyethylene glycol moiety. In one embodiment, the antagonist comprises (optionally consists of) a single variable domain of the disclosure linked to a polyethylene glycol moiety (optionally, wherein said moiety has a size of about 20 to about 50 kDa, optionally about 40 kDa linear or branched PEG). Reference is made to WO04081026 for more detail on PEGylation of dAbs and binding moieties. In one embodiment, the antagonist consists of a dAb monomer linked to a PEG, wherein the dAb monomer is a single variable domain according to the disclosure.

In another embodiment, a single variable domain, ligand or polypeptide in accordance with the disclosure may be linked to a toxin moiety or toxin.

Protease resistance: Single variable domains, polypeptides or ligands in accordance with the disclosure can be modified to improve their resistance to protease degradation. As used herein, a peptide or polypeptide (e.g. a domain antibody (dAb)) that is "resistant to protease degradation" is not substantially degraded by a protease when incubated with the protease under conditions suitable for protease activity. A polypeptide (e.g., a dAb) is not substantially degraded when no more than about 25%, no more than about 20%, no more than about 15%, no more than about 14%, no more than about 13%, no more than about 12%, no more than about 11%, no more than about 10%, no more than about 9%, no more than about 8%, no more than about 7%, no more than about 6%, no more than about 5%, no more than about 4%, no more than about 3%, no more that about 2%, no more than about 1%, or substantially none of the protein is degraded by protease after incubation with the protease for about one hour at a temperature suitable for protease activity. For example at 37 or 50 degrees C. Protein degradation can be assessed using any suitable method, for example, by SDS-PAGE or by functional assay (e.g., ligand binding) as described herein.

Methods for generating dAbs with enhanced protease resistance are disclosed, for example, in WO2008149143. In one embodiment, the single variable domain, polypeptide or ligand in accordance with the disclosure is resistant to degradation by leucozyme and/or trypsin. Polypeptides, immunoglobulin single variable domains and ligands of the disclosure may be resistant to one or more of the following: serine protease, cysteine protease, aspartate proteases, thiol proteases, matrix metalloprotease, carboxypeptidase (e.g., carboxypeptidase A, carboxypeptidase B), trypsin, chymotrypsin, pepsin, papain, elastase, leukozyme, pancreatin, thrombin, plasmin, cathepsins (e.g., cathepsin G), proteinase (e.g., proteinase 1, proteinase 2, proteinase 3), thermolysin, chymosin, enteropeptidase, caspase (e.g., caspase 1, caspase 2, caspase 4, caspase 5, caspase 9, caspase 12, caspase 13), calpain, ficain, clostripain, actinidain, bromelain, and separase. In particular embodiments, the protease is trypsin, elastase or leucozyme. The protease can also be provided by a biological extract, biological homogenate or biological preparation. In one embodiment, the protease is a protease found in sputum, mucus (e.g., gastric mucus, nasal mucus, bronchial mucus), bronchoalveolar lavage, lung homogenate, lung extract, pancreatic extract, gastric fluid, saliva. In one embodiment, the protease is one found in the eye and/or tears. Examples of such proteases found in the eye include caspases, calpains, matrix metalloproteases, disintegrin, metalloproteinases (ADAMs) and ADAM with thrombospondin motifs, the proteosomes, tissue plasminogen activator, secretases, cathepsin B and D, cystatin C, serine protease PRSS1, ubiquitin proteosome pathway (UPP). In one embodiment, the protease is a non bacterial protease. In an embodiment, the protease is an animal, e.g., mammalian, e.g., human, protease. In an embodiment, the protease is a GI tract protease or a pulmonary tissue protease, e.g., a GI tract protease or a pulmonary tissue protease found in humans. Such protease listed here can also be used in the methods described, for example, in WO2008149143, involving exposure of a repertoire of library to a protease.

Stability: In one aspect of the disclosure, the polypeptides, single variable domains, dAbs, ligands, compositions or formulations of the disclosure are substantially stable after incubation (at a concentration of polypeptide or variable domain of 1 mg/ml) at 37 to 50° C. for 14 days in Britton Robinson or PBS buffer. In one embodiment, at least 65, 70, 75, 80, 85, 86, 87, 88, 90, 91, 92, 93, 94, 95, 96, 97, 98, 99% of the polypeptide, antagonist or variable domain etc. remains unaggregated after such incubation at 37 degrees C. In one embodiment, at least 65, 70, 75, 80, 85, 86, 87, 88, 90, 91, 92, 93, 94, 95, 96, 97, 98, 99% of the polypeptide or variable domain remains monomeric after such incubation at 37 degrees C.

In one embodiment, at least 5, 10, 15, 20, 25, 30, 35, 40, 45, 50, 55, 60, 65, 70, 75, 80, 85, 86, 87, 88, 90, 91, 92, 93, 94, 95, 96, 97, 98, 99% of the polypeptide, antagonist or variable domain remains unaggregated after such incubation at 50 degrees C. In one embodiment, at least 5, 10, 15, 20, 25, 30, 35, 40, 45, 50, 55, 60, 65, 70, 75, 80, 85, 86, 87, 88, 90, 91, 92, 93, 94, 95, 96, 97, 98, 99% of the polypeptide or variable domain remains monomeric after such incubation at 50 degrees C. In one embodiment, no aggregation of the polypeptides, variable domains, antagonists is seen after any one of such incubations. In one embodiment, the pI of the polypeptide or variable domain remains unchanged or substantially unchanged after incubation at 37 degrees C. at a concentration of polypeptide or variable domain of 1 mg/ml in Britton-Robinson buffer. In one aspect of the disclosure, the polypeptides, variable domains, antagonists, compositions or formulations of the disclosure are substantially stable after incubation (at a concentration of polypeptide or variable domain of 100 mg/ml) at 4° C. for 7 days in Britton Robinson buffer or PBS at a pH of 7 to 7.5 (e.g., at pH7 or pH7.5). In one embodiment, at least 95, 95.5, 96, 96.5, 97, 97.5, 98, 98.5, 99 or 99.5% of the polypeptide, antagonist or variable domain remains unaggregated after such incubation. In one embodiment, at least 95, 95.5, 96, 96.5, 97, 97.5, 98, 98.5, 99 or 99.5% of the polypeptide or variable domain remains monomeric after such incubation. In one embodiment, no aggregation of the polypeptides, variable domains, antagonists is seen after any one of such incubations.

In one aspect of the disclosure, the polypeptides, variable domains, antagonists, compositions or formulations of the disclosure are substantially stable after nebulisation (e.g. at a concentration of polypeptide or variable domain of 40 mg/ml) e.g., at room temperature, 20 degrees C. or 37° C., for 1 hour, e.g. jet nebuliser, e.g. in a Pari LC+ cup. In one embodiment, at least 65, 70, 75, 80, 85, 86, 87, 88, 90, 91, 92, 93, 94, 95, 95.5, 96, 96.5, 97, 97.5, 98, 98.5, 99 or 99.5% of the polypeptide, antagonist or variable domain remains unaggregated after such nebulisation. In one embodiment, at least 65, 70, 75, 80, 85, 86, 87, 88, 90, 91, 92, 93, 94, 95, 95.5, 96, 96.5, 97, 97.5, 98, 98.5, 99 or 99.5% of the polypeptide or variable domain remains monomeric after such nebulisation. In one embodiment, no aggregation of the polypeptides, variable domains, antagonists is seen after any one of such nebulisation. Monomeric form: In one embodiment, the dAb of the present disclosure is provided in a monomeric form. Suitably, the disclosure provides a (substantially) pure monomer. In one embodiment, the dAb is at least 98, 99, 99.5% pure or 100% pure monomer. To determine whether dAbs are monomeric or form higher order oligomers in solution, they can be analysed by SEC-MALLS. SEC MALLS (size exclusion chromatography with multi-angle-LASER-light-scattering) is a non-invasive technique for the characterizing of macromolecules in solution. Briefly, proteins (at concentration of 1 mg/mL in buffer Dulbecco's PBS) are separated according to their hydrodynamic properties by size exclusion chromatography (column: TSK3000; S200). Following separation, the propensity of the protein to scatter light is measured using a multi-angle-LASER-light-scattering (MALLS) detector. The intensity of the scattered light while protein passes through the detector is measured as a function of angle. This measurement taken together with the protein concentration determined using the refractive index (RI) detector allows calculation of the molar mass using appropriate equations (integral part of the analysis software Astra v.5.3.4.12).

Therapeutic use: The disclosure provides a method for treating, suppressing or preventing diseases associated with TGFbeta signaling. In one embodiment, such disease may be caused or contributed to by dysregulated TGFbeta signaling, by overexpression of TGFbeta or by high levels of bioavailable TGFbeta. Diseases associated with TGFbeta signaling include diseases relating to fibroses of various tissues, such as pulmonary fibrosis including idiopathic pulmonary fibrosis (IPF) and other interstitial lung disease such as acute respiratory distress syndrome (ARDS), fibrosis of the liver including cirrhosis and chronic hepatitis, rheumatoid arthritis, ocular disorders, vascular conditions such as restenosis, fibrosis of the skin including keloid of skin and scarring following wound healing, and kidney such as nephritis, kidney fibrosis and nephrosclerosis or a vascular condition such as restenosis. Other diseases associated with TGFbeta signaling include vascular diseases such as hypertension, pre-eclampsia, hereditary haemorrhagic telangtiectasia type I (HHT1), HHT2, pulmonary arterial hypertension, aortic aneurysms, Marfan syndrome, familial aneurysm disorder, Loeys-Dietz syndrome, arterial tortuosity syndrome (ATS). Other diseases associated with TGFbeta signaling include diseases of the musculoskeletal system such as Duchenne's muscular dystrophy and muscle fibrosis. Further diseases associated with TGFbeta signaling include cancer such as colon, gastric and pancreatic cancer as well as glioma and NSCLC. In addition, the disclosure provides methods for targeting cancer by, for example, modulating TGFbeta signaling in the tumour angiogenesis or through treatment of the cancer stroma. Other diseases or conditions include those related to tissue scarring. Other diseases include pulmonary diseases such as COPD (Chronic obstructive pulmonary disease), liver diseases such as liver failure (e.g. viral hepatitis, alcohol, obesity, autoimmune, metabolic, obstructive), kidney diseases including renal failure (e.g. diabetes, hypertension), hypertrophic cardiomyopathy, transplant rejection (lung/liver/kidney) and hypertrophic and keloid scarring.

"Fibrosis" is the result of excess deposition of extracellular matrix components such as collagen causing overgrowth, scarring and/or hardening of tissues.

The role of TGFbeta in pulmonary fibrosis has been observed (Wynn et al., J. Pathology 2008, 214, p. 199-210; Sime et al. J. Clinical Immunology 1997, Vol. 100, p. 768-776). A shift to increased production of Th2 cytokines and decreased production of Th1 cytokines is observed as a result of unknown lung injury. Overexpression of TGFbeta stimulates angiogenesis, fibroblast activation, deposition of ECM, and fibrogenesis. Animal models (e.g. TGFbeta overexpression, SMAD3 KO, inhibition of TGFbetaR signaling) show that TGFbeta is a key mediator for the development of pulmonary fibrosis.

"Idiopathic pulmonary fibrosis (IPF)" is a chronic and progressive disease resulting in abnormal and excessive deposition of fibrotic tissue in the pulmonary interstitium without a known cause. There is an incidence of approximately 10-20 cases per 100,000 in U.S per year. The prevalence increases sharply with age, reaching 175 cases per 100,000 over the age of 75 with onset usually occurring between 50 and 70 yrs. The five year survival rate is 20% with a mean survival of 2.8 years. Symptoms include a dry cough and progressive breathlessness, abnormal chest x-ray or HRCT and reduced lung volumes. Current treatments include corticosteroids (Prednisone), immunosuppressives (cyclophosphamide) or transplantation although none of the currently available therapies have a proven efficacy. In one embodiment, the single variable domain or polypeptide of the present disclosure provides a treatment for IPF.

Suitably, a successful treatment for Idiopathic pulmonary fibrosis (IPF) will show any one of a decrease in lung fibroblast proliferation, an increase in lung fibroblast apoptosis, a decrease in excessive extracellular matrix synthesis and deposition, an increase in extracellular matrix breakdown and remodelling or will show some protection against ongoing tissue injury and restoration of normal histopathology.

Suitably, a successful treatment would decelerate disease progression.

The efficacy of a treatment for IPF can be demonstrated in the bleomycin induced pulmonary fibrosis model. In one embodiment, the immunoglobulin single variable domain of the present disclosure cross reacts with mouse TGFbetaRII such that its efficacy can be tested in the mouse model.

TGFbeta is an important cell signaling molecule in the modulation of cell behaviour in ocular tissues. Overactivation of TGFbeta is implicated in the pathogenesis of fibrotic diseases in eye tissue which can be wound healing-related and lead to impaired vision and ocular tissue homeostasis (reviewed, for example, by Saika, Laboratory Investigation (2006), 86, 106-115).

Accordingly, in one embodiment, diseases associated with TGFbeta signaling include ocular disorders such as fibrotic diseases of the eye tissue. Fibrotic disease of the eye may occur in the cornea, conjunctiva, lens or retina. Ocular disorders include proliferative vitreoretinopathy (PVR), a disorder of post-retinal detachment and retinal fibrosis, diabetic retinopathy, glaucoma, such as open-angle glaucoma, angle-closure, congenital and pseudo-exfoliation syndrome, wound healing reactions in the lens, such as post chemical or thermal burn, or Stevens-Johnson's syndrome, and post-cataract surgery complications. TGFbeta also has a role in cataract development (Wormstone et al. Exp Eye Res; 83 1238-1245, 2006). A number of ocular disorders occur as a result of fibrosis post surgery. In addition, over activity of TGFbeta2 (transforming growth factor β2) is believed to cause scarring in and around the eye after glaucoma filtration surgery. TGFbeta2 is the predominant isoform involved in pathological scarring of ocular tissues including the cornea, retina, conjunctiva and trabelular meshwork. Scarring or fibrosis of the trabelular meshwork can lead to occlusion of the normal aqueous outflow pathway leading to raised intraocular pressure and risk of glaucoma development. TGFbeta 2 has been shown to be a pathological agent in pre-clinical models of glaucoma disease. TGFbeta2 levels are elevated in patients with glaucoma, in vitro treatment of huTM cells with TGFbeta-2 leads to phenotypic changes and upregulation of ECM modulating proteins (MMP-2, PAI-I) (Lutjen-Drecol (2005), Experimental Eye Research, Vol. 81, Issue 1, pages 1-4; Liton (2005), Biochemical and Biophysical Research Communications Vol. 337, issue 4, p. 1229-1236; Fuchshofer et al (2003), Experimental Eye Research, Vol. 77, issue 6, p. 757-765; Association for Research in Vision and Ophthalmology (ARVO) conference poster #1631 2009). Moreover, overexpression of TGFbeta in the eye leads to glaucoma-like pathology in mice (ARVO conference poster #5108 2009) and delivery of TGFbeta-2 using AAV has been shown to inhibit retinal ganglion cell loss in a rat model of glaucoma (ARVO conference poster #5510 2009). More recently, oxidative stress induction in cultured human optic nerve head astrocytes has been shown to increase TFGbeta2 secretion (Yu et al (2009) Invest. Ophthalmol. Vis. Sci. 50: 1707-1717). This all indicates that reduction of TGFbeta 2 levels might minimize the characteristic optic nerve head changes seen in glaucoma. However, TGFbeta is also known to have an immunosuppressive role and so in some aspects can be protective so a reduction in elevated levels of TGFbeta2 rather than a complete knock down may be preferred in treatment of chronic ocular conditions such as glaucoma. Accordingly, diseases which can be treated using the dAbs and compositions etc. in accordance with the disclosure include scarring post glaucoma filtration surgery.

Accordingly, in one aspect there is provided a method for treating, suppressing or preventing a disease associated with TGFbeta signaling and, in particular, dysregulated TGFbeta signaling, comprising administering to a mammal in need thereof a therapeutically-effective dose or amount of a polypeptide, fusion protein, single variable domain, antagonist or composition according to the disclosure.

In another aspect, the disclosure provides an immunoglobulin single variable domain, polypeptide, ligand or fusion protein in accordance with the disclosure for use as a medicament. Suitable a medicament may comprise an immunoglobulin single variable domain etc. in accordance with the disclosure formatted as described herein.

Suitably, the medicament is a pharmaceutical composition. In a further aspect of the disclosure, there is provided a composition (e.g., pharmaceutical composition) comprising a polypeptide, single variable domain, ligand, composition or antagonist according to the disclosure and a physiologically or pharmaceutically acceptable carrier, diluent or excipient. In one embodiment, the composition comprises a vehicle for delivery. In particular embodiments, the polypeptide, fusion protein, single variable domain, antagonist or composition is administered via pulmonary delivery, such as by inhalation (e.g., intrabronchial, intranasal or oral inhalation, intranasal such as by drops) or by systemic delivery (e.g., parenteral, intravenous, intramuscular, intraperitoneal, intraarterial, intrathecal, intraarticular, subcutaneous, vaginal or rectal administration). In another embodiment, the polypeptide, single variable domain, ligand or fusion protein or compositions in accordance with the disclosure is administered to the eye e.g. by topical administration, as eye drops, particulate polymer system, gel or implant, or by intraocular injection e.g. into the vitreous humour. Delivery can be targeted to particular regions of the eye such as the surface of the eye, or the tear ducts or lacrimal glands or to the anterior or posterior chambers of the eye such as the vitreous humour). It can also be useful if the immunoglobulin single variable domain, composition etc. is delivered to the eye along with an ocular penetration enhancer e.g. sodium caprate or with a viscosity enhancer e.g. Hydroxypropylmethylcellulose (HPMC).

Moreover, the present disclosure provides a method for the treatment of disease using a polypeptide, single variable domain, composition, ligand or antagonist according to the present disclosure. In one embodiment the disease is a tissue fibrosis such as pulmonary fibrosis including Idiopathic pulmonary fibrosis. In another embodiment, the disease is an ocular disorder.

In an aspect of the disclosure, the polypeptide, single variable domain, ligand, composition or antagonist is provided for therapy and/or prophylaxis of a disease or condition associated with TGFbeta signaling in a human. In another aspect, there is provided the use of the polypeptide, single variable domain, composition or antagonist, in the manufacture of a medicament for therapy or prophylaxis of a disease or condition associated with TGFbeta signaling in a human. In another aspect, there is provided a method of treating and/or preventing a disease or condition associated with TGFbeta signaling in a human patient, the method comprising administering the polypeptide, single variable domain, composition or antagonist to the patient. The disclosure also relates to therapeutic methods that comprise administering a therapeutically effective amount of a ligand of the disclosure (e.g., antagonist, or single variable domain) to a subject in need thereof.

In other embodiments, the disclosure relates to a method for treating idiopathic pulmonary fibrosis comprising administering to a subject in need thereof a therapeutically effective amount of a ligand of the disclosure (e.g., antagonist, or single variable domain).

The disclosure also relates to a drug delivery device comprising the composition (e.g., pharmaceutical composition) of the disclosure. In some embodiments, the drug delivery device comprises a plurality of therapeutically effective doses of ligand.

In other embodiments, the drug delivery device is selected from the group consisting of parenteral delivery device, intravenous delivery device, intramuscular delivery device, intraperitoneal delivery device, transdermal delivery device, pulmonary delivery device, intraarterial delivery device, intrathecal delivery device, intraarticular delivery device, subcutaneous delivery device, intranasal delivery device, ocular delivery device, vaginal delivery device, rectal delivery device, syringe, a transdermal delivery device, a capsule, a tablet, a nebulizer, an inhaler, an atomizer, an aerosolizer, a mister, a dry powder inhaler, a metered dose inhaler, a metered dose sprayer, a metered dose mister, a metered dose atomizer, and a catheter.

Suitably, the disclosure provides a pulmonary delivery device containing a polypeptide, single variable domain, composition or antagonist according to the disclosure. The device can be an inhaler or an intranasal administration device. Suitably, the pulmonary delivery device enables delivery of a therapeutically effective dose of a ligand etc. in accordance with the disclosure.

In another embodiment, the disclosure provides an ocular delivery device containing a polypeptide, single variable domain, composition or antagonist according to the disclosure. Suitably, the ocular delivery device enables delivery of a therapeutically effective dose of a ligand etc. in accordance with the disclosure.

As used herein, the term "dose" refers to the quantity of ligand administered to a subject all at one time (unit dose), or in two or more administrations over a defined time interval. For example, dose can refer to the quantity of ligand (e.g., ligand comprising an immunoglobulin single variable domain that binds TGFbetaRII) administered to a subject over the course of one day (24 hours) (daily dose), two days, one week, two weeks, three weeks or one or more months (e.g., by a single administration, or by two or more administrations). The interval between doses can be any desired amount of time.

In one embodiment, the single variable domain of the disclosure is provided as a dAb monomer, optionally unformatted (e.g., not PEGylated or half-life extended) or linked to a PEG, optionally as a dry powder formulation, optionally for delivery to a patient by inhalation (e.g., pulmonary delivery), optionally for treating and/or preventing a lung condition (e.g., Idiopathic pulmonary fibrosis).

The ligands of the disclosure provide several advantages. For example, as described herein, the ligand can be tailored to have a desired in vivo serum half-life. Domain antibodies are much smaller than conventional antibodies, and can be administered to achieve better tissue penetration than conventional antibodies. Thus, dAbs and ligands that comprise a dAb provide advantages over conventional antibodies when administered to treat disease, such as TGFbeta-signaling-mediated disease. In particular, pulmonary delivery of a dAb of the present disclosure to treat idiopathic pulmonary fibrosis enables specific local delivery of an inhibitor of TGFbeta signaling. Advantageously, a unformatted dAb monomer which specifically binds to and inhibits TGFbetaRII is small enough to be absorbed into the lung through pulmonary delivery.

The examples of WO2007085815 are incorporated herein by reference to provide details of relevant assays, formatting and experiments that can be equally applied to ligands of the present disclosure.

Further embodiments of the disclosure are described with reference to the followed examples for the purposes of illustration only.

EXAMPLES

Example 1

Selection of dAbs which Bind TGFbetaRII

Naïve Selections:
4G and 6G naïve phage libraries, phage libraries displaying antibody single variable domains expressed from the GAS1 leader sequence (see WO2005093074) for 4G and additionally with heat/cool preselection for 6G (see WO04101790), were used. The DOM23h leads were isolated by panning pools of VH and VK libraries (identified as 4G H11-19 and 6G VH2-4 (VH dAbs) and 4G κ1, 4G κ2 and 6G κ (Vκ dAbs) against the recombinant human TGF-β RII/Fc chimera protein (R&D systems, Abingdon, UK, cat no. 341-BR). This chimeric protein was made by expression of a DNA sequence encoding the 159-amino acid residue extracellular domain of human TGF-β Receptor Type II (Lin, et al., 1992, *Cell* 68:775-785) fused to the Fc region of human IgG1 in a mouse myeloma cell line, NS0.

The recombinant human TGF-β RII/Fc chimera protein was immobilsed onto a MAXISORP™ [immuno tube (Nunc, Denmark) by coating the tube with 10 μg/ml antigen in phosphate buffered saline (PBS) overnight at 4° C. for the first round of panning. The immunotubes were washed three times with PBS and then blocked to prevent non-specific binding of phage by filling the tube to the brim with 2% MARVEL™ milk powder in PBS (MPBS) and incubated for at least one hour at room temperature. The phage libraries were pooled into six groups; 4G κ1 and κ2, 6G κ, 4G H11-13, 4G H14-16, 4G H17-19 and 6G VH2-4.1×10$^{11}$ phage per library were pooled. The phage were incubated in 4 ml of 2% MPBS for one hour at room temperature. The blocked immunotubes were washed three times with PBS. The blocked phage pools were transferred to the immunotubes and incubated with rotation for at least one hour at room temperature. The immunotubes were washed 10 times with PBS containing 0.1% TWEEN™-20 (PBST) prior to elution of bound phage with 0.5 ml 1 mg/ml trypsin in PBS.

The second round of panning was performed using immunotubes coated with 10 μg/ml human TGF-β RII/Fc. The input phage was pooled as described above, with 1×10$^{10}$ phage per pool and blocked in 0.5 ml 2% MPBS with the addition of 50 μg/ml control Fc fragment. The phage was blocked for one hour at room temperature. 3.5 ml MPBS was added to the phage, which was then transferred to the blocked immunotubes and incubated for at least one hour at room temperature. The immunotubes were washed 20 times with PBST prior to elution of bound phage with 0.5 ml 1 mg/ml trypsin in PBS.

The third round of panning was performed using immunotubes coated with 1 μg/ml Human TGF-β RII/Fc. The input phage was pooled as described above, except the 6G κ and 4G κ1 and κ2 input phage were pooled together. Phage were blocked in 4 ml 2% MPBS with the addition of 100 μg/ml Human IgG Fc fragment (Native IgG Fc fragment derived from human myeloma plasma IgG, Calbiochem, California, US, cat. no. 401104) for at least one hour. The immunotubes were washed 20 times with PBST prior to elution of bound phage with 0.5 ml 1 mg/ml trypsin in PBS. Second and third round outputs were cloned from the fd-phage vector, pDOM4 into pDOM10. Vector pDOM4, is a derivative of the fd phage vector in which the gene III signal peptide sequence is replaced with the yeast glycolipid anchored surface protein (GAS) signal peptide. It also contains a c-myc tag between the leader sequence and gene III, which puts the gene III back in frame. This leader sequence functions well both in phage display vectors but also in other prokaryotic expression vectors and can be universally used. pDOM10 is a plasmid vector designed for soluble expression of dAbs. It is based on pUC119 vector, with expression under the control of the LacZ promoter. Expression of dAbs into the supernatant was ensured by fusion of the dAb gene to the universal GAS leader signal peptide (see WO2005093074) at the N-terminal end. In addition, a FLAG-tag was appended at the C-terminal end of the dAbs. Subcloning of the dAb genes was performed by isolating pDOM4 DNA from the cells infected by the selected dAb-displaying fd-phage using a QIAPREP SPIN MINI-PREP™ kit in accordance with the manufacturer's instructions (cat. no. 27104, Qiagen). The DNA was amplified by PCR using biotinylated oligonucleotides DOM57 (5'-TTG-CAGGCGTGGCAACAGCG-3' (SEQ ID NO: 47) and DOM6 (5'-CACGACGTTGTAAAACGACGGCC-3' (SEQ ID NO: 48), digested with SalI and NotI restriction endonucleases and ligated with pDOM10 digested with SalI and NotI. The ligation products were transformed by electroporation into  E. coli HB2151 cells and plated on TYE plates (Trypton Yeast Extract) supplemented with 100 µg/ml of carbenicillin (TYE-carb). Individual clones were picked and expressed in 96-well plates at 250 rpm, 37° C. overnight, in 0.2 ml/well overnight express auto-induction medium (high-level protein expression system, Novagen) supplemented with 100 µg/ml carbenicillin. These plates were then centrifuged at 1800 g for 10 minutes.

dAb clones that bound human TGF-β RII/Fc were identified by an ELISA. 96-well MAXISORP™ immuno plates (Nunc, Denmark) were coated with human TGF-β RII/Fc overnight at 4° C. The wells were washed three times with PBST and then blocked with 1% TWEEN™ in PBS (1% TPBS) for 1 hour at room temperature. The block was removed and a 1:1 mixture of 1% TPBS and dAb supernatant was added for 1 hour at room temperature. The plate was washed with three times with PBST and the detection antibody (Monoclonal anti-FLAG M2-peroxidase antibody, Sigma-aldrich, UK) was added and incubated for 1 hour at room temperature. The plates were developed using a colourimetric substrate (SUREBLUE™ 1-component TMB Microwell Peroxidase solution, KPL, Maryland, USA) and the optical density (OD) measured at 450 nM, the $OD_{450}$ being proportional to the amount of bound detection antibody.

Positive binders were re-tested in a second, confirmatory ELISA, performed as described above. Human TGF-β RII/Fc-binding dAbs identified in the ELISA were expressed in overnight express autoinduction medium (ONEX™, Novagen) at either 30° C. for 48 to 72 hours, or 37° C. for 24 hours. The cultures were centrifuged (4,600 rpm for 30 minutes) and the supernatants were incubated with STREAMLINE™-protein A beads (Amersham Biosciences, GE HEALTHCARE®, UK. Binding capacity: 5 mg of dAb per ml of beads), either overnight at 4° C. or at room temperature for two hours. The beads were then packed into a UNIFILTER™ 96 well plate (Whatman, GE HEALTHCARE®, UK) and washed with 2×PBS (400 µl per well), followed by centrifugation at 1000 rpm for 2 minutes at room temperature. The washing procedure was repeated once more with 2×PBS, followed by a final wash with 10 mM Tris-HCl pH 8.0 (Sigma, UK). Bound dAbs were eluted by adding 0.1 M glycine-HCl, pH 2.0 (210 µl per well) (Sigma, UK), followed by centrifugation. The flow through was collected in a 96-well round-bottom plate (CORNING COSTAR™) placed beneath the UNIFILTER™ plate. The wells of the 96 well round-bottom plate contained 40 µl 1 M Tris pH 8.0 (Sigma, UK) so as to neutralize the eluted dAbs. The elution procedure was repeated once more. Alternatively, the STREAMLINE™-protein A beads were packed into a chromatography column and washed with 2×PBS, followed by 10 mM Tris-HCl pH 7.4 (Sigma, UK). Bound dAbs were eluted with 0.1 M glycine-HCl pH 2.0 and neutralized with 1M Tris pH 8.0. The OD at 280 nm of the dAbs was measured and protein concentrations were determined using extinction coefficients calculated from the amino acid compositions of the dAbs.

dAbs were tested for potency, as measured in the A549 IL-11 release assay and biophysical characteristics, as assessed by SEC-MALLS and DSC (as described below). DOM23h-33 (SEQ ID NO: 1), DOM23h-251 (SEQ ID NO: 2), DOM23h-262 (SEQ ID NO: 3), DOM23h-271 (SEQ ID NO: 4), DOM23h-348 (SEQ ID NO: 5), DOM23h-435 (SEQ ID NO: 6), DOM23h-436 (SEQ ID NO: 7), DOM23h-437 (SEQ ID NO: 8), DOM23h-438 (SEQ ID NO: 9), DOM23h-439 (SEQ ID NO: 10), and DOM23h-440 (SEQ ID NO: 11) libraries were selected for error-prone affinity maturation.

Example 2

Error Prone Affinity Maturation

Error-prone mutagenesis of DOM23h-33 (SEQ ID NO: 1), DOM23h-251 (SEQ ID NO: 2), DOM23h-262 (SEQ ID NO: 3), DOM23h-271 (SEQ ID NO: 4), DOM23h-348 (SEQ ID NO: 5), DOM23h-435 (SEQ ID NO: 6), DOM23h-436 (SEQ ID NO: 7), DOM23h-437 (SEQ ID NO: 8), DOM23h-438 (SEQ ID NO: 9), DOM23h-439 (SEQ ID NO: 10), and DOM23h-440 (SEQ ID NO: 11) was performed to improve the affinity of these dAbs.

Phage Library Construction:

Error prone libraries of DOM23h-33 (SEQ ID NO: 1), DOM23h-251 (SEQ ID NO: 2), DOM23h-262 (SEQ ID NO: 3), DOM23h-271 (SEQ ID NO: 4), DOM23h-348 (SEQ ID NO: 5), DOM23h-435 (SEQ ID NO: 6), DOM23h-436 (SEQ ID NO: 7), DOM23h-437 (SEQ ID NO: 8), DOM23h-438 (SEQ ID NO: 9), DOM23h-439 (SEQ ID NO: 10), and DOM23h-440 (SEQ ID NO: 11) were made using GENEMORPH® II Random Mutagenesis kit (Stratagene, Cat No 200550). The target dAb genes were amplified by PCR using Taq DNA polymerase and oligonucleotides DOM008 (5'-AGCGGATAACAATTTCACACAGGA-3' (SEQ ID NO: 49)) and DOM009 (5'-CGCCAGGGTTTTCCCAGTCAC-GAC-3' (SEQ ID NO: 50)), followed by re-amplification of the diluted PCR product with oligonucleotides DOM172 (5' TTGCAGGCGTGGCAACAGCG-3' (SEQ ID NO: 51)) and DOM173 (5'-CACGACGTTGTAAAACGACGGCC-3' (SEQ ID NO: 52)), and MUTAZYME™ II DNA polymerase, according to manufacturer's instructions. This PCR product was further amplified using Taq DNA polymerase and oligonucleotides DOM172 and DOM173, to increase the DNA product yield. The PCR product was digested with Sal I and Not I restriction endonucleases. Undigested product and digested ends were removed from the digested product using streptavidin beads (Dynal Biotech, UK). The digested product was ligated into pDOM4 phage vector digested with Sal I and Not I restriction endonucleases and used to transform  E. coli TB1 cells. The transformed cells were plated on 2×TY agar supplemented with 15 µg/ml tetracycline, yielding library sizes of >1×10$^7$ transformants.

Error-Prone Selections:

Four rounds of selection were performed with the DOM23h-33, DOM23h-251, DOM23h-262, DOM23h-271 and DOM23h-348 libraries against 100, 5, 0.5 and 0.1 nM biotinylated human TGF-β RII/Fc, respectively. Four rounds of selection were performed with the DOM23h-435, DOM23h-436, DOM23h-437, DOM23h-438, DOM23h-439 and DOM23h-440 error-prone libraries against 100, 10, 1 and 0.1 nM biotinylated human TGF-β RII/Fc, respectively. The human TGF-β RII/Fc was biotinylated using a five fold molar excess of EZ-LINK™ Sulfo-NHS-LC-Biotin reagent (Pierce, Rockford, USA) (Henderikx, et al., 2002, Selection of antibodies against biotinylated antigens. Antibody Phage Display: Methods and protocols, Ed. O'Brien and Atkin, Humana Press). Third and fourth round selection outputs were subcloned into the pDOM10 vector, as described above. Individual clones were picked and expressed in 96 well plates at 850 rpm, 37° C. for 24 hours, 90% humidity in 0.5 ml/well overnight express auto-induction medium supplemented with 100 µg/ml carbenicillin. Plates were then centrifuged at 1800 g for 10 minutes. Supernatants were diluted either ⅕ or ½ in HBS-EP buffer and screened on BIACORE™ for binding to biotinylated human TGF-β RII/Fc (SA chip coated with 1000 Ru biotinylated hRII-Fc in accordance with the manufacturer's recommendations) (BIACORE™, GE HEALTHCARE®). Samples were run on BIACORE™ at a flow rate of 50 µl/min. Clones that bound with a high number of resonance units (RUs) or with an improved off-rate compared to the parent clone were expressed in 50 ml overnight express autoinduction medium at 30° C. for 48 to 72 hours and centrifuged at 4,600 rpm for 30 minutes. The supernatants were incubated overnight at 4° C. with STREAMLINE™-protein A beads. The beads were then packed into drip columns, washed with 5 column volumes of 2×PBS, followed by one bed volume of 10 mM Tris-HCl pH 7.4 and bound dAbs were eluted in 0.1 M glycine-HCl, pH 2.0 and neutralised with 1 M Tris-HCl, pH 8.0. The OD at 280 nm of the dAbs was measured and protein concentrations were determined using extinction coefficients calculated from the amino acid compositions of the dAbs.

Example 3

Introduction of K61N D64R Mutation into dAb Sequences

The D61N and K64R double mutation were introduced into dAbs belonging to the DOM23h-271, 437 and 439 lineages in an attempt to improve potency. dAbs containing these mutations were isolated from the selections performed with the DOM23h-262 error-prone phage library and were found to be more potent than DOM23h-262 (SEQ ID NO: 3) as measured in the A549 IL-11 release assay. The presence of D61N (as well as Y102H) in DOM23h-262-6 (SEQ ID NO: 12) improved dAb potency 54-fold relative to DOM23h-262 (SEQ ID NO: 3), and the presence of D61N and K64R (as well as Q39R, E53D and W103S) in DOM23h-262-10 (SEQ ID NO: 13) improved potency 540-fold relative to DOM23h-262 (SEQ ID NO: 3), as determined in the A549 IL-11 release assay (Table 1).

The mutations were introduced into the dAbs belonging to the DOM23h-271, DOM23h-437 and DOM23h-439 lineages by overlap extension using the polymerase chain reaction (PCR) (Ho, et al., Gene 1989 77(1)); complementary oligonucleotide primers are used to generate two DNA fragments having overlapping or complementary ends. These fragments are combined in a subsequent assembly PCR in which the overlapping ends anneal, allowing the 3' overlap of each strand to serve as a primer for the 3' extension of the complementary strand and the resulting fusion product is amplified further by PCR. Specific alterations in the nucleotide sequence can be introduced by incorporating nucleotide changes into the overlapping oligonucleotide primers. The target dAb gene fragments were amplified by two separate PCRs using Taq DNA polymerase and oligonucleotide pairs DOM008 (flanks 5' start of dAb gene) and CD131 (5'-GAACCGGCCCCTCACGGAGTTTGCGTAGTA-3' (SEQ ID NO: 53)) or DOM009 (flanks 3' end of dAb gene) and CD130 (5'-TACTACGCAAACTCCGTGAGGGGCCGGTTC-3' (SEQ ID NO: 54)) (mutated nucleotide residues underlined). The two PCR fragments were recombined in an assembly PCR using Taq DNA polymerase without the addition of primers. The fusion product was then amplified by the addition of flanking primers DOM008 and DOM009 to the PCR reaction. The PCR products were digested with Sal I and Not I restriction endonucleases and ligated into pDOM10 or 13 expression vectors digested with Sal I and Not I restriction endonucleases and used to transform E. coli HB2151 cells. pDOM13 expression vector has an identical nucleotide sequence to pDOM10, except the FLAG epitope nucleotide sequence is replaced by two stop codons (5'-TAA TAA-3'), resulting in expression of soluble dAbs without a C-terminal FLAG tag. The D61N and K64R nucleotide mutations were introduced into DOM23h-271-3 (SEQ ID NO: 14), DOM23h-271-7 (SEQ ID NO: 15) and DOM23h-437-6 (SEQ ID NO: 19), creating DOM23h-271-12 (SEQ ID NO: 16), DOM23h-271-13 (SEQ ID NO: 17) and DOM23h-437-9 (SEQ ID NO: 21), respectively. DOM23h-437-4 (SEQ ID NO: 18) and DOM23h 439-6 (SEQ ID NO: 22) were isolated from the error prone selection outputs already containing the K64R mutation. The D61N mutation was introduced into these two dAbs to create DOM23h-437-8 (SEQ ID NO: 20) and DM23h-439-8 (SEQ ID NO: 23), respectively.

Example 4

Assays for TGF-βRII Inhibition

The dAbs were tested in the A549 IL-11 release cell assay and SBE-bla HEK 293T cell sensor assay.

A549 IL-11 Release Assay:

The A549 Interleukin-11 (IL-11) release assay measures the ability of dAbs to inhibit human TGF-β1 stimulated IL-11 release from A549 cells. TGF-β1 binds directly to TGF-βRII and induces the assembly of the TGF-βRI/II complex. TGF-βRI is phosphorylated and is able to signal through several pathways including the Smad4 pathway. Activation of the Smad4 pathway results in the release of IL-11. The IL-11 is secreted into the cell supernatant and is then measured by colourmetric ELISA.

Soluble dAbs were tested for their ability to block TGF-β1 signalling via the Smad4 pathway. Briefly, $1 \times 10^5$ A549 cells per well in assay medium (DMEM high glucose medium (GIBCO™, Invitrogen Ltd, Paisley, UK), 10% heat inactivated foetal calf serum (PAA, Austria), 10 mM HEPES (Sigma, UK) and 1% penicillin/streptomycin (PAA, Austria)) were added to a tissue culture 96 well plate (Nunc), followed by the dAb and TGF-β1 (final concentration 3 ng/ml) (R&D Systems, Abingdon, UK) and incubated overnight at 37° C., 5% $CO_2$. dAbs were dialysed into PBS prior to being assayed. The concentration of IL-11 released into the supernatant is measured using a Human IL-11 DUOSET™ (R&D systems, Abingdon, UK), in accordance with the manufacturer's instructions.

The results are summarised in Table 1.

SBE-Bla HEK 293T Cell Sensor Assay:

Members of the Smad family of signal transduction molecules are components of an intracellular pathway that transmits TGF-β signals from the cell surface to nucleus. TGF-β1 binds directly to TGF-βRII and induces the assembly of the TGF-βRI/II complex. Smad2 and Smad3 are then phosphorylated by TGF-βRI, and subsequently form a heteromeric complex with the co-smad family member Smad4. These complexes are translocated to the nucleus where they bind DNA and regulate gene transcription.

Cell Sensor SBE-bla HEK 293T cells contain a beta-lactamase reporter gene under control of the Smad binding element (SBE) which was stably integrated into HEK 293T cells (Invitrogen, UK). The cells are responsive to TGF-β1 and can be used to detect agonists/antagonists of the Smad2/3 signaling pathway.

Soluble dAbs were tested for their ability to block TGF-β1 signaling via this pathway following the manufacturer's recommended protocol (Invitrogen, UK). dAbs were dialysed into PBS prior to being assayed.

The results are summarised in Table 1.

TABLE 1

| | A549 IL-11 release assay | | SBE-bla HEK 293T Cell Sensor assay | |
|---|---|---|---|---|
| | $IC_{50} \pm S.D$ (nM) | n | $IC_{50} \pm S.D$ (nM) | n |
| DOM23h-262 | 8931.3 ± 3822 | 2 | | |
| DOM23h-262-6 | 165.6 ± 24 | 2 | 164.6 ± 1.1 | 2 |
| DOM23h-262-10 | 16.5 ± 3 | 2 | 13.8 ± 3.1 | 2 |
| DOM23h-271 | 10070.2 ± 5685 | 2 | 3495.6 | 1 |
| DOM23h-271-3 | 354.3 ± 61 | 3 | 360.0 ± 423.6 | 3 |
| DOM23h-271-7 | 994.6 ± 92 | 3 | 378.9 ± 57.5 | 2 |
| DOM23h-271-12 | 5.3 ± 1 | 6 | 7.7 | 1 |
| DOM23h-271-13 | 21.5 ± 8 | 3 | 7.7 ± 2.6 | 3 |
| DOM23h-437 | 270.4 ± 79 | 6 | | |
| DOM23h-437-4 | 66.9 ± 28 | 3 | | |
| DOM23h-437-6 | 649.4 ± 152 | 3 | | |
| DOM23h-437-7 | 6.7 | 1 | 0.9 ± 0.4 | 2 |
| DOM23h-437-8 | 6.5 | 1 | | |
| DOM23h-437-9 | 3.6 ± 0.6 | 3 | 0.7 ± 0 | 2 |
| DOM23h-439 | 3137.3 ± 539 | 4 | 1106.6 | 1 |
| DOM23h-439-6 | 448.4 ± 9 | 2 | 362.9 ± 179.4 | 3 |
| DOM23h-439-7 | 24.8 ± 17 | 2 | 4.47 | 1 |
| DOM23h-439-8 | 9.4 ± 6 | 2 | 4.5 ± 0.5 | 3 |

Individual A549 IL-11 release assays were performed in duplicate and a single dose-response curve and $IC_{50}$ value determined per assay (n=1). The assay was performed between one and six times and the mean $IC_{50}$ values (n=1 to 6)±standard deviation (S.D) are summarised in Table 1. Individual SBE-bla HEK 293T cell sensor assays were performed in duplicate and two dose-response curves and two $IC_{50}$ values determined per assay. The mean of the duplicate $IC_{50}$ values was calculated to produce a single $IC_{50}$ value per assay (n=1). The assays were performed between one and three times (n=1 to 3) and the mean of the $IC_{50}$ values±standard deviation (S.D) was calculated and summarised in Table 1.

A549 Phospho-Smad MSD Assay:

This assay measures the ability of dAbs to inhibit the TGF-β1 stimulated phosphorylation of Smad3 in A549 cells, a human alveolar basal epithelial cell line. TGF-β1 binds directly to TGF-βRII and induces the assembly of the TGF-βRI/II complex. TGF-βRI is phosphorylated, and, in turn, Smad2 and Smad3 become phosphorylated.

Levels of phosphorylated Smad2/3 can be measured in cell lysates using an anti-Smad2/3 capture antibody and a ruthenylated-anti-Smad3 detection antibody and measured by electrochemiluminescence assay.

Soluble dAbs were tested for their ability to block TGF-β1 signaling via this pathway Briefly, $2 \times 10^4$ A549 cells per well in growth medium (DMEM F12 with 10% heat inactivated Foetal calf serum (Invitrogen, UK) supplemented with 25 mM HEPES (Invitrogen, UK) and 1% GLUTAMAX™ (Invitrogen, UK)) were added to a black, clear bottomed tissue culture 384 well plate (Greiner Bio-one, UK) and incubated overnight at 37° C., 5% $CO_2$. dAbs were buffer exchanged into Tris-buffered saline pH 8.0 (TBS) (Sigma, UK) prior to being assayed. dAbs were then diluted in growth medium, added to the cells and incubated for 1 hour at 37° C., (5% CO2). This was followed by the addition TGF-β1 (diluted in DMEM medium (Invitrogen, UK) supplemented with 25 mM HEPES and 1% GLUTAMAX™) and incubated for 30 minutes at 37° C. The concentration of TGF-β1 used was equal to the $EC_{80}$ value (concentration which results in 80% maximal response) for TGF-β1 stimulation of A549 cell growth. The concentration of TGF-β1 typically used was 2.2 ng/ml. The cells were lysed in lysis buffer (Cell Signaling Technology, MA, U.S.A) supplemented with phosphatase inhibitors (Sigma, Poole, UK) and protease inhibitors (Roche) for twenty minutes at 4° C. The cell lysates were transferred to 384 well high bind MSD plates (Meso Scale Discovery, MD, U.S.A) and incubated for three hours at room temperature. The MSD plates had previously been spotted with 60 µg/ml biotinylated Smad2/3 (BD Biosciences, Oxford, UK) and blocked with TBS containing 5% MARVEL™ dried milk powder and 0.1% TWEEN™ 20 (Sigma, UK) (MTTBS) overnight at 4° C. and washed once with TBS containing 0.1% TWEEN™ 20 (TTBS). The cell lysates were removed, the plate washed three times with TTBS, followed by the addition of ruthenylated anti-phospho Smad3 antibody (Cell Signaling Technology MA, USA). The anti-phospho Smad3 antibody was labeled with MSD TAG-NHS-Ester (Ruthenium (II) tris-bipyridine) (Meso Scale Discovery, MD, USA)), according to the manufacturer's instructions. The plate was incubated for eighteen hours at room temperature. The plate was washed once with TTBS and Read buffer T (Meso Scale Discovery, MD, USA), supplemented with surfactant (Meso Scale Discovery, MD, USA), was added. The plates were read using a MSD SECTOR™ imager 6000 (Meso Scale Discovery, MD, USA). It would be possible to perform this assay with other relevant cell lines such as primary lung fibroblasts.

Results of the assay data obtained of DOM23h dAbs are summarized in Table 2.

RAW 264.7 Phospho-Smad Assay:

This assay measures the ability of dAbs to inhibit the TGF-β1 stimulated phosphorylation of Smad3 in RAW264.7 cells, a mouse macrophage cell line. TGF-β1 binds directly to TGF-βRII and induces the assembly of the TGF-βRI/II complex. TGF-βRI is phosphorylated and in turn Smad2 and Smad3 become phosphorylated. Levels of phosphorylated Smad2/3 can be measured in cell lysates using an anti-Smad2/3 capture antibody and a ruthenylated-anti-Smad3 detection antibody and measured by electrochemiluminescence assay.

Soluble dAbs were tested for their ability to block TGF-β1 signaling via this pathway Briefly, $3.45 \times 10^5$ RAW 264.7 cells per well in growth medium (high glucose DMEM (Invitrogen, UK) supplemented with 10% heat inactivated foetal calf serum (Invitrogen, UK) and 0.01% pluronic acid (Sigma, UK)) were added to a tissue culture 96 well plate (CORNING COSTAR™) and incubated for two days at 37° C., 5% $CO_2$. dAbs were buffer exchanged into TBS prior to being assayed. dAbs were subsequently diluted in growth media, added to the cells and incubated for 1 hour at 37° C., (5% CO2), followed by the addition TGF-β1 (diluted in DMEM (Invitrogen, UK) supplemented with 25 mM Hepes (Invitrogen, UK) and incubated for 30 minutes at 37° C. The concentration of TGF-β1 used was equal to the $EC_{80}$ value (concentration which results in 80% maximal response) of TGF-β1 stimulation of RAW 264.7 cell growth. The concentration of TGF-β1 typically used was 1.1 ng/ml. The cells were lysed in lysis buffer supplemented with phosphatase and protease inhibitors for twenty minutes at 4° C. The cell lysates were transferred to 384-well high bind MSD plates (Meso Scale Discovery, MD, USA) and incubated for three hours at room temperature. The MSD plates had previously been spotted with 60 µg/ml biotinylated Smad2/3 and blocked with MTTBS overnight at 4° C. and washed once with TTBS. The cell lysates were removed, the plate washed three times with TTBS and ruthenylated-anti-phospho Smad3 antibody added to the plate and incubated for eighteen hours at room temperature. The anti-phospho Smad3 antibody was labeled with MSD TAG-NHS-Ester (Ruthenium (II) tris-bipyridine) (Scale Discovery, MD, USA)), according to the manufacturer's instructions. The plate was washed twice with TTBS and Read buffer T supplemented with surfactant, was added. The plates were read using a MSD SECTOR™ imager 6000.

Results of the assay data obtained of DOM23h dAbs are summarized in Table 2.

|  | A549 phospho-Smad assay | | RAW 264.7 phospho-Smad assay | |
| --- | --- | --- | --- | --- |
|  | $IC_{50} \pm S.E$ | $IC_{50}$ range (nM) | n | $IC_{50}$ range (nM) | n |
| DOM23h-271-12 | 32.4 ± 8.6 | 3.2-108.5 | 17 | 67-2884 | 19 |
| DOM23h-437-9 | 6.1 ± 1.9 | 1.6-15.0 | 8 | Inactive | 10 |
| DOM23h-439-8 | 30.04 ± 6.7 | 7.2-49.2 | 7 | Inactive | 10 |

Individual A549 phospho-Smad MSD assays were performed in either singlet, duplicate or triplicate and one, two or three dose-response curves and $IC_{50}$ values, respectively determined per assay (n=1, 2 or 3). DOM23h-271-12 (SEQ ID NO: 16) was tested in seven assays, four times in duplicate and three times in triplicate (n=17). DOM23h-437-9 (SEQ ID NO: 21) was tested in three assays, once in duplicate and twice in triplicate (n=8). DOM23h-439-8 (SEQ ID NO: 23) was tested in three assays, twice in triplicate and once in singlet (n=7). The mean of the $IC_{50}$ values±standard error (S.E) was calculated and summarised in Table 2.

Individual RAW 264.7 phospho-Smad assays were performed in either singlet, duplicate or triplicate and one, two or three dose-response curves and $IC_{50}$ values determined per assay (n=1, 2 or 3). DOM23h-271-12 (SEQ ID NO: 16) was tested in seven assays, once in singlet, six times in duplicate and twice in triplicate (n=19). The range of $IC_{50}$ values obtained is summarised in Table 2. DOM23h-437-9 (SEQ ID NO: 21) and DOM23h-439-8 (SEQ ID NO: 23) were both tested five times in duplicate (n=10).

MC3T3-E1 Luciferase Assay:

The MC3T3-E1 luciferase assay measures the ability of dAbs to inhibit TGFβ-induced expression of CAGA-luciferase in MC3T3-E1 cells. Three copies of a TGFβ-responsive sequence motif, termed a CAGA box are present in the human PAI-1 promoter and specifically bind Smad3 and 4 proteins. Cloning multiple copies of the CAGA box into a luciferase reporter construct confers TGFβ responsiveness to cells transfected with the reporter system. This assay uses MC3T3-E1 cells (mouse osteoblasts) stably transfected with a $[CAGA]_{12}$-luciferase reporter construct (Dennler, et al. (1998) *EMBO J.* 17, 3091-3100).

Soluble dAbs were tested for their ability to block TGF-β1 signalling via the Smad3/4 pathway. Briefly, $2.5 \times 10^4$ MC3T3-E1 cells per well in assay medium (RPMI medium (GIBCO™, Invitrogen Ltd, Paisley, UK), 10% heat inactivated foetal calf serum, and 1% penicillin/streptomycin) were added to a tissue culture 96 well plate (Nunc), followed by the dAb and TGF-β1 (final concentration 1 ng/ml) and incubated for six hours at 37° C., 5% $CO_2$. dAbs were dialysed into PBS prior to being tested in the assay. BRIGHTGLOW™ luciferase reagent (Promega, UK) was added to the wells and incubated at room temperature for two minutes to allow the cells to lyse, and the resulting luminescence measured on a luminometer.

DOM23h-271-12 (SEQ ID NO: 16), DOM23h-437-9 (SEQ ID NO: 21) and DOM23h-439-8 (SEQ ID NO: 23) were tested in The MC3T3-E1 luciferase assay. The results are shown in Table 3.

TABLE 3

| | MC3T3-E1 luciferase assay | | |
| --- | --- | --- | --- |
| dAb | $IC_{50}$ range (nM) | $IC_{50} \pm S.D$ | n |
| DOM23h-271-12 Batch CD200308 | 1077-2442 | 1760 ± 965 | 2 |
| DOM23h-271-12 Batch CD210408 | 1.48-16.10 | 8.84 ± 8.4 | 4 |
| DOM23h-437-9 | 136-832 | | 2 |
| DOM23h-439-8 | inactive | | 3 |

Individual MC3T3-E1 luciferase assays were performed in duplicate and an $IC_{50}$ value determined (n=1). The assay was performed between two and four times (n=2 to 4) and range of $IC_{50}$ values are summarised in Table 3. The results obtained for DOM23h-271-12 (SEQ ID NO: 16) varied according to the dAb batch number tested. Therefore, the range of $IC_{50}$ values and the mean $IC_{50}$ value±standard deviation (S.D) were calculated for each batch number and summarised in Table 3.

Example 5

DSC (Differential Scanning Calorimetry)

The thermal stability of the dAbs was determined using differential scanning calorimeter (DSC). dAbs were tested at 1 mg/ml in PBS buffer. Proteins were dialysed overnight into PBS buffer. PBS buffer was used as a reference for all samples. DSC was performed using capillary cell microcalorimeter VP-DSC (Microcal, MA, USA), at a heating rate of 180° C./hour. A typical scan was from 25-90° C. for both the reference buffer and the protein sample. After each reference buffer and sample pair, the capillary cell was cleaned with a solution of 1% DECON™ (Fisher-Scientific) in water followed by PBS. Resulting data traces were analysed using ORIGIN 7 MICROCAL™ software. The DSC trace obtained from the reference buffer was subtracted from the sample trace. The precise molar concentration of the sample was entered into the data analysis routine to yield values for melting temperature (Tm), enthalpy (ΔH) and van't Hoff enthalpy (ΔHv) values. Data were fitted to a non-2-state model with both 1 and 2 transition events (or peaks).

Apparent melting temperatures (app Tm) were obtained for both models with the app Tms from the best fitting model summarised in Table 4. The melting temperatures (Tm) of the dAbs ranged from 48.3° C. to 62.9° C. The additional D61N and K64R mutations present in DOM23h-271-12 (SEQ ID NO: 16) and DOM23h-271-13 (SEQ ID NO: 17) decrease thermal stability of the protein relative to DOM23h-271-3 (SEQ ID NO: 14) and DOM23h-271-7, respectively; a difference of 4° C. for the DOM23h-271-3 (SEQ ID NO: 14) and DOM23h-271-12 (SEQ ID NO: 16) pair and 2° C. for DOM23h-271-7 (SEQ ID NO: 15) and DOM23h-271-13 (SEQ ID NO: 17) pair. The additional D61N and K64R mutations present in DOM437-9 also decrease the thermal stability of the protein compared to the same sequence minus these mutations (DOM23h-437-6 (SEQ ID NO: 19)) by at least 4° C. The addition of the D61N and K64R mutations to DOM23h-439 to create DOM23h-439-7 results in a reduction of thermal stability of approximately 2° C. Similarly, the addition of the D61N mutation to DOM23h-439-6 (SEQ ID NO: 22), a dAb that contains the K64R mutation results in a decrease in thermal stability of approximately 2° C. These data, which are set forth in Table 4, suggest that the D61N K64R mutation has a negative effect upon the thermal stability of DOM23h dAbs.

TABLE 4

| | DSC Apparent Tm ° C. | | |
|---|---|---|---|
| | 1 peak fit | 2 peak fit | |
| dAb | Tm | Tm1 | Tm2 |
| DOM23h-271 | 60.4 (n = 1) | | |
| DOM23h-271-3 | 55.3-54.6 (n = 2) | | |
| DOM23h-271-7 | | 58.9-59.0 | 61.8 (n = 2) |
| DOM23h-271-12 | 48.3-50.5 (n = 2) | | |
| DOM23h-271-13 | | 55.5 | 59.7 (n = 1) |
| DOM23h-437 | | 59.3 | 61.2 n = 1) |
| DOM23h-437-4 | 61.7 (n = 1) | 60.5 | 62.9 (n = 1) |
| DOM23h-437-6 | 61.7 (n = 1) | 58.3 | 60.2 (n = 1) |
| DOM23h-437-8 | | 57.9 | 59.5 (n = 1) |
| DOM23h-437-9 | | 51.7-54.0 | 54.4-55.7 (n = 2) |
| DOM23h-439 | 58.4 (n = 1) | | |
| DOM23h-439-6 | 58.0 (n = 1) | | |
| DOM23h-439-7 | | 55.5 | 56.8 (n = 1) |
| DOM23h-439-8 | | 52.2 | 56.3 (n = 1) |

Example 6 dAb Expression dAbs belonging to the DOM23h-271, 437, and 439 lineages were expressed as described before. DOM23h-271 (SEQ ID NO: 4) expressed well, with an expression level of 72 mg/l (Table 5). DOM23h-271-3 (SEQ ID NO: 14) and DOM23h-271-7 (SEQ ID NO: 15), which were isolated from the error prone mutation selection outputs, also expressed well, with expression levels comparable to the parental DOM23h-271 dAb (63 mg/l for DOM23h-271-3 (SEQ ID NO: 14) and 71 mg/l for DOM23h-271 (SEQ ID NO: 4) (Table 5)). The introduction of D61N and K64R mutations into DOM23h-271-3 (SEQ ID NO: 14), to create DOM23h-271-12 (SEQ ID NO: 16), resulted in a 7 fold reduction in expression level (Table 5). The introduction of the same mutations into DOM23h-271-7, creating DOM23h-271-13 (SEQ ID NO: 17), reduced the dAb expression level by 2.5 fold (Table 5).

The introduction of the D61N and K64R mutations into dAbs from DOM23h-437 lineage had a similar effect as described above. DOM23h-437 (SEQ ID NO: 8), DOM23h-437-4 (SEQ ID NO: 18) and DOM23h-437-6 (SEQ ID NO: 19) all expressed well, with expression levels of 89, 66 and 98 mg/l, respectively (Table 5). However, the introduction of the D61N and K64R mutations into these dAbs resulted in a 1.7 to 2.5 fold reduction in expression level (Table 5). The introduction of the D61N and K64R mutations into DOM23h-439 (SEQ ID NO: 10) and DOM23h-439-8 (SEQ ID NO: 23) had a similar effect, with the expression levels of these dAbs being reduced by 1.8 and 4.6 fold, respectively (Table 5).

TABLE 5

| dAb | Vector | Expression level (mg/l) | n |
|---|---|---|---|
| DOM23h-271 | pDOM10 | 72 | 4 |
| DOM23h-271-3 | pDOM10 | 63 | 2 |
| DOM23h-271-7 | pDOM10 | 71 | 1 |
| DOM23h-271-12 (=DOM23h-271-3 + D61N + K64R) | pDOM13 | 9 | 2 |
| DOM23h-271-13 (=DOM23h-271-7 + D61N + K64R) | pDOM13 | 28 | 2 |
| DOM23h-437 | pDOM10 | 89 | 2 |
| DOM23h-437-4 | pDOM10 | 66 | 2 |
| DOM23h-437-6 | pDOM10 | 98 | 2 |
| DOM23h-437-7 (=DOM23h-437 + D61N + K64R) | pDOM10 | 35 | 1 |
| DOM23h-437-8 (=DOM23h-437-4 + D61N + K64R) | pDOM10 | 32 | 1 |
| DOM23h-437-9 (=DOM23h-437-6 + D61N + K64R) | pDOM10 | 57 | 2 |
| DOM23h-439 | pDOM10 | 97 | 2 |
| DOM23h-439-6 | pDOM10 | 123 | 2 |
| DOM23h-439-7 (=DOM23h-439 + D61N + K64R) | pDOM10 | 54 | 1 |
| DOM23h-439-8 (=DOM23h-439-6 + D61N + K64R) | pDOM10 | 27 | 1 | dAbs in pDOM10 or pDOM13 expression vectors, transformed into HB2151 cells, were expressed in overnight express autoinduction medium at 30° C. for 48 to 72 hours. STREAMLINE™ protein A beads were added to the culture supernatant to bind the soluble VH dAbs. The beads were washed with 2×PBS and the bound dAb eluted with 0.1M glycine pH 2.0 and neutralized with 1M Tris pH 8.0. The OD at 280 nm of the dAbs was measured and protein concentrations were determined using extinction coefficients calculated from the amino acid compositions of the dAbs.

Example 7

Competition BIACORE™

Experiments were performed to investigate whether or not dAbs from the DOM23h-271, 437 and 439 lineages compete with each other for the same or different binding sites on hTGFβ-RII using surface plasmon resonance (SPR). The SPR experiments were performed on a BIACORE™ 3000 instrument (BIACORE™, GE HEALTHCARE®, Sweden). hTGFb-RII/Fc antigen at 50 ug/ml in 10 mM sodium acetate buffer, pH 4 (BIACORE™, GE HEALTHCARE®, Sweden) was coupled to a CM5 sensor chip (BIACORE™, GE HEALTHCARE®, Sweden), according to the manufacturer's instructions. Approximately 5500 RUs of antigen were coupled. A blank flow cell was used as a reference. Purified dAbs were diluted in HBS-EP buffer (BIACORE™, GE HEALTHCARE®, Sweden) and flowed over the antigen-coated and blank flow cells at a rate of 30 μl/minute using the co-inject command. The coinject command allows the injection of a second sample immediately after the first one. The first injection consisted of a single dAb and the second injection consisted of a mixture of the first dAb and a second dAb. All dAbs were used at concentrations high enough to bind the antigen surface with maximal capacity. If the maximal binding capacity of the antigen surface by the first dAb can be exceeded by injecting the mixture of the two dAbs, the second dAb is likely to compete for a different binding site or epitope on the antigen. If no further binding is observed following the second injection, then the two dAbs are likely to compete for the same antigen binding site. Results are easier to interpret if the most potent or highest affinity dAb is injected first. The surface of the CM5 sensor chip was regenerated after a coinject cycle using 10 mM glycine pH 2.25 (two 10 μl injections), followed by a 5-minute wait period.

Competition BIACORE™ experiments were performed by co-injecting DOM23h-437-6 (SEQ ID NO: 19), DOM23h-271-3 (SEQ ID NO: 14) and DOM23h-439-6 (SEQ ID NO: 22) individually and in combination with each other. These clones were isolated following selections with the error prone maturation libraries. They do not contain the D61N K64R double mutation, although DOM23h-439-6 (SEQ ID NO: 22) does contain the K64R single mutation. DOM23h-437-6 (SEQ ID NO: 19) is the most potent of the three dAbs and as such was injected first, at 100 nM, followed by a mixture of DOM23h-437-6 (SEQ ID NO: 19) (100 nM) and DOM23h-271-3 (SEQ ID NO: 14) (500 nM) (FIG. 8A) or DOM23h-437-6 (SEQ ID NO: 19) (100 nM) and DOM23h-439-6 (SEQ ID NO: 22) (500 nM) (FIG. 8B). More RUs of dAb bound during the second injection, suggesting DOM23h-437-6 (SEQ ID NO: 19) competes for a different antigen binding site compared to DOM23h-271-3 (SEQ ID NO: 14) and DOM23h-439-6 (SEQ ID NO: 22).

Competition BIACORE™ experiments were performed by co-injecting DOM23h-437-9 (SEQ ID NO: 21) in combination with DOM23h-262-10 (SEQ ID NO: 13), DOM23h-271-12 (SEQ ID NO: 16) and DOM23h-439-8 (SEQ ID NO: 23). These clones all contain the D61N K64R mutation. DOM23h-262-10 (SEQ ID NO: 13) was isolated directly from the error prone library selection outputs, whilst DOM23h-437-9 (SEQ ID NO:), DOM23h-271-12 (SEQ ID NO:) and DOM23h-439-8 (SEQ ID NO:) were created by introducing the D61N K64R mutation by site-directed mutagenesis into DOM23h-437-6 (SEQ ID NO: 19), DOM23h-271-3 (SEQ ID NO: 14) and DOM23h-439-6 (SEQ ID NO: 22), respectively. DOM23h-437-9 (SEQ ID NO: 21) is the most potent of the four dAbs and as such was injected first, and then in combination with one of the other three dAbs. All dAbs were tested at 100 nM. No further RUs of dAb bound during the second injection, suggesting all four dAbs compete for the same antigen binding site, whereas the three lineages do not compete for the same antigen binding site if the D61N K64R double mutation is not present in the dAb nucleotide sequences. The data is summarised in FIGS. 9 and 10.

Summary of NR Mutation:

In summary, the addition of the D61N and K64R mutations to the DOM23h-271, DOM23h-437 and DOM23h-439 lineages improves the potency with which the dAbs neutralise hTGFβ-RII-mediated signalling, as measured in the A549 IL-11 release assay and the SBE-bla Hek293T cell sensor assay (Table 1). In addition, DOM23h-271-12 (SEQ ID NO: 16) which contains the D61N and K64R mutations, cross-reacts with mTGFβRII, since it displays the ability to neutralise mTGFβ-RII-mediated signalling in the MC3T3-E1 luciferase assay and RAW 264.7 phospho-Smad assay. DOM23h-437-9 (SEQ ID NO: 21) was able to inhibit mTGFβ-RII mediated signalling in the MC3T3-E1 luciferase assay, but not in the RAW 264.7 phospho-Smad assay. However, the presence of the D61N K64R mutation results in a decrease in thermal stability, as determined by DSC (Table 4). A reduction in expression level was also observed (Table 5).

Example 8

Mouse Model of Bleomycin-Induced Pulmonary Fibrosis

Bleomycin (BLM)-induced inflammation and fibrosis represent an experimental model for idiopathic pulmonary fibrosis. The method has been described before (Anon, et al., *Am J Respir. Crit. Care Med.* 2005 vol. 171, p 1279-1285. Piguet et al., *Int. J. Exp. Path.* 1997, vol. 78, p. 43-48. Gasse, et al., *J. Clin. Invest.*, (2007) vol 117, p 3786-3799).

BLM induces oxidative stress, DNA damage and apoptosis of alveolar macrophages and epithelial cells, leading to chemokine and proinflammatory cytokine secretion, inflammatory cell recruitment, remodelling and lung fibrosis.

Mice treated with bleomycin are dosed intra-nasally with dAbs binding TGFβ-RII and their effect on preventing pulmonary inflammation and fibrosis is determined.

While this disclosure has been particularly shown and described with references to embodiments thereof, it will be understood by those skilled in the art that various changes in form and details may be made therein without departing from the scope of the disclosure encompassed by the appended claims. All references identified herein are incorporated by reference as though fully set forth.

The material in the ASCII text file named "DB63509AmendNatlSeqList.txt[,]" created on Jan. 26, 2012 and having a size of 65,109 bytes is incorporated herein by reference in its entirety.

What is claimed is:

1. An isolated polypeptide comprising an amino acid sequence at least 90% identical to SEQ ID NO: 10, wherein the polypeptide binds TGFbetaRII with a Kd in the range of 10 pM to 50 nM.

2. The polypeptide of claim 1 comprising an amino acid sequence identical to SEQ ID NO: 10.

3. The polypeptide of claim 1 comprising at least one amino acid substitution selected from the group consisting of an asparagine at position 61 of the immunoglobulin single variable domain, an arginine at position 64 of the immunoglobulin single variable domain, a histidine at position 102 of the immunoglobulin single variable domain, an arginine at position 39 of the immunoglobulin single variable domain, an aspartic acid at position 53 of the immunoglobulin single variable domain, and a serine at position 103 of the immunoglobulin single variable domain.

4. The polypeptide of claim 1 that binds to human TGFbetaRII.

5. A fusion protein comprising the polypeptide of claim 1.

6. The polypeptide of claim 1 that neutralizes TGFbeta activity.

7. The polypeptide of claim 1 that inhibits binding of TGFbeta to TGFbetaRII.

8. A pharmaceutical composition comprising the polypeptide of claim 1.

9. A method of inhibiting TGFbetaRII signaling in an animal comprising the steps of:

a) providing an animal with a disease selected from the group consisting of tissue fibrosis, pulmonary fibrosis, idiopathic pulmonary fibrosis, liver fibrosis, liver cirrhosis, chronic hepatitis, rheumatoid arthritis, an ocular disorder, fibrosis of the skin, keloids, kidney fibrosis, nephritis, nephrosclerosis, a vascular condition and restenosis; and b) administering a pharmaceutically effective amount of the pharmaceutical composition of claim 8 to the animal.

10. The polypeptide of claim 1 wherein said polypeptide comprises a CDRL1 comprising SEQ ID NO: 82.

11. The polypeptide of claim 1 wherein said polypeptide comprises a CDRL2 comprising SEQ ID NO: 83.

12. The polypeptide of claim 1 wherein said polypeptide comprises a CDRL1 comprising SEQ ID NO: 82 and a CDRL2 comprising SEQ ID NO: 83.

13. An isolated nucleic acid encoding a polypeptide comprising an amino acid sequence at least 90% identical to SEQ ID NO: 10, wherein the polypeptide binds TGFbetaRI I with a Kd in the range of 10 pM to 50 nM.

14. A vector comprising the nucleic acid of claim 13.

15. A host cell comprising the nucleic acid of claim 13.

16. A method of producing an isolated polypeptide comprising the steps of:

a) providing the host cell of claim 15;
b) maintaining the host cell under conditions suitable for expression of the encoded polypeptide; and
c) isolating the encoded polypeptide;

whereby an isolated polypeptide is produced.

* * * * *

SEQUENCE LISTING

```
<160> NUMBER OF SEQ ID NOS: 130

<210> SEQ ID NO 1
<211> LENGTH: 116
<212> TYPE: PRT
<213> ORGANISM: Artificial Sequence
<220> FEATURE:
<223> OTHER INFORMATION: DOM23h-33 Amino acid sequence produced using
      molecular biology techniques.

<400> SEQUENCE: 1

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gln Tyr
            20                  25                  30

Arg Met Trp Trp Val Arg Gln Ala Pro Gly Lys Gly Leu Glu Trp Val
        35                  40                  45
```

```
Ser Ala Ile Ala Pro Ser Gly Asp Asn Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys His Arg Thr Ser Phe Asp Tyr Trp Gly Gln Gly Thr Leu Val
            100                 105                 110

Thr Val Ser Ser
        115

<210> SEQ ID NO 2
<211> LENGTH: 116
<212> TYPE: PRT
<213> ORGANISM: Artificial Sequence
<220> FEATURE:
<223> OTHER INFORMATION: DOM23h-251 Amino acid sequence produced using
      molecular biology techniques.

<400> SEQUENCE: 2

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Asp Tyr
             20                  25                  30

Asp Met Trp Trp Val Arg Gln Ala Pro Gly Lys Gly Leu Glu Trp Val
         35                  40                  45

Ser Lys Ile Thr Gln Lys Gly Asp Phe Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ala Thr His Phe Asp Tyr Trp Gly Gln Gly Thr Leu Val
            100                 105                 110

Thr Val Ser Ser
        115

<210> SEQ ID NO 3
<211> LENGTH: 124
<212> TYPE: PRT
<213> ORGANISM: Artificial Sequence
<220> FEATURE:
<223> OTHER INFORMATION: DOM23h-262 Amino acid sequence produced using
      molecular biology techniques.

<400> SEQUENCE: 3

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Phe Asn Tyr
             20                  25                  30

Glu Met Ala Trp Ala Arg Gln Ala Pro Gly Lys Gly Leu Glu Trp Val
         35                  40                  45

Ser Leu Ile Ser Ala Glu Gly Thr Arg Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

```
Ala Lys Arg Arg Asp Ala Ser Met Gly His Thr Thr Arg Phe Asp
            100                 105                 110

Tyr Trp Gly Gln Gly Thr Leu Val Thr Val Ser Ser
        115                 120

<210> SEQ ID NO 4
<211> LENGTH: 124
<212> TYPE: PRT
<213> ORGANISM: Artificial Sequence
<220> FEATURE:
<223> OTHER INFORMATION: DOM23h-271 Amino acid sequence produced using
      molecular biology techniques.

<400> SEQUENCE: 4

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Glu Tyr
            20                  25                  30

Arg Met Trp Trp Val Arg Gln Ala Pro Gly Lys Gly Leu Glu Trp Val
        35                  40                  45

Ser Ser Ile Glu Pro Ile Gly Asn Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ile Pro Gly His Lys Trp Thr Ala Asn Ser Arg Phe Asp
            100                 105                 110

Tyr Trp Gly Gln Gly Thr Leu Val Thr Val Ser Ser
        115                 120

<210> SEQ ID NO 5
<211> LENGTH: 121
<212> TYPE: PRT
<213> ORGANISM: Artificial Sequence
<220> FEATURE:
<223> OTHER INFORMATION: DOM23h-348 Amino acid sequence produced using
      molecular biology techniques.

<400> SEQUENCE: 5

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Asp Met Ala Trp Ala Arg Gln Ala Pro Gly Lys Gly Leu Glu Trp Val
        35                  40                  45

Ser Arg Ile Ser His Ser Gly Tyr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ser Trp Asp Gly Val His Ala Gln Phe Asp Tyr Trp Gly
            100                 105                 110

Gln Gly Thr Leu Val Thr Val Ser Ser
        115                 120

<210> SEQ ID NO 6
<211> LENGTH: 116
```

<212> TYPE: PRT
<213> ORGANISM: Artificial Sequence
<220> FEATURE:
<223> OTHER INFORMATION: DOM23h-435 Amino acid sequence produced using molecular biology techniques.

<400> SEQUENCE: 6

Glu Val Gln Leu Leu Glu Ser Gly Gly Gly Leu Val Gln Pro Gly Gly
1               5                   10                  15

Ser Leu Arg Leu Thr Cys Ala Ala Ser Gly Phe Thr Phe Thr Asp Asp
            20                  25                  30

Arg Met Trp Trp Val Arg Gln Ala Pro Gly Lys Gly Leu Glu Trp Val
        35                  40                  45

Ser Ala Ile Asp Pro Gln Gly Gln His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Asn Ser Ser Phe Asp Tyr Trp Gly Gln Gly Thr Leu Val
            100                 105                 110

Thr Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: DOM23h-436 Amino acid sequence produced using molecular biology techniques.

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Lys Met Gly Trp Val Arg Gln Ala Pro Gly Lys Gly Leu Glu Trp Val
        35                  40                  45

Ser Ser Ile Trp Pro Asn Gly Gly Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp His Met Gly Phe Asp Tyr Trp Gly Gln Gly Thr Leu Val
            100                 105                 110

Thr Val Ser Ser
        115

<210> SEQ ID NO 8
<211> LENGTH: 116
<212> TYPE: PRT
<213> ORGANISM: Artificial Sequence
<220> FEATURE:
<223> OTHER INFORMATION: DOM23h-437 Amino acid sequence produced using molecular biology techniques.

<400> SEQUENCE: 8

Glu Val Gln Leu Leu Glu Ser Gly Gly Gly Leu Val Gln Pro Gly Gly

```
                 1               5                  10                 15
Ser Leu Arg Leu Ser Cys Ala Ala Ser Gly Phe Thr Phe Ser Asp Tyr
                20                  25                 30

Arg Met Trp Trp Val Arg Gln Ala Pro Gly Lys Gly Leu Glu Trp Val
        35                  40                 45

Ser Ala Ile Asp Ser Gln Gly His Thr Thr Tyr Tyr Ala Asp Ser Val
        50                  55                 60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                 95

Ala Lys Tyr Gly Gly Tyr Phe Asp Tyr Trp Gly Gln Gly Thr Leu Val
            100                 105                110

Thr Val Ser Ser
        115
```

<210> SEQ ID NO 9
<211> LENGTH: 119
<212> TYPE: PRT
<213> ORGANISM: Artificial Sequence
<220> FEATURE:
<223> OTHER INFORMATION: DOM23h-438 Amino acid sequence produced using
      molecular biology techniques.

<400> SEQUENCE: 9

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Gln Gly
            20                  25                  30

Asp Met Trp Trp Val Arg Gln Ala Pro Gly Lys Gly Leu Glu Trp Val
        35                  40                  45

Ser Arg Ile Gly Met Asp Gly Asp Lys Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Ser Ser Thr Ser Pro Phe Asp Tyr Trp Gly Gln Gly
            100                 105                 110

Thr Leu Val Thr Val Ser Ser
        115
```

<210> SEQ ID NO 10
<211> LENGTH: 122
<212> TYPE: PRT
<213> ORGANISM: Artificial Sequence
<220> FEATURE:
<223> OTHER INFORMATION: DOM23h-439 Amino acid sequence produced using
      molecular biology techniques.

<400> SEQUENCE: 10

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Thr Glu
            20                  25                  30

Gln Met Trp Trp Val Arg Gln Ala Pro Gly Lys Gly Leu Glu Trp Val
        35                  40                  45

Ser Arg Ile Asp Ser Pro Gly Gly Arg Thr Tyr Tyr Ala Asp Ser Val
```

```
                50              55              60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Lys Arg His Ala Ala Gly Val Ser Gly Thr Tyr Phe Asp Tyr Trp
                100                 105                 110

Gly Gln Gly Thr Leu Val Thr Val Ser Ser
                115                 120

<210> SEQ ID NO 11
<211> LENGTH: 116
<212> TYPE: PRT
<213> ORGANISM: Artificial Sequence
<220> FEATURE:
<223> OTHER INFORMATION: DOM23h-440 Amino acid sequence produced using
      molecular biology techniques.

<400> SEQUENCE: 11

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Asp
                 20                  25                  30

Arg Met Trp Trp Val Arg Gln Ala Pro Gly Lys Gly Leu Glu Trp Val
             35                  40                  45

Ser Ala Ile Asp Pro Gln Gly Gln His Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Lys Glu Leu Leu Ser Phe Asp Tyr Trp Gly Gln Gly Thr Leu Val
                100                 105                 110

Thr Val Ser Ser
            115

<210> SEQ ID NO 12
<211> LENGTH: 124
<212> TYPE: PRT
<213> ORGANISM: Artificial Sequence
<220> FEATURE:
<223> OTHER INFORMATION: DOM23h-262-6 Amino acid sequence produced using
      molecular biology techniques.

<400> SEQUENCE: 12

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Phe Asn Tyr
                 20                  25                  30

Glu Met Ala Trp Ala Arg Gln Ala Pro Gly Lys Gly Leu Glu Trp Val
             35                  40                  45

Ser Leu Ile Ser Ala Glu Gly Thr Arg Thr Tyr Tyr Ala Asn Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Lys Arg Arg Asp Ala Ser Met Gly His Thr Thr Arg Arg Phe Asp
```

-continued

```
                    100                 105                 110

His Trp Gly Gln Gly Thr Leu Val Thr Val Ser Ser
        115                 120

<210> SEQ ID NO 13
<211> LENGTH: 124
<212> TYPE: PRT
<213> ORGANISM: Artificial Sequence
<220> FEATURE:
<223> OTHER INFORMATION: DOM23h-262-10 Amino acid sequence produced
      using molecular biology techniques.

<400> SEQUENCE: 13

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Phe Asn Tyr
            20                  25                  30

Glu Met Ala Trp Ala Arg Arg Ala Pro Gly Lys Gly Leu Glu Trp Val
        35                  40                  45

Ser Leu Ile Ser Ala Asp Gly Thr Arg Thr Tyr Tyr Ala Asn Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Arg Asp Ala Ser Met Gly His Thr Thr Arg Arg Phe Asp
            100                 105                 110

Tyr Ser Gly Gln Gly Thr Leu Val Thr Val Ser Ser
        115                 120

<210> SEQ ID NO 14
<211> LENGTH: 124
<212> TYPE: PRT
<213> ORGANISM: Artificial Sequence
<220> FEATURE:
<223> OTHER INFORMATION: DOM23h-271-3 Amino acid sequence produced using
      molecular biology techniques.

<400> SEQUENCE: 14

Glu Val Gln Leu Leu Glu Ser Gly Gly Gly Leu Val Gln Pro Gly Gly
 1               5                  10                  15

Ser Leu Arg Leu Ser Cys Thr Ala Ser Gly Phe Thr Phe Thr Glu Tyr
            20                  25                  30

Arg Met Trp Trp Val Arg Gln Ala Pro Gly Lys Gly Leu Glu Trp Val
        35                  40                  45

Ser Leu Ile Glu Pro Ile Gly Asn Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ile Pro Gly His Met Trp Thr Ala Asn Pro Arg Ser Asp
            100                 105                 110

Tyr Trp Gly Gln Gly Thr Gln Val Thr Val Ser Ser
        115                 120

<210> SEQ ID NO 15
<211> LENGTH: 124
<212> TYPE: PRT
```

<213> ORGANISM: Artificial Sequence
<220> FEATURE:
<223> OTHER INFORMATION: DOM23h-271-7 Amino acid sequence produced using molecular biology techniques.

<400> SEQUENCE: 15

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly Asn Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ile Pro Gly Arg Lys Trp Thr Ala Asn Ser Arg Phe Asp
            100                 105                 110

Tyr Trp Gly Gln Gly Thr Leu Val Thr Val Ser Ser
        115                 120
```

<210> SEQ ID NO 16
<211> LENGTH: 124
<212> TYPE: PRT
<213> ORGANISM: Artificial Sequence
<220> FEATURE:
<223> OTHER INFORMATION: DOM23h-271-12 Amino acid sequence produced using molecular biology techniques.

<400> SEQUENCE: 16

```
Glu Val Gln Leu Leu Glu Ser Gly Gly Gly Leu Val Gln Pro Gly Gly
 1               5                  10                  15

Ser Leu Arg Leu Ser Cys Thr Ala Ser Gly Phe Thr Phe Thr Glu Tyr
            20                  25                  30

Arg Met Trp Trp Val Arg Gln Ala Pro Gly Lys Gly Leu Glu Trp Val
        35                  40                  45

Ser Leu Ile Glu Pro Ile Gly Asn Arg Thr Tyr Tyr Ala Asn Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ile Pro Gly His Met Trp Thr Ala Asn Pro Arg Ser Asp
            100                 105                 110

Tyr Trp Gly Gln Gly Thr Gln Val Thr Val Ser Ser
        115                 120
```

<210> SEQ ID NO 17
<211> LENGTH: 124
<212> TYPE: PRT
<213> ORGANISM: Artificial Sequence
<220> FEATURE:
<223> OTHER INFORMATION: DOM23h-271-13 Amino acid sequence produced using molecular biology techniques.

<400> SEQUENCE: 17

```
Glu Val Gln Leu Leu Glu Ser Gly Gly Gly Leu Val Gln Pro Gly Gly
 1               5                  10                  15
```

```
Ser Leu Arg Leu Ser Cys Ala Ala Ser Gly Phe Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly Asn Arg Thr Tyr Tyr Ala Asn Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ile Pro Gly Arg Lys Trp Thr Ala Asn Ser Arg Phe Asp
            100                 105                 110

Tyr Trp Gly Gln Gly Thr Leu Val Thr Val Ser Ser
        115                 120

<210> SEQ ID NO 18
<211> LENGTH: 116
<212> TYPE: PRT
<213> ORGANISM: Artificial Sequence
<220> FEATURE:
<223> OTHER INFORMATION: DOM23h-437-4 Amino acid sequence produced using
      molecular biology techniques.

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Arg Met Trp Trp Val Arg Gln Ala Pro Gly Lys Gly Leu Glu Trp Val
        35                  40                  45

Ser Ala Ile Asp Ser Gln Gly His Thr Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Gly Gly Tyr Phe Asp Tyr Trp Gly Gln Gly Thr Leu Val
            100                 105                 110

Thr Val Ser Ser
        115

<210> SEQ ID NO 19
<211> LENGTH: 116
<212> TYPE: PRT
<213> ORGANISM: Artificial Sequence
<220> FEATURE:
<223> OTHER INFORMATION: DOM23h-437-6 Amino acid sequence produced using
      molecular biology techniques.

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Thr Ser Gly Phe Thr Phe Ser Asp Tyr
            20                  25                  30

Arg Met Trp Trp Val Arg Gln Ala Pro Gly Lys Gly Leu Glu Trp Val
        35                  40                  45

Ser Ala Ile Asp Ser Gln Gly His Thr Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Gly Gly Tyr Phe Asp Tyr Trp Gly Gln Gly Thr Leu Val
            100                 105                 110

Thr Val Ser Ser
        115

<210> SEQ ID NO 20
<211> LENGTH: 116
<212> TYPE: PRT
<213> ORGANISM: Artificial Sequence
<220> FEATURE:
<223> OTHER INFORMATION: DOM23h-437-8 Amino acid sequence produced using
      molecular biology techniques.

<400> SEQUENCE: 20

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Ile Ser Asp Tyr
            20                  25                  30

Arg Met Trp Trp Val Arg Gln Ala Pro Gly Lys Gly Leu Glu Trp Val
        35                  40                  45

Ser Ala Ile Asp Ser Gln Gly His Thr Thr Tyr Tyr Ala Asn Ser Val
    50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Gly Gly Tyr Phe Asp Tyr Trp Gly Gln Gly Thr Leu Val
            100                 105                 110

Thr Val Ser Ser
        115

<210> SEQ ID NO 21
<211> LENGTH: 116
<212> TYPE: PRT
<213> ORGANISM: Artificial Sequence
<220> FEATURE:
<223> OTHER INFORMATION: DOM23h-437-9 Amino acid sequence produced using
      molecular biology techniques.

<400> SEQUENCE: 21

Glu Val Gln Leu Leu Glu Ser Gly Gly Gly Leu Val Gln Pro Gly Gly
 1               5                   10                  15

Ser Leu Arg Leu Ser Cys Ala Thr Ser Gly Phe Thr Phe Ser Asp Tyr
            20                  25                  30

Arg Met Trp Trp Val Arg Gln Ala Pro Gly Lys Gly Leu Glu Trp Val
        35                  40                  45

Ser Ala Ile Asp Ser Gln Gly His Thr Thr Tyr Tyr Ala Asn Ser Val
    50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Gly Gly Tyr Phe Asp Tyr Trp Gly Gln Gly Thr Leu Val
            100                 105                 110
```

```
Thr Val Ser Ser
        115

<210> SEQ ID NO 22
<211> LENGTH: 122
<212> TYPE: PRT
<213> ORGANISM: Artificial Sequence
<220> FEATURE:
<223> OTHER INFORMATION: DOM23h-439-6 Amino acid sequence produced using
      molecular biology techniques.

<400> SEQUENCE: 22

Glu Val Gln Leu Leu Glu Ser Gly Gly Gly Leu Val Arg Pro Gly Gly
 1               5                  10                  15

Ser Leu Arg Leu Ser Cys Ala Ala Ser Gly Phe Thr Phe Gly Thr Glu
            20                  25                  30

Gln Met Trp Trp Val Arg Gln Ala Pro Gly Lys Gly Leu Glu Trp Val
        35                  40                  45

Ser Arg Ile Asp Ser Pro Gly Gly Arg Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg His Ala Ala Gly Val Ser Gly Thr Tyr Phe Asp Tyr Trp
            100                 105                 110

Gly Gln Gly Thr Leu Val Thr Val Ser Ser
        115                 120

<210> SEQ ID NO 23
<211> LENGTH: 122
<212> TYPE: PRT
<213> ORGANISM: Artificial Sequence
<220> FEATURE:
<223> OTHER INFORMATION: DOM23h-439-8 Amino acid sequence produced using
      molecular biology techniques.

<400> SEQUENCE: 23

Glu Val Gln Leu Leu Glu Ser Gly Gly Gly Leu Val Arg Pro Gly Gly
 1               5                  10                  15

Ser Leu Arg Leu Ser Cys Ala Ala Ser Gly Phe Thr Phe Gly Thr Glu
            20                  25                  30

Gln Met Trp Trp Val Arg Gln Ala Pro Gly Lys Gly Leu Glu Trp Val
        35                  40                  45

Ser Arg Ile Asp Ser Pro Gly Gly Arg Thr Tyr Tyr Ala Asn Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg His Ala Ala Gly Val Ser Gly Thr Tyr Phe Asp Tyr Trp
            100                 105                 110

Gly Gln Gly Thr Leu Val Thr Val Ser Ser
        115                 120

<210> SEQ ID NO 24
<211> LENGTH: 348
<212> TYPE: DNA
<213> ORGANISM: Artificial Sequence
```

```
<220> FEATURE:
<223> OTHER INFORMATION: DOM23h-33 Nucleic acid sequence produced using
      molecular biology techniques.

<400> SEQUENCE: 24
gaggtgcagc tgttggagtc tggggggaggc ttggtacagc ctgggggggtc cctgcgtctc      60 tcctgtgcag cctccggatt cacctttttcg cagtatcgga tgtggtgggt ccgccaggct     120
ccagggaagg gtctagagtg ggtctcagcg attgcgcctt ctggtgataa tacatactac     180
gcagactccg tgaagggccg gttcaccatc tcccgcgaca attccaagaa cacgctgtat     240
ctgcaaatga acagcctgcg tgccgaggac accgcggtat attactgtgc gaaacatcgg     300
acttcgtttg actactgggg tcagggaacc ctggtcaccg tctcgagc                  348

<210> SEQ ID NO 25
<211> LENGTH: 348
<212> TYPE: DNA
<213> ORGANISM: Artificial Sequence
<220> FEATURE:
<223> OTHER INFORMATION: DOM23h-251 Nucleic acid sequence produced using
      molecular biology techniques.

<400> SEQUENCE: 25
gaggtgcagc tgttggagtc tggggggaggc ttggtacagc ctgggggggtc cctgcgtctc      60 tcctgtgcag cctccggatt cacctttttcg gattatgata tgtggtgggt ccgccaggct     120
ccagggaagg gtctggagtg ggtctcaaag attacgcaga agggtgattt tacatactac     180
gcagactccg tgaagggccg gttcaccatc tcccgcgaca attccaagaa cacgctgtat     240
ctgcaaatga acagcctgcg tgccgaggac accgcggtat attactgtgc gaaagatgct     300
actcattttg actactgggg tcagggaacc ctggtcaccg tctcgagc                  348

<210> SEQ ID NO 26
<211> LENGTH: 372
<212> TYPE: DNA
<213> ORGANISM: Artificial Sequence
<220> FEATURE:
<223> OTHER INFORMATION: DOM23h-262 Nucleic acid sequence produced using
      molecular biology techniques.

<400> SEQUENCE: 26
gaggtgcagc tgttggagtc tggggggaggc ttggtacagc ctgggggggtc cctgcgtctc      60 tcctgtgcag cctccggatt cacctttttttt aattatgaga tggcgtgggc ccgccaggct     120
ccagggaagg gtctagagtg ggtctcattg attagtgctg agggtacgag gacatactac     180
gcagactccg tgaagggccg gttcaccatc tcccgcgaca attccaagaa cacgctgtat     240
ctgcaaatga acagcctgcg tgccgaggac accgcggtat attactgtgc aaaacggcgg     300
gatgctagta tgggtcatac tactcggcgg tttgactact ggggtcaggg aaccctggtc     360
accgtctcga gc                                                         372

<210> SEQ ID NO 27
<211> LENGTH: 373
<212> TYPE: DNA
<213> ORGANISM: Artificial Sequence
<220> FEATURE:
<223> OTHER INFORMATION: DOM23h-271 Nucleic acid sequence produced using
      molecular biology techniques.

<400> SEQUENCE: 27
gaggtgcagc tgttggagtc tggggggaggc ttggtacagc ctgggggggtc cctgcgtctc      60
```

```
tcctgtgcag cctccggatt cacctttacg gagtatagga tgtggtgggt ccgccaggct    120
ccagggaagg gtctagagtg ggtctcatcg attgagccga ttggtaatcg tacatactac    180
gcagactccg tgaagggccg gttcaccatc tcccgcgaca attccaagaa cacgctgtat    240
ctgcaaatga acagcctgcg tgccgaggat accgcggtat attactgtgc gaaacagatt    300
ccggggcata agtggactgc taattcgcgg tttgactact ggggtcaggg aaccctggtc    360
accgtctcga gcg                                                       373

<210> SEQ ID NO 28
<211> LENGTH: 363
<212> TYPE: DNA
<213> ORGANISM: Artificial Sequence
<220> FEATURE:
<223> OTHER INFORMATION: DOM23h-348 Nucleic acid sequence produced using
      molecular biology techniques.

<400> SEQUENCE: 28
gaggtgcagc tgttggagtc tggggggggc ttggtacagc ctgggggggtc cctgcgtctc    60 tcctgtgcag cctccggatt cacctttagt gattatgata tggcgtgggc ccgccaggct    120
ccagggaagg gtctagagtg ggtctcacgt atttctcata gtggttattc tacatactac    180
gcagactccg tgaagggccg gttcaccatc tcccgcgaca attccaagaa cacgctgtat    240
ctgcaaatga acagcctgcg tgccgaggac accgcggtat attactgtgc gaaacgttcg    300
tgggatgggg ttcatgcgca gtttgactac tggggtcagg gaaccctggt caccgtctcg    360
agc                                                                  363

<210> SEQ ID NO 29
<211> LENGTH: 349
<212> TYPE: DNA
<213> ORGANISM: Artificial Sequence
<220> FEATURE:
<223> OTHER INFORMATION: DOM23h-435 Nucleic acid sequence produced using
      molecular biology techniques.

<400> SEQUENCE: 29
gaggtgcagc tgttggagtc tggggggaggc ttggtacagc ctgggggggtc cctgcgtctc    60 acctgtgcag cctccggatt cacctttacg gatgatagga tgtggtgggt ccgccaggct    120
ccagggaagg gtctagagtg ggtctcagct attgatcctc agggtcagca tacatactac    180
gcagactccg tgaagggccg gttcaccatc tcccgcgaca attccaagaa cacgctgtat    240
ctgcaaatga acagcctgcg tgccgaggat accgcggtat attactgtgc gaaacataat    300
tcgagttttg actactgggg tcagggaacc ctggtcaccg tctcgagcg                349

<210> SEQ ID NO 30
<211> LENGTH: 349
<212> TYPE: DNA
<213> ORGANISM: Artificial Sequence
<220> FEATURE:
<223> OTHER INFORMATION: DOM23h-436 Nucleic acid sequence produced using
      molecular biology techniques.

<400> SEQUENCE: 30
gaggtgcagc tgttggagtc tggggggaggc ttggtacagc ctgggggggtc cctgcgtctc    60 tcctgtgcag cctccggatt cacctttagt gattataaga tgggttgggt ccgccaggct    120
ccagggaagg gtctagagtg ggtctcaagt atttggccta atggtggttt gacatactac    180
gcagactccg tgaagggccg gttcaccatc tcccgcgaca attccaagaa cacgctgtat    240
```

```
ctgcaaatga acagcctgcg tgccgaggat accgcggtat attactgtgc gaaagatcat    300
atgggttttg actactgggg tcagggaacc ctggtcaccg tctcgagcg               349
```

<210> SEQ ID NO 31
<211> LENGTH: 349
<212> TYPE: DNA
<213> ORGANISM: Artificial Sequence
<220> FEATURE:
<223> OTHER INFORMATION: DOM23h-437 Nucleic acid sequence produced using
      molecular biology techniques.

<400> SEQUENCE: 31

```
gaggtgcagc tgttggagtc tgggggaggc ttggtacagc ctgggggtc cctgcgtctc     60 tcctgtgcag cctccggatt caccttttct gattatcgta tgtggtgggt ccgccaggct    120
ccagggaagg gtctagagtg gtctcagcg attgattctc aggtcatac gacatactac     180 gcagactccg tgaagggccg gttcaccatc tcccgcgaca attccaagaa cacgctgtat    240
ctgcaaatga acagcctgcg tgccgaggat accgcggtat attactgtgc gaaatatggg    300
ggttattttg actactgggg tcagggaacc ctggtcaccg tctcgagcg               349
```

<210> SEQ ID NO 32
<211> LENGTH: 358
<212> TYPE: DNA
<213> ORGANISM: Artificial Sequence
<220> FEATURE:
<223> OTHER INFORMATION: DOM23h-438 Nucleic acid sequence produced using
      molecular biology techniques.

<400> SEQUENCE: 32

```
gaggtgcagc tgttggagtc tgggggaggc ttggtacagc ctgggggtc cctgcgtctc     60 tcctgtgcag cctccggatt cacctttgcg caggggata tgtggtgggt ccgccaggct    120
ccagggaagg gtctggagtg gtctcacgt attggtatgg atggtgataa gacatactac    180
gcagactccg tgaagggccg gttcaccatc tcccgcgaca attccaagaa cacgctgtat    240
ctgcaaatga acagcctgcg tgccgaggac accgcggtat attactgtgc gaaaggtcct    300
tcgagtacta gtccgtttga ctactggggt cagggaaccc tggtcaccgt ctcgagcg     358
```

<210> SEQ ID NO 33
<211> LENGTH: 367
<212> TYPE: DNA
<213> ORGANISM: Artificial Sequence
<220> FEATURE:
<223> OTHER INFORMATION: DOM23h-439 Nucleic acid sequence produced using
      molecular biology techniques.

<400> SEQUENCE: 33

```
gaggtgcagc tgttggagtc tgggggaggc ttggtacagc ctgggggtc cctgcgtctc     60 tcctgtgcag cctccggatt cacctttggg acggagcaga tgtggtgggt ccgccaggct    120
ccagggaagg gtctagagtg gtctcacgt attgattcgc ctggtgggag gacatactac    180
gcagactccg tgaagggccg gttcaccatc tcccgcgaca attccaagaa cacgctgtat    240
ctgcaaatga acagcctgcg tgccgaggac accgcggtat attactgtgc gaaacggcat    300
gcggctgggg tttcgggtac ttattttgac tactggggtc agggaaccct ggtcaccgtc    360
tcgagcg                                                              367
```

<210> SEQ ID NO 34
<211> LENGTH: 349
<212> TYPE: DNA

<213> ORGANISM: Artificial Sequence
<220> FEATURE:
<223> OTHER INFORMATION: DOM23h-440 Nucleic acid sequence produced using molecular biology techniques.

<400> SEQUENCE: 34

| | | | | | |
|---|---|---|---|---|---|
| gaggtgcagc | tgttggagtc | tgggggaggc | ttggtacagc | ctgggggtc | cctgcgtctc | 60 |
| tcctgtgcag | cctccggatt | cacctttacg | gatgatagga | tgtggtgggt | ccgccaggct | 120 |
| ccagggaagg | gtctagagtg | ggtctcagct | attgatcctc | agggtcagca | tacatactac | 180 |
| gcagactccg | tgaagggccg | gttcaccatc | tcccgcgaca | attccaagaa | cacgctgtat | 240 |
| ctgcaaatga | acagcctgcg | tgccgaggac | accgcggtat | attactgtgc | gaaagagctg | 300 |
| cttagttttg | actactgggg | tcagggaacc | ctggtcaccg | tctcgagcg | | 349 |

<210> SEQ ID NO 35
<211> LENGTH: 372
<212> TYPE: DNA
<213> ORGANISM: Artificial Sequence
<220> FEATURE:
<223> OTHER INFORMATION: DOM23h-262-6 Nucleic acid sequence produced using molecular biology techniques.

<400> SEQUENCE: 35

| | | | | | |
|---|---|---|---|---|---|
| gaggtgcagc | tgttggagtc | tgggggaggc | ttggtacagc | ctgggggtc | cctgcgtctc | 60 |
| tcctgtgcag | cctccggatt | caccttttttt | aattatgaga | tggcgtgggc | ccgccaggct | 120 |
| ccagggaagg | gcctagagtg | ggtctcattg | attagtgctg | agggtacgag | gacatactac | 180 |
| gcaaactccg | tgaagggccg | gttcaccatc | tcccgcgaca | attccaagaa | cacgctgtat | 240 |
| ctgcaaatga | acagcctgcg | tgccgaggac | accgcggtat | attactgtgc | aaaacggcgg | 300 |
| gatgctagta | tgggtcatac | tactcggcgg | tttgaccact | ggggtcaggg | aaccctggtc | 360 |
| accgtctcga | gc | | | | | 372 |

<210> SEQ ID NO 36
<211> LENGTH: 371
<212> TYPE: DNA
<213> ORGANISM: Artificial Sequence
<220> FEATURE:
<223> OTHER INFORMATION: DOM23h-262-10 Nucleic acid sequence produced using molecular biology techniques.

<400> SEQUENCE: 36

| | | | | | |
|---|---|---|---|---|---|
| gaggtgcagc | tgttggagtc | tgggggaggc | ttagtacagc | ccggggggtc | cctgcgtctc | 60 |
| tcctgtgcag | cctccggatt | caccttttttt | aattatgaga | tggcgtgggc | ccgccgggct | 120 |
| ccagggaagg | gtctagagtg | ggtctcattg | attagtgctg | atggtacgag | gacatactac | 180 |
| gcaaactccg | tgagggggccg | gttcaccatc | tcccgcgaca | attccaagaa | ccgctgtatc | 240 |
| tgcaaatgaa | cagcctgcgt | gccgaggaca | ccgcggtata | ttactgtgca | aaacggcggg | 300 |
| atgctagtat | gggtcatact | actcggcggt | ttgactactc | gggtcaggga | accctggtca | 360 |
| ccgtctcgag | c | | | | | 371 |

<210> SEQ ID NO 37
<211> LENGTH: 372
<212> TYPE: DNA
<213> ORGANISM: Artificial Sequence
<220> FEATURE:
<223> OTHER INFORMATION: DOM23h-271-3 Nucleic acid sequence produced using molecular biology techniques.

<400> SEQUENCE: 37

```
gaggtgcagc tgttggagtc tgggggaggc ttggtacagc ctgggggggtc cctgcgtctc      60 tcctgcacag cctccggatt caccttttacg gagtatagga tgtggtgggt ccgccaggct    120
ccagggaagg gtctagagtg ggtctcattg attgagccga ttggtaatcg tacatactac    180
gcagactccg tgaagggccg gttcaccatc tcccgcgaca attccaagaa cacgctgtat    240
ctgcaaatga acagcctgcg tgctgaggat accgcggtat attactgtgc gaaacagatt    300
ccggggcata tgtggactgc taatccgcgg tctgactact ggggtcaggg aacccaggtc    360
accgtctcga gc                                                         372
```

<210> SEQ ID NO 38
<211> LENGTH: 372
<212> TYPE: DNA
<213> ORGANISM: Artificial Sequence
<220> FEATURE:
<223> OTHER INFORMATION: DOM23h-271-7 Nucleic acid sequence produced
      using molecular biology techniques.

<400> SEQUENCE: 38

```
gaggtgcagc tgttggagtc tgggggaggc ttggtacagc ctgggggggtc cctgcgtctc      60 tcctgtgcag cctccggatt cacctttacg gagtatagga tgtggtgggt ccgccaggct    120
ccggggaagg gtctcgagtg ggtctcagcg attgagccga ttggtaatcg tacatactac    180
gcagactccg tgaagggccg gttcaccatc tcccgcgaca attccaagaa cacgctgtat    240
ctgcaaatga acagcctgcg tgccgaggat accgcggtat attactgtgc gaaacagatt    300
ccggggcgta agtggactgc taattcgcgg tttgactact ggggtcaggg aaccctggtc    360
accgtctcga gc                                                         372
```

<210> SEQ ID NO 39
<211> LENGTH: 372
<212> TYPE: DNA
<213> ORGANISM: Artificial Sequence
<220> FEATURE:
<223> OTHER INFORMATION: DOM23h-271-12 Nucleic acid sequence produced
      using molecular biology techniques.

<400> SEQUENCE: 39

```
gaggtgcagc tgttggagtc tgggggaggc ttggtacagc ctgggggggtc cctgcgtctc      60 tcctgcacag cctccggatt cacctttacg gagtatagga tgtggtgggt ccgccaggct    120
ccagggaagg gtctagagtg ggtctcattg attgagccga ttggtaatcg tacatactac    180
gcaaactccg tgaggggccg gttcaccatc tcccgcgaca attccaagaa cacgctgtat    240
ctgcaaatga acagcctgcg tgctgaggat accgcggtat attactgtgc gaaacagatt    300
ccggggcata tgtggactgc taatccgcgg tctgactact ggggtcaggg aacccaggtc    360
accgtctcga gc                                                         372
```

<210> SEQ ID NO 40
<211> LENGTH: 372
<212> TYPE: DNA
<213> ORGANISM: Artificial Sequence
<220> FEATURE:
<223> OTHER INFORMATION: DOM23h-271-13 Nucleic acid sequence produced
      using molecular biology techniques.

<400> SEQUENCE: 40

```
gaggtgcagc tgttggagtc tgggggaggc ttggtacagc ctgggggggtc cctgcgtctc      60 tcctgtgcag cctccggatt cacctttacg gagtatagga tgtggtgggt ccgccaggct    120
```

```
ccggggaagg gtctcgagtg ggtctcagcg attgagccga ttggtaatcg tacatactac    180
gcaaactccg tgagggaccg gttcaccatc tcccgcgaca attccaagaa cacgctgtat    240
ctgcaaatga acagcctgcg tgccgaggat accgcggtat attactgtgc gaaacagatt    300
ccggggcgta agtggactgc taattcgcgg tttgactact ggggtcaggg aaccctggtc    360
accgtctcga gc                                                        372
```

```
<210> SEQ ID NO 41
<211> LENGTH: 348
<212> TYPE: DNA
<213> ORGANISM: Artificial Sequence
<220> FEATURE:
<223> OTHER INFORMATION: DOM23h-437-4 Nucleic acid sequence produced
      using molecular biology techniques.

<400> SEQUENCE: 41
gaggtgcagc tgttggagtc tgggggaggc ttggtacagc ctggggggtc cctgcgtctc     60
tcctgtgcag cctccggatt caccatttct gattatcgta tgtggtgggt ccgccaggct    120
ccagggaagg gtctagagtg gtctcagcg attgattctc aggtcatac gacatactac     180 gcagactccg tgagggaccg gttcaccatc tcccgcgaca attccaagaa cacgctgtat    240
ctgcaaatga acagcctgcg tgccgaggat accgcggtat attactgtgc gaaatatggg    300
ggttattttg actactgggg tcagggaacc ctggtcaccg tctcgagc                 348
```

```
<210> SEQ ID NO 42
<211> LENGTH: 348
<212> TYPE: DNA
<213> ORGANISM: Artificial Sequence
<220> FEATURE:
<223> OTHER INFORMATION: DOM23h-437-6 Nucleic acid sequence produced
      using molecular biology techniques.

<400> SEQUENCE: 42
gaggtgcagc tgttggagtc tgggggaggc ttggtacagc ctggggggtc cctgcgtctc     60
tcctgtgcaa cctccggatt caccttttct gattatcgta tgtggtgggt ccgccaggct    120
ccagggaagg gtctagagtg gtctcagcg attgattctc aggtcatac gacatactac     180 gcagactccg tgaagggccg gttcaccatc tcccgcgaca attccaagaa cacgctgtat    240
ctgcaaatga acagcctgcg cgccgaggat accgcggtat attactgtgc gaaatatggg    300
ggttattttg actactgggg tcagggaacc ctggtcaccg tctcgagc                 348
```

```
<210> SEQ ID NO 43
<211> LENGTH: 348
<212> TYPE: DNA
<213> ORGANISM: Artificial Sequence
<220> FEATURE:
<223> OTHER INFORMATION: DOM23h-437-8 Nucleic acid sequence produced
      using molecular biology techniques.

<400> SEQUENCE: 43
gaggtgcagc tgttggagtc tgggggaggc ttggtacagc ctggggggtc cctgcgtctc     60
tcctgtgcag cctccggatt caccatttct gattatcgta tgtggtgggt ccgccaggct    120
ccagggaagg gtctagagtg gtctcagcg attgattctc aggtcatac gacatactac     180 gcaaactccg tgagggaccg gttcaccatc tcccgcgaca attccaagaa cacgctgtat    240
ctgcaaatga acagcctgcg tgccgaggat accgcggtat attactgtgc gaaatatggg    300
ggttattttg actactgggg tcagggaacc ctggtcaccg tctcgagc                 348
```

<210> SEQ ID NO 44
<211> LENGTH: 348
<212> TYPE: DNA
<213> ORGANISM: Artificial Sequence
<220> FEATURE:
<223> OTHER INFORMATION: DOM23h-437-9 Nucleic acid sequence produced using molecular biology techniques.

<400> SEQUENCE: 44

```
gaggtgcagc tgttggagtc tgggggaggc ttggtacagc ctggggggtc cctgcgtctc      60
tcctgtgcaa cctccggatt caccttttct gattatcgta tgtggtgggt ccgccaggct     120
ccagggaagg gtctagagtg ggtctcagcg attgattctc aggtcatac gacatactac     180 gcaaactccg tgaggggccg gttcaccatc tcccgcgaca attccaagaa cacgctgtat     240
ctgcaaatga acagcctgcg cgccgaggat accgcggtat attactgtgc gaaatatggg    300
ggttattttg actactgggg tcagggaacc ctggtcaccg tctcgagc                  348
```

<210> SEQ ID NO 45
<211> LENGTH: 366
<212> TYPE: DNA
<213> ORGANISM: Artificial Sequence
<220> FEATURE:
<223> OTHER INFORMATION: DOM23h-439-6 Nucleic acid sequence produced using molecular biology techniques.

<400> SEQUENCE: 45

```
gaggtgcagc tgttggagtc tgggggaggc ttggtacggc ctggggggtc cctgcgtctc      60
tcctgtgcag cctccggatt cacctttggg acggagcaga tgtggtgggt ccgccaggct     120
ccagggaagg gtctagagtg ggtctcacga attgattcac ctggtgggag gacatactac    180
gcagactccg tgaggggccg gttcaccatc tcccgcgaca attccaagaa cacgctgtat     240
ctgcaaatga acagcctgcg tgccgaggac accgcggtat attactgtgc gaaacggcat    300
gcggctgggg tttcgggtac ttattttgac tactggggtc agggaaccct ggtcaccgtc    360
tcgagc                                                               366
```

<210> SEQ ID NO 46
<211> LENGTH: 366
<212> TYPE: DNA
<213> ORGANISM: Artificial Sequence
<220> FEATURE:
<223> OTHER INFORMATION: DOM23h-439-8 Nucleic acid sequence produced using molecular biology techniques.

<400> SEQUENCE: 46

```
gaggtgcagc tgttggagtc tgggggaggc ttggtacggc ctggggggtc cctgcgtctc      60
tcctgtgcag cctccggatt cacctttggg acggagcaga tgtggtgggt ccgccaggct     120
ccagggaagg gtctagagtg ggtctcacga attgattcac ctggtgggag gacatactac    180
gcaaactccg tgaggggccg gttcaccatc tcccgcgaca attccaagaa cacgctgtat     240
ctgcaaatga acagcctgcg tgccgaggac accgcggtat attactgtgc gaaacggcat    300
gcggctgggg tttcgggtac ttattttgac tactggggtc agggaaccct ggtcaccgtc    360
tcgagc                                                               366
```

<210> SEQ ID NO 47
<211> LENGTH: 20
<212> TYPE: PRT
<213> ORGANISM: Artificial Sequence

```
<220> FEATURE:
<223> OTHER INFORMATION: Amino acid sequence produced using molecular
      biology techniques.

<400> SEQUENCE: 47

Thr Thr Gly Cys Ala Gly Gly Cys Gly Thr Gly Gly Cys Ala Ala Cys
1               5                   10                  15

Ala Gly Cys Gly
            20

<210> SEQ ID NO 48
<211> LENGTH: 23
<212> TYPE: PRT
<213> ORGANISM: Artificial Sequence
<220> FEATURE:
<223> OTHER INFORMATION: Amino acid sequence produced using molecular
      biology techniques.

<400> SEQUENCE: 48

Cys Ala Cys Gly Ala Cys Gly Thr Thr Gly Thr Ala Ala Ala Ala Cys
1               5                   10                  15

Gly Ala Cys Gly Gly Cys Cys
            20

<210> SEQ ID NO 49
<211> LENGTH: 24
<212> TYPE: PRT
<213> ORGANISM: Artificial Sequence
<220> FEATURE:
<223> OTHER INFORMATION: Amino acid sequence produced using molecular
      biology techniques.

<400> SEQUENCE: 49

Ala Gly Cys Gly Gly Ala Thr Ala Ala Cys Ala Ala Thr Thr Thr Cys
1               5                   10                  15

Ala Cys Ala Cys Ala Gly Gly Ala
            20

<210> SEQ ID NO 50
<211> LENGTH: 24
<212> TYPE: PRT
<213> ORGANISM: Artificial Sequence
<220> FEATURE:
<223> OTHER INFORMATION: Amino acid sequence produced using molecular
      biology techniques.

<400> SEQUENCE: 50

Cys Gly Cys Cys Ala Gly Gly Gly Thr Thr Thr Thr Cys Cys Cys Ala
1               5                   10                  15

Gly Thr Cys Ala Cys Gly Ala Cys
            20

<210> SEQ ID NO 51
<211> LENGTH: 20
<212> TYPE: PRT
<213> ORGANISM: Artificial Sequence
<220> FEATURE:
<223> OTHER INFORMATION: Amino acid sequence produced biology
      techniques.

<400> SEQUENCE: 51

Thr Thr Gly Cys Ala Gly Gly Cys Gly Thr Gly Gly Cys Ala Ala Cys
1               5                   10                  15

Ala Gly Cys Gly
            20
```

<210> SEQ ID NO 52
<211> LENGTH: 23
<212> TYPE: PRT
<213> ORGANISM: Artificial Sequence
<220> FEATURE:
<223> OTHER INFORMATION: Amino acid sequence produced using molecular
      biology techniques.

<400> SEQUENCE: 52

Cys Ala Cys Gly Ala Cys Gly Thr Thr Gly Thr Ala Ala Ala Ala Cys
1               5                   10                  15

Gly Ala Cys Gly Gly Cys Cys
            20

<210> SEQ ID NO 53
<211> LENGTH: 30
<212> TYPE: PRT
<213> ORGANISM: Artificial Sequence
<220> FEATURE:
<223> OTHER INFORMATION: Amino acid sequence produced using molecular
      biology techniques.

<400> SEQUENCE: 53

Gly Ala Ala Cys Cys Gly Gly Cys Cys Cys Cys Thr Cys Ala Cys Gly
1               5                   10                  15

Gly Ala Gly Thr Thr Thr Gly Cys Gly Thr Ala Gly Thr Ala
            20                  25                  30

<210> SEQ ID NO 54
<211> LENGTH: 30
<212> TYPE: PRT
<213> ORGANISM: Artificial Sequence
<220> FEATURE:
<223> OTHER INFORMATION: Amino acid sequence produced using molecular
      biology techniques.

<400> SEQUENCE: 54

Thr Ala Cys Thr Ala Cys Gly Cys Ala Ala Ala Cys Thr Cys Cys Gly
1               5                   10                  15

Thr Gly Ala Gly Gly Gly Gly Cys Cys Gly Gly Thr Thr Cys
            20                  25                  30

<210> SEQ ID NO 55
<211> LENGTH: 5
<212> TYPE: PRT
<213> ORGANISM: Artificial Sequence
<220> FEATURE:
<223> OTHER INFORMATION: DOM23h-33 CDR1 Amino acid sequence produced
      using molecular biology techniques.

<400> SEQUENCE: 55

Gln Tyr Arg Met Trp
1               5

<210> SEQ ID NO 56
<211> LENGTH: 17
<212> TYPE: PRT
<213> ORGANISM: Artificial Sequence
<220> FEATURE:
<223> OTHER INFORMATION: DOM23h-33 CDR2 Amino acid sequence produced
      using molecular biology techniques.

<400> SEQUENCE: 56

Ala Ile Ala Pro Ser Gly Asp Asn Thr Tyr Tyr Ala Asp Ser Val Lys
1               5                   10                  15

Gly

<210> SEQ ID NO 57
<211> LENGTH: 7
<212> TYPE: PRT
<213> ORGANISM: Artificial Sequence
<220> FEATURE:
<223> OTHER INFORMATION: DOM23h-33 CDR3 Amino acid sequence produced
      using molecular biology techniques.

<400> SEQUENCE: 57

His Arg Thr Ser Phe Asp Tyr
 1               5

<210> SEQ ID NO 58
<211> LENGTH: 5
<212> TYPE: PRT
<213> ORGANISM: Artificial Sequence
<220> FEATURE:
<223> OTHER INFORMATION: DOM23h-251 CDR1 Amino acid sequence produced
      using molecular biology techniques.

<400> SEQUENCE: 58

Asp Tyr Asp Met Trp
 1               5

<210> SEQ ID NO 59
<211> LENGTH: 17
<212> TYPE: PRT
<213> ORGANISM: Artificial Sequence
<220> FEATURE:
<223> OTHER INFORMATION: DOM23h-251 CDR2 Amino acid sequence produced
      using molecular biology techniques.

<400> SEQUENCE: 59

Lys Ile Thr Gln Lys Gly Asp Phe Thr Tyr Tyr Ala Asp Ser Val Lys
 1               5                  10                  15
Gly

<210> SEQ ID NO 60
<211> LENGTH: 7
<212> TYPE: PRT
<213> ORGANISM: Artificial Sequence
<220> FEATURE:
<223> OTHER INFORMATION: DOM23h-251 CDR3 Amino acid sequence produced
      using molecular biology techniques.

<400> SEQUENCE: 60

Asp Ala Thr His Phe Asp Tyr
 1               5

<210> SEQ ID NO 61
<211> LENGTH: 5
<212> TYPE: PRT
<213> ORGANISM: Artificial Sequence
<220> FEATURE:
<223> OTHER INFORMATION: DOM23h-262 CDR1 Amino acid sequence produced
      using molecular biology techniques.

<400> SEQUENCE: 61

Asn Tyr Glu Met Ala
 1               5

<210> SEQ ID NO 62
<211> LENGTH: 17
<212> TYPE: PRT

<213> ORGANISM: Artificial Sequence
<220> FEATURE:
<223> OTHER INFORMATION: DOM23h-262 CDR2 Amino acid sequence produced using molecular biology techniques.

<400> SEQUENCE: 62

Leu Ile Ser Ala Glu Gly Thr Arg Thr Tyr Tyr Ala Asp Ser Val Lys
 1               5                  10                  15

Gly

<210> SEQ ID NO 63
<211> LENGTH: 15
<212> TYPE: PRT
<213> ORGANISM: Artificial Sequence
<220> FEATURE:
<223> OTHER INFORMATION: DOM23h-262 CDR3 Amino acid sequence produced using molecular biology techniques.

<400> SEQUENCE: 63

Arg Arg Asp Ala Ser Met Gly His Thr Thr Arg Arg Phe Asp Tyr
 1               5                  10                  15

<210> SEQ ID NO 64
<211> LENGTH: 5
<212> TYPE: PRT
<213> ORGANISM: Artificial Sequence
<220> FEATURE:
<223> OTHER INFORMATION: DOM23h-271 CDR1 Amino acid sequence produced using molecular biology techniques.

<400> SEQUENCE: 64

Glu Tyr Arg Met Trp
 1               5

<210> SEQ ID NO 65
<211> LENGTH: 17
<212> TYPE: PRT
<213> ORGANISM: Artificial Sequence
<220> FEATURE:
<223> OTHER INFORMATION: DOM23h-271 CDR2 Amino acid sequence produced using molecular biology techniques.

<400> SEQUENCE: 65

Ser Ile Glu Pro Ile Gly Asn Arg Thr Tyr Tyr Ala Asp Ser Val Lys
 1               5                  10                  15

Gly

<210> SEQ ID NO 66
<211> LENGTH: 15
<212> TYPE: PRT
<213> ORGANISM: Artificial Sequence
<220> FEATURE:
<223> OTHER INFORMATION: DOM23h-271 CDR3 Amino acid sequence produced using molecular biology techniques.

<400> SEQUENCE: 66

Gln Ile Pro Gly His Lys Trp Thr Ala Asn Ser Arg Phe Asp Tyr
 1               5                  10                  15

<210> SEQ ID NO 67
<211> LENGTH: 5
<212> TYPE: PRT
<213> ORGANISM: Artificial Sequence
<220> FEATURE:
<223> OTHER INFORMATION: DOM23h-348 CDR1 Amino acid sequence produced using molecular biology techniques.

```
<400> SEQUENCE: 67

Asp Tyr Asp Met Ala
1               5

<210> SEQ ID NO 68
<211> LENGTH: 17
<212> TYPE: PRT
<213> ORGANISM: Artificial Sequence
<220> FEATURE:
<223> OTHER INFORMATION: DOM23h-348 CDR2 Amino acid sequence produced
      using molecular biology techniques.

<400> SEQUENCE: 68

Arg Ile Ser His Ser Gly Tyr Ser Thr Tyr Tyr Ala Asp Ser Val Lys
1               5                   10                  15

Gly

<210> SEQ ID NO 69
<211> LENGTH: 13
<212> TYPE: PRT
<213> ORGANISM: Artificial Sequence
<220> FEATURE:
<223> OTHER INFORMATION: DOM23h-348 CDR3 Amino acid sequence produced
      using molecular biology techniques.

<400> SEQUENCE: 69

Arg Ser Trp Asp Gly Val His Ala Gln Phe Asp Tyr Trp
1               5                   10

<210> SEQ ID NO 70
<211> LENGTH: 5
<212> TYPE: PRT
<213> ORGANISM: Artificial Sequence
<220> FEATURE:
<223> OTHER INFORMATION: DOM23h-435 CDR1 Amino acid sequence produced
      using molecular biology techniques.

<400> SEQUENCE: 70

Asp Asp Arg Met Trp
1               5

<210> SEQ ID NO 71
<211> LENGTH: 17
<212> TYPE: PRT
<213> ORGANISM: Artificial Sequence
<220> FEATURE:
<223> OTHER INFORMATION: DOM23h-435 CDR2 Amino acid sequence produced
      using molecular biology techniques.

<400> SEQUENCE: 71

Ala Ile Asp Pro Gln Gly Gln His Thr Tyr Tyr Ala Asp Ser Val Lys
1               5                   10                  15

Gly

<210> SEQ ID NO 72
<211> LENGTH: 8
<212> TYPE: PRT
<213> ORGANISM: Artificial Sequence
<220> FEATURE:
<223> OTHER INFORMATION: DOM23h-435 CDR3 Amino acid sequence produced
      using molecular biology techniques.

<400> SEQUENCE: 72

His Asn Ser Ser Phe Asp Tyr Trp
1               5
```

<210> SEQ ID NO 73
<211> LENGTH: 5
<212> TYPE: PRT
<213> ORGANISM: Artificial Sequence
<220> FEATURE:
<223> OTHER INFORMATION: DOM23h-436 CDR1 Amino acid sequence produced using molecular biology techniques.

<400> SEQUENCE: 73

Asp Tyr Lys Met Gly
1               5

<210> SEQ ID NO 74
<211> LENGTH: 17
<212> TYPE: PRT
<213> ORGANISM: Artificial Sequence
<220> FEATURE:
<223> OTHER INFORMATION: DOM23h-436 CDR2 Amino acid sequence produced using molecular biology techniques.

<400> SEQUENCE: 74

Ser Ile Trp Pro Asn Gly Gly Leu Thr Tyr Tyr Ala Asp Ser Val Lys
1               5                   10                  15

Gly

<210> SEQ ID NO 75
<211> LENGTH: 8
<212> TYPE: PRT
<213> ORGANISM: Artificial Sequence
<220> FEATURE:
<223> OTHER INFORMATION: DOM23h-436 CDR3 Amino acid sequence produced using molecular biology techniques.

<400> SEQUENCE: 75

Asp His Met Gly Phe Asp Tyr Trp
1               5

<210> SEQ ID NO 76
<211> LENGTH: 5
<212> TYPE: PRT
<213> ORGANISM: Artificial Sequence
<220> FEATURE:
<223> OTHER INFORMATION: DOM23h-437 CDR1 Amino acid sequence produced using molecular biology techniques.

<400> SEQUENCE: 76

Asp Tyr Arg Met Trp
1               5

<210> SEQ ID NO 77
<211> LENGTH: 17
<212> TYPE: PRT
<213> ORGANISM: Artificial Sequence
<220> FEATURE:
<223> OTHER INFORMATION: DOM23h-437 CDR2 Amino acid sequence produced using molecular biology techniques.

<400> SEQUENCE: 77

Ala Ile Asp Ser Gln Gly His Thr Thr Tyr Tyr Ala Asp Ser Val Lys
1               5                   10                  15

Gly

<210> SEQ ID NO 78
<211> LENGTH: 8
<212> TYPE: PRT
<213> ORGANISM: Artificial Sequence

```
<220> FEATURE:
<223> OTHER INFORMATION: DOM23h-437 CDR3 Amino acid sequence produced
      using molecular biology techniques.

<400> SEQUENCE: 78

Tyr Gly Gly Tyr Phe Asp Tyr Trp
1               5

<210> SEQ ID NO 79
<211> LENGTH: 5
<212> TYPE: PRT
<213> ORGANISM: Artificial Sequence
<220> FEATURE:
<223> OTHER INFORMATION: DOM23h-438 CDR1 Amino acid sequence produced
      using molecular biology techniques.

<400> SEQUENCE: 79

Gln Gly Asp Met Trp
1               5

<210> SEQ ID NO 80
<211> LENGTH: 17
<212> TYPE: PRT
<213> ORGANISM: Artificial Sequence
<220> FEATURE:
<223> OTHER INFORMATION: DOM23h-438 CDR2 Amino acid sequence produced
      using molecular biology techniques.

<400> SEQUENCE: 80

Arg Ile Gly Met Asp Gly Asp Lys Thr Tyr Tyr Ala Asp Ser Val Lys
1               5                   10                  15

Gly

<210> SEQ ID NO 81
<211> LENGTH: 10
<212> TYPE: PRT
<213> ORGANISM: Artificial Sequence
<220> FEATURE:
<223> OTHER INFORMATION: DOM23h-438 CDR3 Amino acid sequence produced
      using molecular biology techniques.

<400> SEQUENCE: 81

Gly Pro Ser Ser Thr Ser Pro Phe Asp Tyr
1               5                   10

<210> SEQ ID NO 82
<211> LENGTH: 5
<212> TYPE: PRT
<213> ORGANISM: Artificial Sequence
<220> FEATURE:
<223> OTHER INFORMATION: DOM23h-439 CDR1 Amino acid sequence produced
      using molecular biology techniques.

<400> SEQUENCE: 82

Thr Glu Gln Met Trp
1               5

<210> SEQ ID NO 83
<211> LENGTH: 17
<212> TYPE: PRT
<213> ORGANISM: Artificial Sequence
<220> FEATURE:
<223> OTHER INFORMATION: DOM23h-439 CDR2 Amino acid sequence produced
      using molecular biology techniques.

<400> SEQUENCE: 83

Arg Ile Asp Ser Pro Gly Gly Arg Thr Tyr Tyr Ala Asp Ser Val Lys
```

```
                1               5                  10                  15

Gly

<210> SEQ ID NO 84
<211> LENGTH: 13
<212> TYPE: PRT
<213> ORGANISM: Artificial Sequence
<220> FEATURE:
<223> OTHER INFORMATION: DOM23h-439 CDR3 Amino acid sequence produced
      using molecular biology techniques.

<400> SEQUENCE: 84

Arg His Ala Ala Gly Val Ser Gly Thr Tyr Phe Asp Tyr
1               5                   10

<210> SEQ ID NO 85
<211> LENGTH: 5
<212> TYPE: PRT
<213> ORGANISM: Artificial Sequence
<220> FEATURE:
<223> OTHER INFORMATION: DOM23h-440 CDR1 Amino acid sequence produced
      using molecular biology techniques.

<400> SEQUENCE: 85

Asp Asp Arg Met Trp
1               5

<210> SEQ ID NO 86
<211> LENGTH: 17
<212> TYPE: PRT
<213> ORGANISM: Artificial Sequence
<220> FEATURE:
<223> OTHER INFORMATION: DOM23h-440 CDR2 Amino acid sequence produced
      using molecular biology techniques.

<400> SEQUENCE: 86

Ala Ile Asp Pro Gln Gly Gln His Thr Tyr Tyr Ala Asp Ser Val Lys
1               5                   10                  15

Gly

<210> SEQ ID NO 87
<211> LENGTH: 8
<212> TYPE: PRT
<213> ORGANISM: Artificial Sequence
<220> FEATURE:
<223> OTHER INFORMATION: DOM23h-440 CDR3 Amino acid sequence produced
      using molecular biology techniques.

<400> SEQUENCE: 87

Glu Leu Leu Ser Phe Asp Tyr Trp
1               5

<210> SEQ ID NO 88
<211> LENGTH: 6
<212> TYPE: PRT
<213> ORGANISM: Artificial Sequence
<220> FEATURE:
<223> OTHER INFORMATION: DOM23h-262-6 CDR1 Amino acid sequence produced
      using molecular biology techniques.

<400> SEQUENCE: 88

Asn Tyr Glu Met Ala Trp
1               5

<210> SEQ ID NO 89
<211> LENGTH: 17
```

```
<212> TYPE: PRT
<213> ORGANISM: Artificial Sequence
<220> FEATURE:
<223> OTHER INFORMATION: DOM23h-262-6 CDR2 Amino acid sequence produced
      using molecular biology techniques.

<400> SEQUENCE: 89

Leu Ile Ser Ala Glu Gly Thr Arg Thr Tyr Tyr Ala Asn Ser Val Lys
1               5                   10                  15

Gly

<210> SEQ ID NO 90
<211> LENGTH: 15
<212> TYPE: PRT
<213> ORGANISM: Artificial Sequence
<220> FEATURE:
<223> OTHER INFORMATION: DOM23h-262-6 CDR3 Amino acid sequence produced
      using molecular biology techniques.

<400> SEQUENCE: 90

Arg Arg Asp Ala Ser Met Gly His Thr Thr Arg Arg Phe Asp His
1               5                   10                  15

<210> SEQ ID NO 91
<211> LENGTH: 6
<212> TYPE: PRT
<213> ORGANISM: Artificial Sequence
<220> FEATURE:
<223> OTHER INFORMATION: DOM23h-262-10 CDR1 Amino acid sequence produced
      using molecular biology techniques.

<400> SEQUENCE: 91

Phe Asn Tyr Glu Met Ala
1               5

<210> SEQ ID NO 92
<211> LENGTH: 17
<212> TYPE: PRT
<213> ORGANISM: Artificial Sequence
<220> FEATURE:
<223> OTHER INFORMATION: DOM23h-262-10 CDR2 Amino acid sequence produced
      using molecular biology techniques.

<400> SEQUENCE: 92

Leu Ile Ser Ala Asp Gly Thr Arg Thr Tyr Tyr Ala Asn Ser Val Arg
1               5                   10                  15

Gly

<210> SEQ ID NO 93
<211> LENGTH: 15
<212> TYPE: PRT
<213> ORGANISM: Artificial Sequence
<220> FEATURE:
<223> OTHER INFORMATION: DOM23h-262-10 CDR3 Amino acid sequence produced
      using molecular biology techniques.

<400> SEQUENCE: 93

Arg Arg Asp Ala Ser Met Gly His Thr Thr Arg Arg Phe Asp Tyr
1               5                   10                  15

<210> SEQ ID NO 94
<211> LENGTH: 5
<212> TYPE: PRT
<213> ORGANISM: Artificial Sequence
<220> FEATURE:
<223> OTHER INFORMATION: DOM23h-271-3 CDR1 Amino acid sequence produced
      using molecular biology techniques.
```

<210> SEQ ID NO 95
<211> LENGTH: 17
<212> TYPE: PRT
<213> ORGANISM: Artificial Sequence
<220> FEATURE:
<223> OTHER INFORMATION: DOM23h-271-3 CDR2 Amino acid sequence produced using molecular biology techniques.

<400> SEQUENCE: 94

Glu Tyr Arg Met Trp
1               5

<210> SEQ ID NO 95
<211> LENGTH: 17
<212> TYPE: PRT
<213> ORGANISM: Artificial Sequence
<220> FEATURE:
<223> OTHER INFORMATION: DOM23h-271-3 CDR2 Amino acid sequence produced using molecular biology techniques.

<400> SEQUENCE: 95

Leu Ile Glu Pro Ile Gly Asn Arg Thr Tyr Tyr Ala Asp Ser Val Lys
1               5                   10                  15
Gly

<210> SEQ ID NO 96
<211> LENGTH: 15
<212> TYPE: PRT
<213> ORGANISM: Artificial Sequence
<220> FEATURE:
<223> OTHER INFORMATION: DOM23h-271-3 CDR3 Amino acid sequence produced using molecular biology techniques.

<400> SEQUENCE: 96

Gln Ile Pro Gly His Met Trp Thr Ala Asn Pro Arg Ser Asp Tyr
1               5                   10                  15

<210> SEQ ID NO 97
<211> LENGTH: 5
<212> TYPE: PRT
<213> ORGANISM: Artificial Sequence
<220> FEATURE:
<223> OTHER INFORMATION: DOM23h-271-7 CDR1 Amino acid sequence produced using molecular biology techniques.

<400> SEQUENCE: 97

Glu Tyr Arg Met Trp
1               5

<210> SEQ ID NO 98
<211> LENGTH: 17
<212> TYPE: PRT
<213> ORGANISM: Artificial Sequence
<220> FEATURE:
<223> OTHER INFORMATION: DOM23h-271-7 CDR2 Amino acid sequence produced using molecular biology techniques.

<400> SEQUENCE: 98

Ala Ile Glu Pro Ile Gly Asn Arg Thr Tyr Tyr Ala Asp Ser Val Lys
1               5                   10                  15
Gly

<210> SEQ ID NO 99
<211> LENGTH: 15
<212> TYPE: PRT
<213> ORGANISM: Artificial Sequence
<220> FEATURE:
<223> OTHER INFORMATION: DOM23h-271-7 CDR3 Amino acid sequence produced using molecular biology techniques.

<400> SEQUENCE: 99

Gln Ile Pro Gly Arg Lys Trp Thr Ala Asn Ser Arg Phe Asp Tyr
1               5                   10                  15

<210> SEQ ID NO 100
<211> LENGTH: 5
<212> TYPE: PRT
<213> ORGANISM: Artificial Sequence
<220> FEATURE:
<223> OTHER INFORMATION: DOM23h-271-12 CDR1 Amino acid sequence produced
      using molecular biology techniques.

<400> SEQUENCE: 100

Glu Tyr Arg Met Trp
1               5

<210> SEQ ID NO 101
<211> LENGTH: 17
<212> TYPE: PRT
<213> ORGANISM: Artificial Sequence
<220> FEATURE:
<223> OTHER INFORMATION: DOM23h-271-12 CDR2 Amino acid sequence produced
      using molecular biology techniques.

<400> SEQUENCE: 101

Leu Ile Glu Pro Ile Gly Asn Arg Thr Tyr Tyr Ala Asn Ser Val Arg
1               5                   10                  15

Gly

<210> SEQ ID NO 102
<211> LENGTH: 15
<212> TYPE: PRT
<213> ORGANISM: Artificial Sequence
<220> FEATURE:
<223> OTHER INFORMATION: DOM23h-271-12 CDR3 Amino acid sequence produced
      using molecular biology techniques.

<400> SEQUENCE: 102

Gln Ile Pro Gly His Met Trp Thr Ala Asn Pro Arg Ser Asp Tyr
1               5                   10                  15

<210> SEQ ID NO 103
<211> LENGTH: 5
<212> TYPE: PRT
<213> ORGANISM: Artificial Sequence
<220> FEATURE:
<223> OTHER INFORMATION: DOM23h-271-13 CDR1 Amino acid sequence produced
      using molecular biology techniques.

<400> SEQUENCE: 103

Glu Tyr Arg Met Trp
1               5

<210> SEQ ID NO 104
<211> LENGTH: 17
<212> TYPE: PRT
<213> ORGANISM: Artificial Sequence
<220> FEATURE:
<223> OTHER INFORMATION: DOM23h-271-13 CDR2 Amino acid sequence produced
      using molecular biology techniques.

<400> SEQUENCE: 104

Ala Ile Glu Pro Ile Gly Asn Arg Thr Tyr Tyr Ala Asn Ser Val Arg
1               5                   10                  15

Gly

<210> SEQ ID NO 105
<211> LENGTH: 15
<212> TYPE: PRT

```
<213> ORGANISM: Artificial Sequence
<220> FEATURE:
<223> OTHER INFORMATION: DOM23h-271-13 CDR3 Amino acid sequence produced
      using molecular biology techniques.

<400> SEQUENCE: 105

Gln Ile Pro Gly Arg Lys Trp Thr Ala Asn Ser Arg Phe Asp Tyr
1               5                   10                  15

<210> SEQ ID NO 106
<211> LENGTH: 5
<212> TYPE: PRT
<213> ORGANISM: Artificial Sequence
<220> FEATURE:
<223> OTHER INFORMATION: DOM23h-437-4 CDR1 Amino acid sequence produced
      using molecular biology techniques.

<400> SEQUENCE: 106

Asp Tyr Arg Met Trp
1               5

<210> SEQ ID NO 107
<211> LENGTH: 17
<212> TYPE: PRT
<213> ORGANISM: Artificial Sequence
<220> FEATURE:
<223> OTHER INFORMATION: DOM23h-437-4 CDR2 Amino acid sequence produced
      using molecular biology techniques.

<400> SEQUENCE: 107

Ala Ile Asp Ser Gln Gly His Thr Thr Tyr Tyr Ala Asp Ser Val Arg
1               5                   10                  15

Gly

<210> SEQ ID NO 108
<211> LENGTH: 7
<212> TYPE: PRT
<213> ORGANISM: Artificial Sequence
<220> FEATURE:
<223> OTHER INFORMATION: DOM23h-437-4 CDR3 Amino acid sequence produced
      using molecular biology techniques.

<400> SEQUENCE: 108

Tyr Gly Gly Tyr Phe Asp Tyr
1               5

<210> SEQ ID NO 109
<211> LENGTH: 5
<212> TYPE: PRT
<213> ORGANISM: Artificial Sequence
<220> FEATURE:
<223> OTHER INFORMATION: DOM23h-437-6 CDR1 Amino acid sequence produced
      using molecular biology techniques.

<400> SEQUENCE: 109

Asp Tyr Arg Met Trp
1               5

<210> SEQ ID NO 110
<211> LENGTH: 17
<212> TYPE: PRT
<213> ORGANISM: Artificial Sequence
<220> FEATURE:
<223> OTHER INFORMATION: DOM23h-437-6 CDR2 Amino acid sequence produced
      using molecular biology techniques.

<400> SEQUENCE: 110
```

Ala Ile Asp Ser Gln Gly His Thr Thr Tyr Tyr Ala Asp Ser Val Lys
1               5                   10                  15

Gly

<210> SEQ ID NO 111
<211> LENGTH: 7
<212> TYPE: PRT
<213> ORGANISM: Artificial Sequence
<220> FEATURE:
<223> OTHER INFORMATION: DOM23h-437-6 CDR3 Amino acid sequence produced
      using molecular biology techniques.

<400> SEQUENCE: 111

Tyr Gly Gly Tyr Phe Asp Tyr
1               5

<210> SEQ ID NO 112
<211> LENGTH: 5
<212> TYPE: PRT
<213> ORGANISM: Artificial Sequence
<220> FEATURE:
<223> OTHER INFORMATION: DOM23h-437-8 CDR1 Amino acid sequence produced
      using molecular biology techniques.

<400> SEQUENCE: 112

Asp Tyr Arg Met Trp
1               5

<210> SEQ ID NO 113
<211> LENGTH: 17
<212> TYPE: PRT
<213> ORGANISM: Artificial Sequence
<220> FEATURE:
<223> OTHER INFORMATION: DOM23h-437-8 CDR2 Amino acid sequence produced
      using molecular biology techniques.

<400> SEQUENCE: 113

Ala Ile Asp Ser Gln Gly His Thr Thr Tyr Tyr Ala Asn Ser Val Arg
1               5                   10                  15

Gly

<210> SEQ ID NO 114
<211> LENGTH: 7
<212> TYPE: PRT
<213> ORGANISM: Artificial Sequence
<220> FEATURE:
<223> OTHER INFORMATION: DOM23h-437-8 CDR3 Amino acid sequence produced
      using molecular biology techniques.

<400> SEQUENCE: 114

Tyr Gly Gly Tyr Phe Asp Tyr
1               5

<210> SEQ ID NO 115
<211> LENGTH: 5
<212> TYPE: PRT
<213> ORGANISM: Artificial Sequence
<220> FEATURE:
<223> OTHER INFORMATION: DOM23h-437-9 CDR1 Amino acid sequence produced
      using molecular biology techniques.

<400> SEQUENCE: 115

Ser Asp Tyr Arg Met
1               5

<210> SEQ ID NO 116

```
<211> LENGTH: 17
<212> TYPE: PRT
<213> ORGANISM: Artificial Sequence
<220> FEATURE:
<223> OTHER INFORMATION: DOM23h-437-9 CDR2 Amino acid sequence produced
      using molecular biology techniques.

<400> SEQUENCE: 116

Ala Ile Asp Ser Gln Gly His Thr Thr Tyr Tyr Ala Asn Ser Val Arg
1               5                   10                  15

Gly

<210> SEQ ID NO 117
<211> LENGTH: 7
<212> TYPE: PRT
<213> ORGANISM: Artificial Sequence
<220> FEATURE:
<223> OTHER INFORMATION: DOM23h-437-9 CDR3 Amino acid sequence produced
      using molecular biology techniques.

<400> SEQUENCE: 117

Tyr Gly Gly Tyr Phe Asp Tyr
1               5

<210> SEQ ID NO 118
<211> LENGTH: 5
<212> TYPE: PRT
<213> ORGANISM: Artificial Sequence
<220> FEATURE:
<223> OTHER INFORMATION: DOM23h-439-6 CDR1 Amino acid sequence produced
      using molecular biology techniques.

<400> SEQUENCE: 118

Thr Glu Gln Met Trp
1               5

<210> SEQ ID NO 119
<211> LENGTH: 17
<212> TYPE: PRT
<213> ORGANISM: Artificial Sequence
<220> FEATURE:
<223> OTHER INFORMATION: DOM23h-439-6 CDR2 Amino acid sequence produced
      using molecular biology techniques.

<400> SEQUENCE: 119

Arg Ile Asp Ser Pro Gly Gly Arg Thr Tyr Tyr Ala Asp Ser Val Arg
1               5                   10                  15

Gly

<210> SEQ ID NO 120
<211> LENGTH: 13
<212> TYPE: PRT
<213> ORGANISM: Artificial Sequence
<220> FEATURE:
<223> OTHER INFORMATION: DOM23h-439-6 CDR3 Amino acid sequence produced
      using molecular biology techniques.

<400> SEQUENCE: 120

Arg His Ala Ala Gly Val Ser Gly Thr Tyr Phe Asp Tyr
1               5                   10

<210> SEQ ID NO 121
<211> LENGTH: 5
<212> TYPE: PRT
<213> ORGANISM: Artificial Sequence
<220> FEATURE:
<223> OTHER INFORMATION: DOM23h-439-8 CDR1 Amino acid sequence produced
``` using molecular biology techniques.

<400> SEQUENCE: 121

Thr Glu Gln Met Trp
1               5

<210> SEQ ID NO 122
<211> LENGTH: 17
<212> TYPE: PRT
<213> ORGANISM: Artificial Sequence
<220> FEATURE:
<223> OTHER INFORMATION: DOM23h-439-8 CDR2 Amino acid sequence produced
      using molecular biology techniques.

<400> SEQUENCE: 122

Arg Ile Asp Ser Pro Gly Gly Arg Thr Tyr Tyr Ala Asn Ser Val Arg
1               5                   10                  15

Gly

<210> SEQ ID NO 123
<211> LENGTH: 13
<212> TYPE: PRT
<213> ORGANISM: Artificial Sequence
<220> FEATURE:
<223> OTHER INFORMATION: DOM23h-439-8 CDR3 Amino acid sequence produced
      using molecular biology techniques.

<400> SEQUENCE: 123

Arg His Ala Ala Gly Val Ser Gly Thr Tyr Phe Asp Tyr
1               5                   10

<210> SEQ ID NO 124
<211> LENGTH: 4
<212> TYPE: PRT
<213> ORGANISM: Artificial Sequence
<220> FEATURE:
<223> OTHER INFORMATION: Amino acid sequence prodiced using molecular
      biology techniques.

<400> SEQUENCE: 124

Gly Thr Glu Gln
1

<210> SEQ ID NO 125
<211> LENGTH: 10
<212> TYPE: PRT
<213> ORGANISM: Artificial Sequence
<220> FEATURE:
<223> OTHER INFORMATION: Amino acid sequence prodiced using molecular
      biology techniques.

<400> SEQUENCE: 125

Asp Ala Ser Met Gly His Thr Thr Arg Arg
1               5                   10

<210> SEQ ID NO 126
<211> LENGTH: 20
<212> TYPE: PRT
<213> ORGANISM: Artificial Sequence
<220> FEATURE:
<223> OTHER INFORMATION: Amino acid sequence prodiced using molecular
      biology techniques.

<400> SEQUENCE: 126

Pro Gly His Lys Trp Thr Ala Asn Ser Arg Phe Asp Tyr Trp Gly Gln
1               5                   10                  15

```
Gly Thr Leu Val
            20

<210> SEQ ID NO 127
<211> LENGTH: 7
<212> TYPE: PRT
<213> ORGANISM: Artificial Sequence
<220> FEATURE:
<223> OTHER INFORMATION: Amino acid sequence prodiced using molecular
      biology techniques.

<400> SEQUENCE: 127

Trp Asp Gly Val His Ala Gln
1               5

<210> SEQ ID NO 128
<211> LENGTH: 9
<212> TYPE: PRT
<213> ORGANISM: Artificial Sequence
<220> FEATURE:
<223> OTHER INFORMATION: Amino acid sequence prodiced using molecular
      biology techniques.

<400> SEQUENCE: 128

Asp Tyr Trp Gly Gln Gly Thr Leu Val
1               5

<210> SEQ ID NO 129
<211> LENGTH: 6
<212> TYPE: PRT
<213> ORGANISM: Artificial Sequence
<220> FEATURE:
<223> OTHER INFORMATION: Amino acid sequence prodiced using molecular
      biology techniques.

<400> SEQUENCE: 129

Ser Ser Thr Ser Pro Phe
1               5

<210> SEQ ID NO 130
<211> LENGTH: 8
<212> TYPE: PRT
<213> ORGANISM: Artificial Sequence
<220> FEATURE:
<223> OTHER INFORMATION: Amino acid sequence prodiced using molecular
      biology techniques.

<400> SEQUENCE: 130

Ala Ala Gly Val Ser Gly Tyr Phe
1               5
```